US012303236B2

(12) United States Patent
Ha et al.

(10) Patent No.: US 12,303,236 B2
(45) Date of Patent: May 20, 2025

(54) CONTACTLESS SEISMOCARDIOGRAPHY

(71) Applicant: Massachusetts Institute of Technology, Cambridge, MA (US)

(72) Inventors: Unsoo Ha, Cambridge, MA (US); Fadel Adib, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 125 days.

(21) Appl. No.: 18/043,641

(22) PCT Filed: Aug. 27, 2021

(86) PCT No.: PCT/US2021/047876
§ 371 (c)(1),
(2) Date: Mar. 1, 2023

(87) PCT Pub. No.: WO2022/055719
PCT Pub. Date: Mar. 17, 2022

(65) Prior Publication Data
US 2023/0371820 A1     Nov. 23, 2023

Related U.S. Application Data

(60) Provisional application No. 63/075,432, filed on Sep. 8, 2020.

(51) Int. Cl.
*A61B 5/02*     (2006.01)
*A61B 5/00*     (2006.01)
*A61B 5/0507*    (2021.01)

(52) U.S. Cl.
CPC .............. *A61B 5/02* (2013.01); *A61B 5/0507* (2013.01); *A61B 5/7264* (2013.01); *A61B 2562/0204* (2013.01)

(58) Field of Classification Search
CPC .... A61B 2562/0204; A61B 2562/0228; A61B 5/02; A61B 5/0507; A61B 5/1102; A61B 5/318; A61B 5/7264
See application file for complete search history.

(56) References Cited

U.S. PATENT DOCUMENTS 10,746,852 B2    8/2020   Adib et al.
2010/0130873 A1   5/2010   Yuen et al.
(Continued)

FOREIGN PATENT DOCUMENTS

| EP | 2247233 B1 | 10/2015 |
|---|---|---|
| RU | 77766 U1 | 11/2008 |
| WO | WO 2017/083754 A1 | 5/2017 |

OTHER PUBLICATIONS

PCT International Search Report and Written Opinion dated Mar. 16, 2023 for International Application No. PCT/US2022/048374; 18 pages.

(Continued)

*Primary Examiner* — Mark D Remaly
(74) *Attorney, Agent, or Firm* — Daly, Crowley, Mofford & Durkee, LLP

(57) ABSTRACT

A contactless sensor includes a cardiac beamformer, a wireless-to-seismocardiogram translator, and an automatic labeler. The cardiac beamformer determines at least one beam for receiving wireless signals generated based on movement of a heart. The at least one beam is generated based on phase information and a heart signal extracted from a time-domain signal generated from one or more receiver elements. The wireless-to-seismocardiogram translator implements a convolutional neural network to transform time-series data detected from the at least one beam to a seismocardiogram. The automatic labeler identifies and labels one or more micro-cardiac events in the time-series (Continued)

data. The cardiac beamformer may be considered an optional feature in one or more implementations.

20 Claims, 24 Drawing Sheets

(56) References Cited

U.S. PATENT DOCUMENTS

| | | | |
|---|---|---|---|
| 2014/0163343 | A1 | 6/2014 | Heneghan et al. |
| 2015/0038856 | A1 | 2/2015 | Houlton et al. |
| 2016/0361041 | A1 | 12/2016 | Barsimantov et al. |
| 2017/0311901 | A1 | 11/2017 | Zhao et al. |
| 2019/0216393 | A1 | 7/2019 | Baheti et al. |
| 2020/0138306 | A1 | 5/2020 | Li et al. |

OTHER PUBLICATIONS

Ha et al., "WiStress", Proceedings of the ACM On Interactive, Mobile, Wearable and Ubiquitous Technologies, ACMPUB27, vol. 5, No. 3, Sep. 14, 2021. pp. 1-37, 37 pages.
Nouman et al., "Recent Advances in Contactless Sensing Technologies for Mental Health Monitoring", IEEE Internet of Things Journal, IEEE, vol. 9, No. 1, Jul. 16, 2021. pp. 274-297, 24 pages.
Can et al., "Stress Detection in Daily Life Scenarios Using Smart Phones and Wearable Sensors: A Survey", Journal of Biomedical Informatics, vol. 92, Feb. 27, 2019; 22 pages.
Dai et al., "Comparing Stress Prediction Models Using Smartwatch Physiological Signals and Participant Self-Reports", Computer Methods and Programs in Biomedicine, Elsevier, vol. 202, May 30, 2021; 11 pages.
Zhang et al., "Non-Contact Dual-Modality Emotion Recognition System by CW Radar and RGB Camera", IEEE Sensors Journal, IEEE, vol. 21, No. 20, Aug. 24, 2021; pp. 23198-23212; 15 pages.
International Preliminary Report on Patentability dated Mar. 23, 2023 for International Application No. PCT/US2021/047876; 10 Pages.
Acharya, et al.; "Heart Rate Variability: a review"; Medical & Biological Engineering & Computing; pp. 1031-1051; Jan. 2007; 22 Pages.
Adib, et al.; "Capturing the Human Figure Through a Wall"; ACM Transactions on Graphics, vol. 34, No. 6, Article 219; Nov. 2015; 13 Pages.
Adib; et al.; "3D Tracking via Body Radio Reflections"; Proceeding of the $11^{th}$ USENIX Symposium on Networked Systems Design and Implementation (NSDI' 14); Apr. 2-4, 2014; 14 Pages.
Adib, et al.; "Smart Homes that Monitor Breathing and Heart Rate"; Heath Sensors & Monitoring; pp. 836-846; CHI 2015; 10 Pages.
Aigrain, et al.; "Person-Specific Behavioural Features for Automatic Stress Detection"; 2015 11th IEEE International Conference and Workshops on Automatic Face and Gesture Recognition (FG); May 4-8, 2015; 6 Pages.
Aigrain, et al.; "Multimodal Stress Detection from Multiple Assessments"; IEEE Transactions on Affective Computing; vol. 9; No. 4; pp. 491-506; Oct.-Dec. 2018; 16 Pages.
Al' Absi, et al.; "Cardiovascular and Neuroendocrine Adjustment to Public speaking and Mental Arithmetic Stress"; Psychophysiology, 34 (1997); pp. 266-275; 11 Pages.
Alberdi, et al.; "Towards an Automatic Early Stress Recognition System for Office Environments based on Multimodal Measurements: A Review"; Journal of Biomedical Informatics 59; pp. 49-75; Nov. 2015; 27 Pages.
Ali, et al.; "Can Children Learn Creativity From A Social Robot"; C&C' 19; Session 8: Creativity with Kids; Jun. 23-26, 2019; 10 Pages.
Anliker, et al.; "AMON: A Wearable Multiparameter Medical Monitoring and Alert System"; IEEE Transactions on Information Technology in Biomedicine; vol. 8, No. 4; pp. 415-427; Dec. 2004; 13 Pages.

Antink, et al.; "A Broader Look: Camera-Based Vital Sign Estimation Across the Spectrum"; IMIA Yearbook of Medical Informatics; pp. 102-114; 2019; 13 Pages.
Arsalan, et al.; "Improved Contactless Heartbeat Estimation in FMCW Radar via Kalman Filter Tracking"; IEEE Sensors Letters; vol. 4, No. 5; May 2020; 4 Pages.
Bargas-Avila, et al.; "Old Wine in New Bottles or Novel Challenges? A Critical Analysis of Empirical Studies of User Experience"; CHI 2011; Session: User Experience; May 7-12, 2011; 10 Pages.
Bauer, et al.; "Can Smartphones Detect Stress-Related Changed in the Behaviour of Individuals?"; Work in Progress session at PerCom 2012; Mar. 19-23, 2012; 4 Pages.
Begum, et al.; "Using Calibration and Fuzzification of Cases for Improved Diagnosis and Treatment of Stress"; Jan. 2006; 10 Pages.
Benedetti, et al.; "When Words are Painful: Unraveling the Mechanisms of the Nocebo Effect"; Neuroscience 147; pp. 260-271; 2007; 12 Pages.
Bogomolov, et al.; "Daily Stress Recognition from Mobile Phone Data, Weather Conditions and Individual Traits"; MM'14; pp. 477-486; Nov. 3-7, 2014; 10 Pages.
Bousefsaf, et al.; "Remote assessment of the Heart Rate Variability to Detect Mental Stress"; 2013 $7^{th}$ International Conference on Pervasive Computing Technologies for Healthcare and Workshops; pp. 348-351; Jan. 2013; 4 Pages.
Breazeal, et al.; "Designing Social Robots for Older Adults"; The Bridge; Spring 2019; pp. 22-31 (10 pages).
Can, et al.,; "Continuous Stress Detection Using Wearable Sensors in Real Life: Algorithmic Programming Contest Case Study"; Sensors 2019; vol. 19; Apr. 18, 2019; 21 Pages.
Cao, et al.; "NASA TLX: Software for Assessing Subjective Mental Workload"; Behavior Research Methods; vol. 41; pp. 113-117; 2009; 5 Pages.
Chandola, et al.; "Chronic Stress at Work and the Metabolic Syndrome: Prospective Study"; BMJ; Jan. 20, 2006; 5 Pages.
Chen, et al; "Improved Baselines with Momentum Contrastive Learning"; Mar. 9, 2020; 3 Pages.
Chooruang, et al.; "Wireless Heart Rate Monitoring System Using MQTT"; 2016 International Electrical Engineering Congress; Procedia Computer Science 86; pp. 160-163; Mar. 2-4, 2016; 4 Pages.
Ciman, et al.; "Individuals' Stress Assessment Using Human-Smartphone Interaction Analysis"; IEEE Transactions on Affective Computing; vol. ; No. 1; pp. 51-65; Jan.-Mar. 2018; 15 Pages.
Cotter, et al.; "The Stone-Weierstrass Theorem and Its Application to Neural Networks"; IEEE Transactions on Neural Networks; vol. 1; No. 4; pp. 290-295; Dec. 1990; 6 Pages.
De Santos Sierra, et al.; "Stress Detection by means of Stress Physiological Template"; 2011 Third World Congress on Nature and Biologically Inspired Computing; pp. 131-136; Oct. 19-21, 2011; 6 Pages.
Dwibedi, et al.; "Counting Out Time: Class Agnostic Video Repetition Counting in the Wild"; 2020 IEEE/CVF Conference on Computer Vision and Pattern Recognition (CVPR); Jun. 13-19, 2020; 10 Pages.
Foote; "Visualizing Music and Audio using Self-Similarity"; Multimedia '99: Proceedings of the seventh ACM international conference on Multimedia (Part 1); pp. 77-80; Oct. 1999; 4 pages.
Foote, et al.; "Visualizing Music Structure and Rhythm via Self-Similarity"; Sep. 2001; 5 Pages.
Foote, et al.; "Media Segmentation using Self-Similarity Decomposition"; Proceedings of SP IE—The International Society for Optical Engineering; Jan. 2003; 10 Pages.
Fuller, et al.; "Reliability and Validity of Commercially Available Wearable Devices for Measuring Steps, Energy Expenditure, and Heart Rate: Systematic Review"; JMIR Mhealth 2020; vol. 8; Issue 9; Mar. 2020; 24 Pages.
Garcia-Ceja, et al.; "Automatic Stress Detection in Working Environments From Smartphones' Accelerometer Data: A First Step"; IEEE Journal of Biomedical and Health Informatics; vol. 20; No. 4; pp. 1053-1060; Jul. 2016; 8 Pages.
Garcia-Gonzalez, et al.; "A Comparison of Heartbeat Detectors for the Seismocardiogram"; Computing in Cardiology 2013; Sep. 22-25, 2013; 4 Pages.

(56) References Cited

OTHER PUBLICATIONS

Garett, et al.; "A Longitudinal Analysis of Stress Among Incoming College Freshmen"; Journal of American College Health; vol. 65; No. 5; pp. 331-338; May 2, 2017; 9 Pages.

Ge, et al.; "Evaluating the Accuracy of Wearable Heart Rate Monitors"; 2016 2nd International Conference on Advances in Computing, Communication, & Automation (ICACCA) (Fall); Sep. 30-Oct. 1, 2016; 6 Pages.

Georgiou, et al.; "Can Wearable Devices Accurately Measure Heart Rate Variability? A Systematic Review"; Folia Medica; vol. 60; No. 1; Jan. 2018; 15 Pages.

Giakoumis, et al.; "Using Activity-Related Behavioural Features Towards More Effective Automatic Stress Detection"; PLoS One; vol. 7; Issue 9; Sep. 19, 2012; 16 Pages.

Giannakakis, et al.; "Stress and Anxiety Detection Using Facial Cues from Videos"; Biomedical Signal Processing and Control; vol. 31; pp. 89-101; Jul. 2016; 13 Pages.

Gino; "Are you Too Stressed to Be Productive? Or Not Stressed Enough?"; Harvard Business Review; Stress Management; Apr. 14, 2016; 6 Pages.

Gjoreski, et al.; "Continuous Stress Detection Using a Wrist Device—In Laboratory and Real Life"; UBICOMP/ISWC'16; pp. 1185-1193; Sep. 12-16, 2016; 9 Pages.

Gjoreski, et al.; "Monitoring Stress with a Wrist Device Using Context"; Journal of Biomedical Information; vol. 73; pp. 159-170; Aug. 2017; 12 Pages.

Ha, et al.; "Contactless Seismocardiography via Deep Learning Radars"; MobiCom '20; Sep. 21-25, 2020; 14 Pages.

Halkos, et al.; "The Influence of Stress and Satisfaction on Productivity"; University of Thessaly, Department of Economics; Feb. 2008; 27 Pages.

Hart; "NASA-Task Load Index (NASA-TLX); 20 Years Later"; Proceeding of the Human Factors and Ergonomics Society $50^{th}$ Annual Meeting—2006; pp. 904-908; Oct. 2006; 5 Pages.

Hart, et al.; "Development of NASA-TLX(Task Load Index): Results of Empirical and Theoretical Research"; Advances in Psychology; vol. 52; pp. 139-183; 1988; 46 Pages.

Healey, et al.; Detecting Stress During Real-World Driving Tasks Using Physiological Sensors; IEEE Transactions on Intelligent Transportation Systems; vol. 6; No. 2; Jun. 2005; pp. 156-166; 11 Pages.

Hendy, et al.; "Measuring Subjective Workload: When is One Scale Better Than Many?"; Human Factors; vol. 35. No. 4; pp. 579-601; Dec. 1993; 26 Pages.

Ho; "Random Decision Forests"; Proceedings of 3rd International Conference on Document Analysis and Recognition; pp. 278-282; Aug. 14-16, 1995; 5 Pages.

Hovsepian, et al.; "cStress: Towards a Gold Standard for Continuous Stress Assessment in the Mobile Environment"; UBICOMP '15; Sep. 7-11, 2015; 12 Pages.

Ibrahim, et al.; "CrossCount: A Deep Learning System for Device-Free Human Counting Using WiFi"; IEEE Sensors Journal; vol. 19; No. 21; pp. 9921-9928; Nov. 1, 2019; 8 Pages.

Iovescu, et al.; The Fundamental of Millimeter Wave Radar Sensors; Jul. 2020; 9 Pages.

Jensen, et al.; "Spontaneous Movements with Various Seated-Workplace Adjustments"; Clinical Biomechanics; vol. 7; Issue 2; pp. 87-90; May 1992; 4 Pages.

Kabat-Zinn, et al.; "Effectiveness of a Meditation-Based Stress Reduction Program in the Treatment of Anxiety Disorders"; Am J Psychiatry 149:7; pp. 936-943; Jul. 1992; 8 Pages.

Karvounas, et al.; "ReActNet: Temporal Localization of Repetitive Activities in Real-World Videos"; Oct. 2019; 10 Pages.

Kellmann; "Preventing overtraining in athletes in high-intensity sports and stress/ recovery monitoring"; Scandinavian Journal of Medicine & Science in Sports; vol. 20 (Suppl. 2); pp. 95-102; 2010; 8 Pages.

Kim, et al.; "Stress and Heart Rate Variability: A Meta-Analysis and Review of the Literature"; Korean Neuropsychiatric Association; Psychiatry Investig. 2018; vol. 15 (3); pp. 235-245; Feb. 2018; 11 Pages.

Kim, et al.; "Emotion Recognition Based on Physiological Changes in Music Listening"; IEEE Transactions on Pattern Analysis and Machines Intelligence; vol. 30: No. 12; pp. 2067-2083; Dec. 2008; 17 Pages.

King, et al.; "Micro-stress EMA: A Passive Sensing Framework for Detecting in-the-wild Stress in Pregnant Mothers"; Proc. ACM Interact. Mob. Wearable Ubiquitous Techno. 3, 3, Article 91; Sep. 2019; 22 Pages.

Kowalski, et al.; "Well-Being and HRM in the Changing Workplace"; The International Journal of Human Resource Management, 28:16; pp. 2229-2255; Jul. 9, 2017; 28 Pages.

Kurniawan, et al.; "Stress Detection from Speech and Galvanic Skin Response Signals"; Proceedings of the 26th IEEE International Symposium on Computer-Based Medical Systems; Jun. 20-22, 2013; 6 Pages.

Levenstein, et al.; "Development of the Perceived Stress Questionnaire: A New Tool For Psychosomatic Research"; Journal of Psychosomatic Research; vol. 37; No. 1; pp. 19-32; Jan. 1993; 14 Pages.

Liapis, et al.; "Stress in Interactive Applications: Analysis of the Valence-Arousal Space Based on Physiological Signals and Self-Reported Data"; Multimedia Tools and Applications; vol. 76; pp. 5051-5071; Jun. 11, 2016; 21 Pages.

Liaw, et al.; "Classification and Regression by randomForest"; vol. 2/3; pp. 18-22; Dec. 2002; 5 Pages.

Lin, et al.; "Splog Detection Using Self-similarity Analysis on Blog Temporal Dynamics"; AIRWeb '07: Proceedings of the 3rd international workshop on Adversarial information retrieval on the web; May 8, 2007; 8 Pages.

Liu, et al.; "Happiness at Your Fingertips: Assessing Mental Health with Smartphone Photoplethysmogram-Based Heart Rate Variability Analysis"; Telemedicine and e-Health; vol. 26; No. 12; pp. 1483-1491; Dec. 2020; 9 Pages.

Lupien; "How to Measure Stress in Humans"; Centre for Studies on Human Stress (CSHS); 2013; 28 Pages.

Maaoui, et al.; "Emotion Recognition for Human-Machine Communication"; 2008 IEEE/RSJ International Conference on Intelligent Robots and Systems Acropolis Convention Center; Sep. 22-26, 2008; 6 Pages.

Marcovecchio, et al.; "The Effects of Acute and Chronic Stress on Diabetes Control"; Endocrinology; vol. 5 Issue 247; pt 10; Oct. 23, 2012; 4 Pages.

Mcduff, et al.; "AffectAura: An Intelligent System for Emotional Memory"; Session: Affective Presence; CHI 2012; May 5-10, 2012; 10 Pages.

Melillo, et al.; " Nonlinear Heart Rate Variable Features for Real-Life Stress Detection. Case Study: Students Under Stress Due to University Examination"; BioMedical Engineering Online; 2011; 13 Pages.

Mishra, et al.; "The Case for a Commodity Hardware Solution for Stress Detection"; UbiComp/ISWC' 18 Adjunct; pp. 1717-1728; Oct. 8-12, 2018; 12 Pages.

Mishra, et al.; "Evaluating the Reproducibility of Physiological Stress Detection Models"; Proceeding ACM Interact. Mob. Wearable Ubiquitous Technol.; vol. 4; No. 4; Article 147; Dec. 2020; 29 Pages.

Misra; "Academic Stress of College Students: Comparison of Student and Faculty Perceptions"; College Student Journal; Jan. 2000; 18 Pages.

Muraoka, et al.; "Twenty-Four-Hour Ambulatory Blood Pressure and Heart Rate Monitoring in Combat-Related Posttraumatic Stress Disorder"; Journal of Traumatic Stress; vol. 11; No. 3; pp. 473-484; 1998; 12 Pages.

Muscariello, et al.; "Towards Robust Word Discovery by Self-Similarity Matrix Comparison"; ICASSP; pp. 5640-5643; 2011; 4 Pages.

(56) References Cited

OTHER PUBLICATIONS

Þ órarinsdóttir, et al.; "Smartphone-Based Self-Assessment of Stress in Healthy Adult Individuals: A Systematic Review"; Journal of Medical Internet Research; J Med Internet Res; vol. 19; Issue 2; e41; 2017; 13 Pages.
O'Donovan, et al.; "Stress Appraisals and Cellular Aging: A Key Role for Anticipatory Threat in The Relationship between Psychological Stress and Telomere Length"; Brian, Behavior, and Immunity 26; pp. 573-579; Jan. 2012; 7 Pages.
P. Karthikeyan, et al.; "Multiple Physiological Signal-Based Human Stress Identification Using Non-Linear Classifiers"; Elektonika IR Elektrotechnika, ISSN 1392-1215; vol. 19; No. 7; 2013; 6 Pages.
Park, et al.; "Heart Rate Variability as a Marker of Distress and Recovery: The Effect of Brief Supportive Expressive Group Therapy With Mindfulness in Cancer Patients"; Integrative Cancer Therapies; vol. 17(3); pp. 825-831; 2018; 7 Pages.
Picard, et al.; "Toward Machine Emotional Intelligence: Analysis of Affective Physiological State"; IEEE Transactions on Pattern Analysis and Machine Intelligence; vol. 23; No. 10; pp. 1175-1191; Oct. 2001; 17 Pages.
Pobiruchin, et al.; "Accuracy and Adoption of Wearable Technology Used by Active Citizens: A Marathon Event Field Study"; JMIR Mhealth Uhealth; vol. 5; Issue 2; e24; 2017; 14 Pages.
Postolache, et al.; "Unobtrusive and Non-Invasive Sensing Solutions for On-Line Physiological Parameters Monitoring"; Lecture Notes in Electrical Engineering; Oct. 2010; 39 Pages.
Rasool, et al.; "Sustainable Work Performance: The Roles of Workplace Violence and Occupational Stress"; Int. J. Environ. Res. Public Health 17, 912; Feb. 2020; 12 Pages.
Rubio, et al.; "Evaluation of Subjective Mental Workload: A Comparison of SWAT, NASA-TLX, and Workload Profile Methods"; Applied Psychology: An International Review: 53 (1); 61-86; 2004; 26 Pages.
Sakamoto, et al.; "Feature-Based Correlation and Topological Similarity for Interbeat Interval Estimation Using Ultrawideband Radar"; IEEE Transactions on Biomedical Engineering; vol. 63; No. 4; pp. 747-757; Apr. 2016; 11 Pages.
Sarker, et al.; "Finding Significant Stress Episodes in a Discontinuous Time Series of Rapidly Varying Mobile Sensor Data"; Health Support and Management; CHI; pp. 4489-4501; May 2016; 13 pages.
Scholz, et al.; "Go no-go Performance under Psychosocial Stress: Beneficial Effects of Implementation Intentions"; Neurobiology of Learning and Memory 91; pp. 89-92; Oct. 2008; 4 Pages.
Schoofs, et al.; "Psychosocial Stress Induces Working Memory Impairments in an n-back Paradigm"; Psychoneuroendocrinology 33; pp. 643-653; Feb. 2008; 11 Pages.
Shah, et al.; "Perceived Stress, Sources and Severity of Stress Among Medical Undergraduates in a Pakistani Medical School"; BMC Medical Education; 10:2; 2010; 8 Pages.
Adib et al.; "Smart homes that monitor breathing and heart rate"; CHI '15 Proceedings of the 33$^{rd}$ Annual ACM Conference on Human Factors in Computing Systems; Apr. 2015; 11 Pages.
Alizadeh et al.; "Remote heart rate sensing with mm-wave radar"; 2018 18$^{th}$ International Symposium on Antenna Technology and Applied Electromagnetics; Aug. 2018; 2 Pages.
Churkin et al.; "Millimeter-wave radar for vital signs monitoring"; 2015 IEEE International Conference on Microwaves, Communications, Antennas and Electronic Systems; Nov. 2015; 4 Pages.
Dong et al.; "Cardiogram detection with a millimeter-wave radar sensor"; 2020 IEEE Radio and Wireless Symposium; Jan. 2020; 3 Pages.
Fang et al.; "Bodyscan: Enabling radio-based sensing on wearable devices for contactless activity and vital signs monitoring"; Proceedings of the 14$^{th}$ Annual international conference on mobile systems, applications and services; Jun. 2016; 14 Pages.
Lee et al.; "Heart Rate Estimated from Body Movements at Six Degrees of Freedom by Convolutional Neural Networks"; Sensors; vol. 2018; May 1, 2018; 19 Pages.
Li et al.; "Standalone systolic profile detection of noncontact scg signal with lstm network"; IEEE Sensors Journal; vol. 20, No. 6; Mar. 15, 2020; 9 Pages.
Lin et al.; "Cardiac scan: A non-contact and continuous heart-based user authentication system"; Proceedings of the 23$^{rd}$ Annual International Conference on Mobile Computing and Networking; Oct. 2017; 14 Pages.
Mora et al.; "Fully Automated Annotation of Seismocardiogram for Noninvasive Vital Sign Measurements"; IEEE Transactions on Instrumentation and Measurement; vol. 69, No. 4; Apr. 4, 2020; 10 Pages.
PCT International Search Report and Written Opinion dated Jan. 31, 2022 for International Application No. PCT/US2021/47876; 14 Pages.
Petkie et al.; "Millimeter wave radar for remote measurement of vital signs"; 2009 IEEE Radar Conference; May 2009; 3 Pages.
Wang et al.; "Phasebeat: Exploiting csi phase data for vital sign monitoring with commodity wifi devices"; 2017 IEEE 37$^{th}$ International Conference on Distributed Computing Systems; Jun. 2017; 10 Pages.
Will et al.; "Radar-based heart sound detection"; Scientific Reports; Jul. 26, 2018; 14 Pages.
Xia et al.; "Non-contact sensing of seismocardiogram signals using microwave doppler radar"; IEEE Sensors Journal; vol. 18, No. 14; Jul. 15, 2018; 9 Pages.
Xia et al.; "The delineation of fiducial points for non-contact radar seismocardiogram signals without conccurrent ecg"; IEEE Journal of Biomedical and Health Informatics; vol. 25, No. 4; Apr. 2021; 10 Pages.
Yang et al.; "Monitoring vital signs using millimeter wave"; Proceedings of the 17$^{th}$ ACM international symposium on mobile ad hoc networking and computing; Jul. 2016; 10 Pages.
Zhao; "Emotion recognition using wireless signals"; Proceedings of the 22$^{nd}$ annual international conference mobile computing and networking; Oct. 2016; 52 Pages.
U.S. Appl. No. 18/686,104, filed Feb. 23, 2024, Adib et al.
Preliminary Amendment filed Feb. 23, 2023, for U.S. Appl. No. 18/686,104; 31 pages.
Tafet, et al.; "Psychoneuroendocrinological Links Between Chronic Stress and Depression"; Progress in Neuro-Psychopharmacology & Biological Psychiatry 27; pp. 893-903; 2003; 11 Pages.
Tan, et al.; "Combining Think-aloud and Physiological Data to Understand Video Game Experiences"; Session: Studying and Designing Gameplay; CHI; pp. 381-390; 2014; 10 Pages.
Teigen; "Yerkes-Dodsen: A Law for all Seasons"; Theory & Phychology; Nov. 1994; 25 Pages.
Tse, et al.; "Fundamentals of Wireless Communication"; Sep. 10, 2004; 647 Pages.
Texas Instruments; "Single-Chip 76- to 81-GHz mmWave Sensor"; Data Sheet IWR1443; SWRS211C; May 2017; 76 Pages.
Vanitha, et al.; "Real Time Stress Detection System Based on EEG Signals"; Biomedical Research; Special Issue: S271-S275; Jan. 2016; 6 Pages.
Vildjiounaite, et al.; "Unobstructive Stress Detection on the Basis of Smartphone Usage Data"; Personal and Ubiquitous Computing; 22:671-688; Jun. 2018; 18 Pages.
Wang, et al.; "Gait Recognition Using WiFi Signals"; UBICOMP' 16; Sep. 12-16, 2016; 11 Pages.
Wei; "Stress Emotion Recognition Based on RSP and EMG Signals"; Advanced Materials Research; ISSN: 1662-8985; vol. 709; pp. 827-831; Jun. 27, 2013; 5 Pages.
Wei; "Online Music Performance Tracking Using Parallel Dynamic Time Warping"; Conference Paper; Aug. 2018; 9 Pages.
Wijsman, et al.; "Wearable Physiological Sensors Reflect Mental Stress State in Office-Like Situations"; 2013 Humaine Association Conference on Affective Computing and Intelligent Interaction; pp. 600-605; Sep. 2-5, 2013; 6 Pages.
Wu, et al.; "Modeling Perceived Stress via HRV and Accelerometer Sensor Streams"; 2015 37th Annual International Conference of the IEEE Engineering in Medicine and Biology Society (EMBC); Aug. 25-29, 2015; 4 Pages.

(56) References Cited

OTHER PUBLICATIONS

Yang, et al.; "Textile-based Breath-sensing Belt"; 2010 Digest of Technical Papers International Conference on Consumer Electronics (ICCE); Jan. 9-13, 2010; 2 Pages.
Zeng, et al.; "MultiSense: Enabling Multi-person Respiration Sensing with Commodity WiFi"; Proc. ACM Interact. Mob. Wearable Ubiquitous Technol.; vol. 4; No. 3; Article 102; Sep. 2020; 29 Pages.
Zhao, et al.; "Emotion Recognition using Wireless Signals"; MobiCom'16; Oct. 3-7, 2016; 14 Pages.
Zhao, et al.; "Through-Wall Human Pose Estimation Using Radio Signals"; 2018 IEEE/CVF Conference on Computer Vision and Pattern Recognition; pp. 7356-7365; Jun. 18-23, 2018; 10 Pages.
Zhao, et al.; "Through-Wall Human Mesh Recovery Using Radio Signals"; 2019 IEEE/CVF International Conference on Computer Vision (ICCV); pp. 10113-10122; Oct. 27-Nov. 2, 2019; 10 Pages.
Zheng, et al; "Workload Assessment of Surgeons: Correlation Between NASA TLX and Blinks"; Surg Endosc 26: 2746-2750; 2012; 5 Pages.
The MathWorks, Inc .; "findpeaks" function; accessible online at: https://www.mathworks.com/help/signal/ref/findpeaks.html; accessed: Apr. 3, 2024; 26 pages.
Hauschildt et al., "Heart Rate Variability in Response to Affective Scenes in Posttraumatic Stress Disorder"; Biological Psychology 88 (2011); Aug. 2011; pp. 215-222 (8 pages).
Heater et al., "Google's Soli Radar Returns to Track Sleep on the New Nest Hub"; Tech Crunch; Mar. 2021; accessible online at: https://techcrunch.com/2021/03/16/googles-soli-returns-to-track-sleep-on-the-new-nest hub/; 11 pages.
Seo et al., "Stress and EEG"; InTech; ResearchGate; Mar. 2010; 15 pages.
Shimano, et al.; "Video Temporal Super-Resolution Based on Self-Similarity"; ACCV 2010; Part I, LNCS 6492; pp. 93-106; 2011; 14 Pages.
Simic, et al.; "Exam Experience and Some Reactions to Exam Stress"; ISSN 0362-1197; Human Physiology; vol. 38; No. 1; pp. 67-72; Jun. 20, 2011; 6 Pages.
Stoet; "PsyToolkit: Software Package for Programming Psychological Experiments using Linux"; Behavior Research Methods; vol. 42 (4); pp. 1096-1104; 2010; 9 Pages.
Stoet: "PsyToolkit: A Novel Web-Based Method for Running Online Questionnaires and Reaction-Time Experiments"; vol. 44; Issue 1; Nov. 15, 2016; 17 Pages.
Taelman, et al.; "Textile Integrated Contactless EMG Sensing for Stress Analysis"; Proceeding of the 29th Annual International Conference of the IEEE EMBS; Aug. 23-26, 2007; 4 Pages.
Shi, et al.; "Personalized Stress Detection from Physiological Measurements"; 2010; 5 Pages.

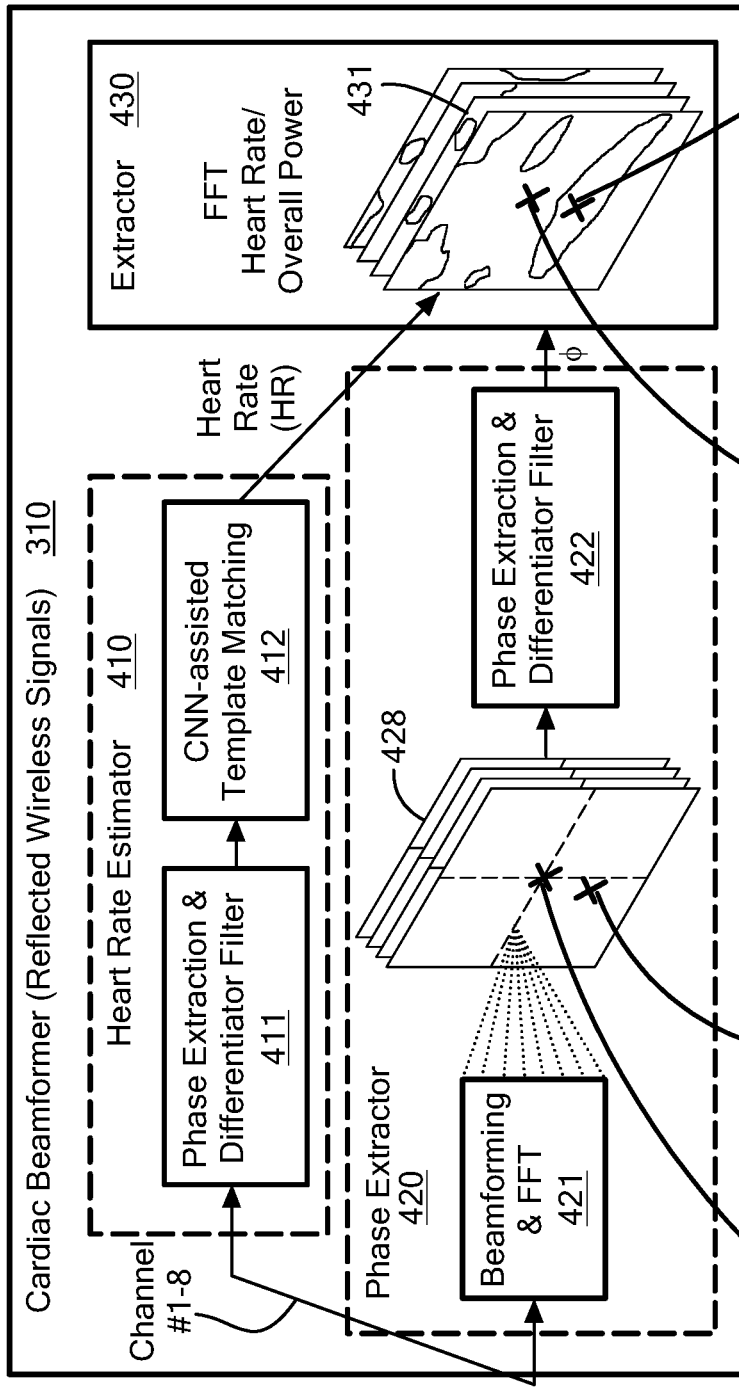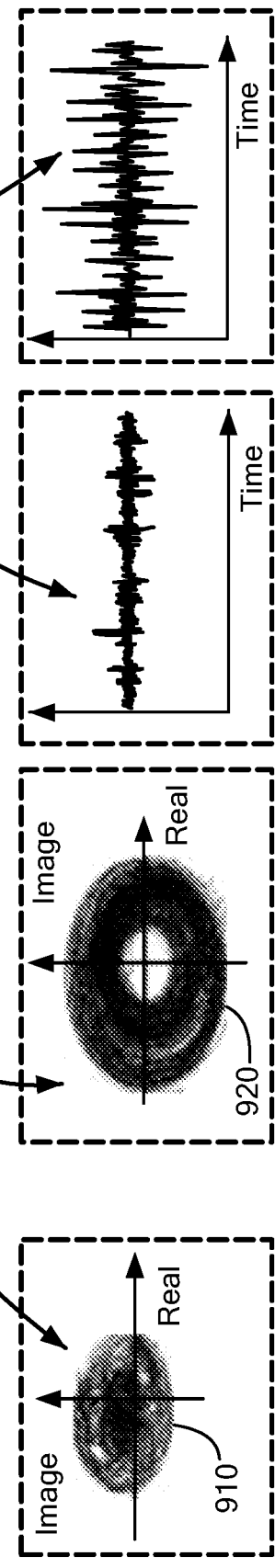

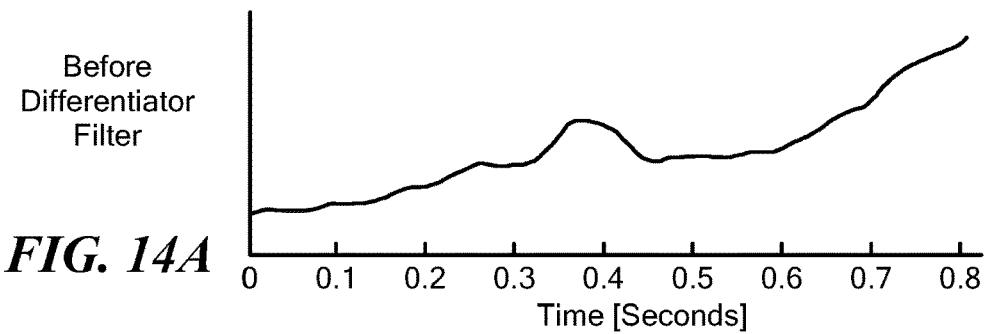
FIG. 14A — Before Differentiator Filter
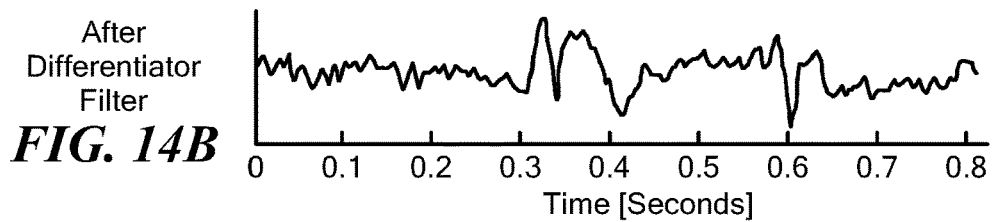
FIG. 14B — After Differentiator Filter
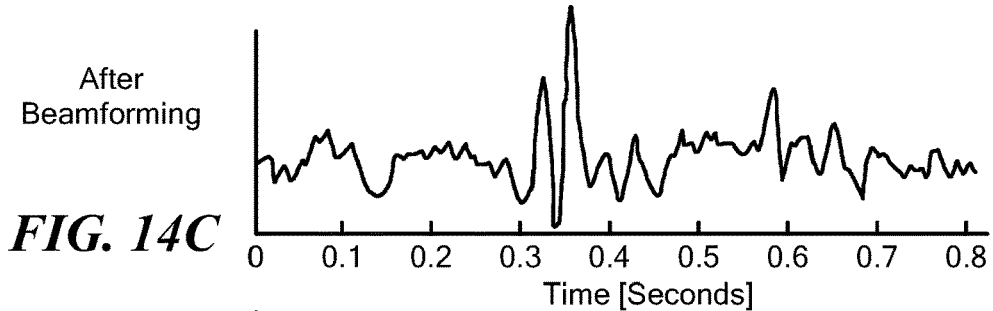
FIG. 14C — After Beamforming
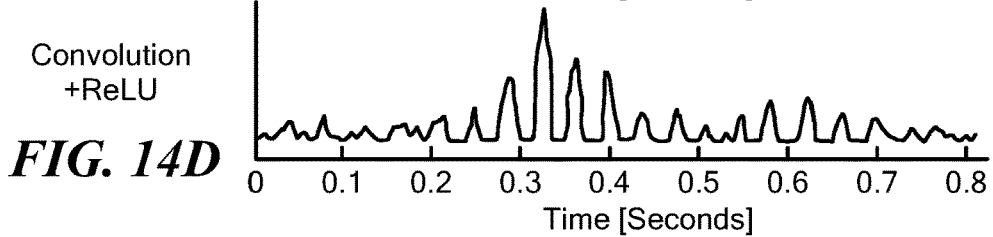
FIG. 14D — Convolution +ReLU
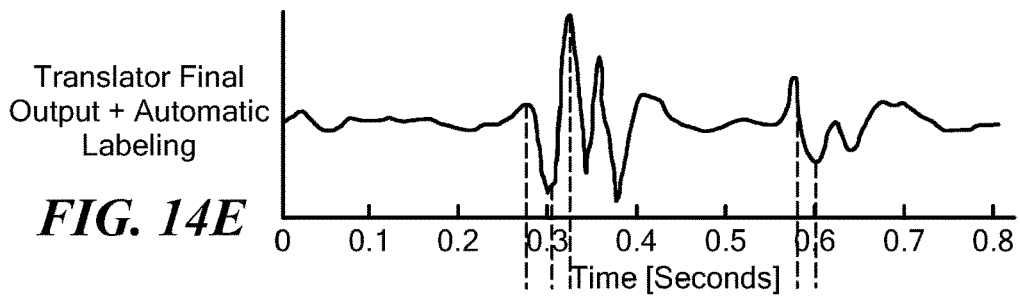
FIG. 14E — Translator Final Output + Automatic Labeling
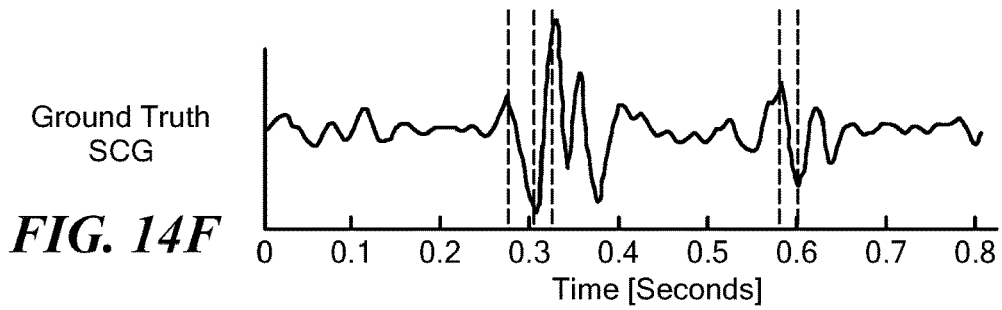
FIG. 14F — Ground Truth SCG

CONTACTLESS SEISMOCARDIOGRAPHY

CROSS REFERENCE TO RELATED APPLICATIONS

This application is a National Stage Entry of International Application No. PCT/US2021/047876, filed Aug. 27, 2021, which claims the benefit of U.S. Provisional Application No. 63/075,432, filed Sep. 8, 2020. The entire contents of these applications are incorporated herein by reference.

STATEMENT REGARDING FEDERALLY SPONSORED RESEARCH

This invention was made with government support under CNS-1739723 awarded by the National Science Foundation. The government has certain rights in the invention.

FIELD

One or more embodiments described herein relate to physiological monitoring.

BACKGROUND

As is known in the art, seismocardiography (SCG) is a technique for detecting mechanical activity of the heart by detecting vibrational signals caused by the heart and which propagate through the chest. The mechanical activity may include cardiovascular events, such as the opening and closing of heart valves and the contraction and relaxation of heart chambers. As is also known, the detected vibrational signals (a/k/a seismocardiography signals) may be recorded and represented as a plot referred to as a seismocardiogram. Thus, a seismocardiogram is a recording, often in the form of a plot, of the mechanical activity of the heart detected via vibrational signals of the heart which propagate through the chest (i.e detected via. SCG).

A variety of methods and systems have been used to generate SCG signals. One approach involves attaching bulky and cumbersome equipment (e.g., an accelerometer, electrocardiogram leads) to a patient to measure chest wall vibrations. Due to the sensitive nature of the required equipment, such an approach may require specialized handling and thus may need to be performed by a specialized practitioner in a calibrated medical setting or other controlled environment. SCG signals resultant from such measurements may be processed to diagnose cardiovascular conditions including myocardial infarction (e.g., heart attack), coronary heart disease, arrythmia, and ischemia. Thus, existing SCG systems and techniques are intrusive, inconvenient and may require administration by specialized practitioners operating in a calibrated medical setting or other controlled environment.

Moreover, such SCG systems and methods are unable to accurately detect so-called micro-vibrations embedded in heartbeat signals. (Micro-vibrations may be sub-centimeter vibrations in the human body or on the surface of the body that are induced by cardiovascular events, including the heart valve activities). As a result, information indicative of developing or present cardiac anomalies may go undetected.

SUMMARY

A variety of embodiments are disclosed for acquiring and automatically labeling seismocardiography (SCG) signals in a contactless manner using deep-learning techniques.

In accordance with the concepts, systems, devices and techniques described herein, a system for wireless generation of seismocardiography signals is described. In embodiments, a system for wireless generation of SCG signals includes an antenna having at least two transmit-receive antenna element pairs, a transmitter coupled to provide signals to the antenna, a receiver circuit configured to receive signals from the antenna, a cardiac beamformer coupled to receive signals from the receiver circuit, the cardiac beamformer comprising a phase extractor configured to extract phase information from time-domain signals output from the receiver circuit, the phase information corresponding to one or more regions in a surrounding environment, and a heart signal extractor comprising a convolutional neural network (CNN) configured to receive signals from the receiver circuit and in response thereto, generate an estimated heart signal.

In accordance with one or more embodiments, a system include a wireless transmit and receive circuit comprising one or more transmit antenna elements and one or more receive antenna elements, at least two transmit-receive antenna element pairs configured to receive wireless reflections derived from a heart; and a cardiac beamformer comprising a phase extractor configured to extract phase information from time-domain signals output from the at least two transmit-receive antenna element pairs, the phase information corresponding to one or more regions in a surrounding environment, and a heart signal extractor comprising a convolutional neural network (CNN) configured to receive signals from the at least two transmit-receive antenna element pairs and in response extract an estimated heart signal.

In accordance with one or more embodiments, a wireless-to-seismocardiogram translator comprising a receiver configured to receive wireless signals derived from a heart; and at least one processor configured to implement a machine-learning model to translate the wireless signals to a seismocardiogram.

In accordance with one or more embodiments, a method for automatically labeling a cardiac event includes receiving unlabeled time-series data output from a translator, the unlabeled time-series data based on wireless signals derived from a heart and the translator configured to translate the wireless reflections into a seismocardiogram; determining a feature of the time-series data; implementing a machine-learning model to compare the feature to a reference corresponding to a fiducial point, the fiducial point correlated to a health state; determining existence of the health state based on a result of the comparison; and automatically labeling the seismocardiogram to indicate the health state.

In accordance with one or more embodiments, a contactless seismocardiography system comprising a wireless transmit and receive circuit comprising one or more transmit antenna elements and one or more receive antenna elements, the wireless transmit and receive circuit configured to receive signals from at least two transmit-receive antenna element pairs; a cardiac beamformer configured to receive input signals from the wireless transmit and receive system, wherein the input signals correspond to wireless signals reflected from a human heart, the cardiac beamformer configured to process the input signals to provide a beamformer output signal; a wireless-to-seismocardiogram translator configured to transform the beamformer output signal into a seismocardiogram recording; and an automatic labeler configured to extract timing of one or more micro-cardiac movements of the human heart and to automatically label the SEISMOCARDIOGRAM recording corresponding to the one or more micro-cardia movements.

In accordance with one or more embodiments, a translation filter includes an input layer configured to receive time-series data; and a plurality of convolutional neural network (CNN) layers, each of the plurality of CNN layers grouped with a rectified linear unit (ReLU) function, a batch normalization (BN) layer, and a dropout layer.

In accordance with one or more embodiments, a contactless sensor includes a radar detector configured to detect reflected signals from a heart; a system configured to implement a machine-learning model to generate a seismocardiogram based on the reflected signals, the machine-learning model configured to modify a transformation function that converts the reflected signals to information in the seismocardiogram that corresponds to one or more micro-cardiac events; and labeling logic configured to implementing a deep-learning model to correlate at least one chest vibration to one or more micro-cardiac events based on the information in the seismocardiogram, wherein the reflected signals include wireless signals.

In accordance with one or more embodiments, a method for auto-labeling a cardiac event in a motion-based contactless measurement of a human heart, the method comprising encoding unlabeled seismocardiogram signals from at least one channel to signals with a predetermined number of sample points and multiple channels; and decoding the encoded signals to labeled seismocardiogram signals which have same data points as the unlabeled signals and a channel size of micro-cardiac events.

BRIEF DESCRIPTION OF THE DRAWINGS

FIG. 4 is a block diagram of an illustrative embodiment of a cardiac beamformer.

FIGS. 9A and 9B are plots of time-domain signals projected onto complex planes.

FIGS. 9C and 9D are plots of voltage vs. time for example heat maps such as may be generated by an embodiment of a calculator.

FIGS. 14A-14F are a series of plots illustrating example waveforms generated by various stages of a contactless sensor which may be the same as or similar to the contactless sensor of FIG. 1.

DETAILED DESCRIPTION

Embodiments described herein provide a system and method for generating seismocardiography (SCG) signals using deep-learning techniques. The SCG signals are acquired using a sensor that transmits wireless signals to and detects reflected signals from the heart of a patient in a contactless manner during a use or monitoring mode. The reflected signals are analyzed to satisfy the requirements of a variety of applications, including, but not limited to, generating seismocardiograms including seismocardiograms having labeled cardiac events useful in monitoring and diagnosing patient health. These and other concepts, systems, devices, techniques and example applications are discussed below.

Figure 1:
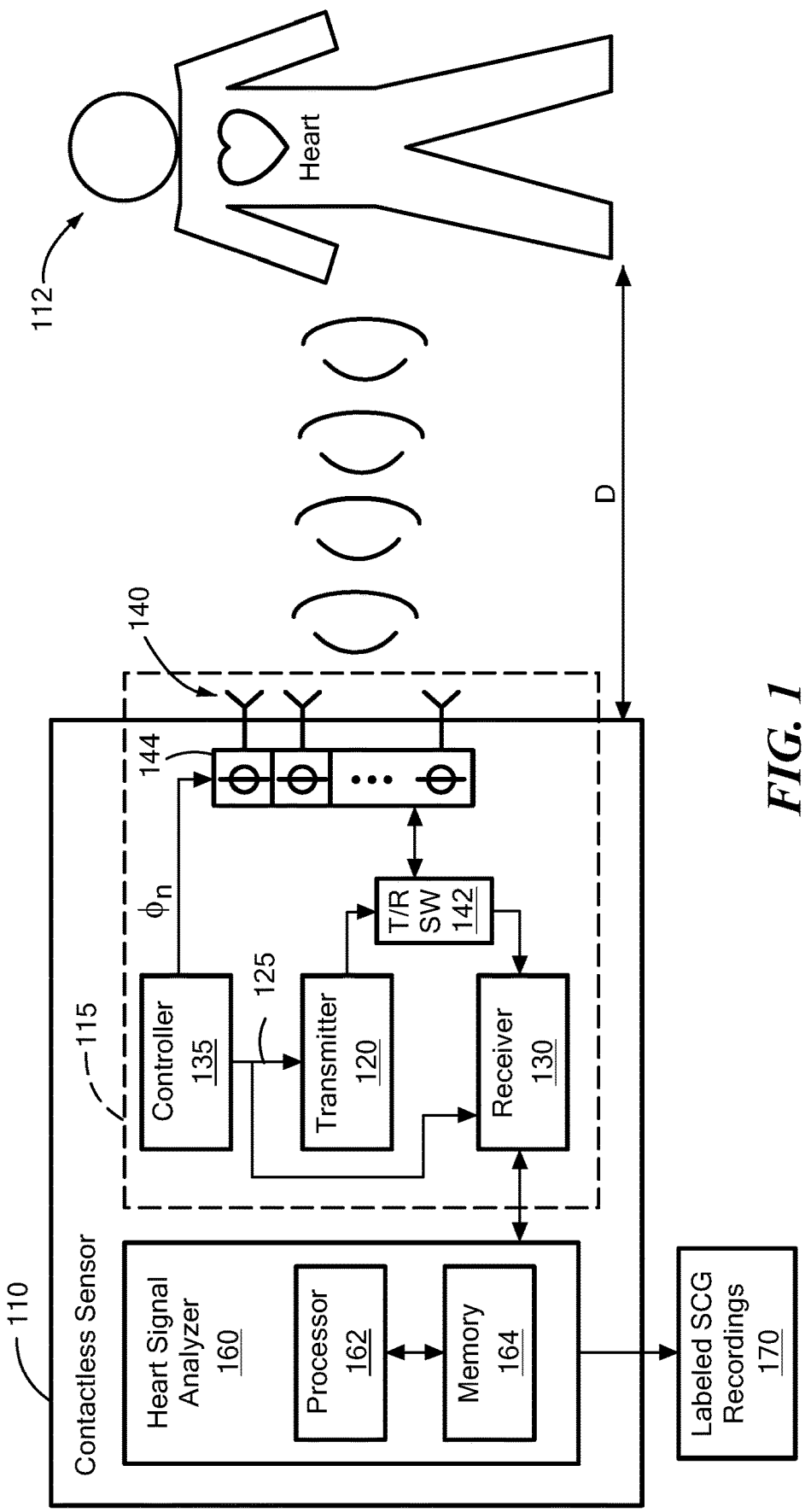
FIG. 1 is a block diagram of an illustrative contactless sensor.

FIG. 1 shows an embodiment of a contactless sensor 110 for generating seismocardiography (SCG) signals. Contactless sensor 110 is positioned a distance or range D from a patient 112 to be monitored. The exact distance D need not be known, but rather may lie within a predetermined range. In some embodiments, a known D which does not substantially vary may provide for more accurate results. In practical terms, the value of D will change over time because of breathing and heart movements. An example of D may be 25-50 cm in a direction facing the chest, however a different range of distances may be used in other embodiments.

Referring to FIG. 1, the contactless sensor 110 includes a wireless transmit and receive system 115 which emits signals toward a person (in particular toward a person's heart) and receives reflected signals therefrom. The transmit and receive system comprises a transmitter 120, a receiver 130, a controller 135 and an antenna 140. In this example embodiment, antenna 140 is illustrated as a single antenna shared between the transmitter and receiver. Thus the system includes a transmit/receive switch (T/R switch) 142 coupled between the antenna and the transmitter and receiver so as to isolate transmit signals from receive signals.

It is noted that although a T/R switch is shown in the example embodiment of FIG. 1, devices other than a T/R switch may be used (including but not limited to passive devices such as types of circulators or active devices). It should also be appreciated that in embodiments the transmit and receive system may include separate transmit and receive antennas in which case it may not be necessary to include a T/R switch, isolator or any type of signal isolating device.

Controller 135 is coupled to the transmitter 130, receiver 150 and antenna 140 an may be configured to generate information for controlling transmission of wireless signals to an area proximate the heart of the patient, e.g., the sternum including characteristics of the transmit signal (e.g. including, but not limited to transmit frequencies, timing of the transmit signals) and phasing of the antenna elements (via phase circuits 142).

The wireless signals may be radio frequency (RF) signals, acoustic signals, or ultrasonic signals. In embodiments when acoustic signals or ultrasonic signals are used, antenna 140 corresponds to an appropriate transducer.

Example embodiments in which RF signals are used will be discussed below. Irrespective of the type of wireless signals used or the wavelength of transmit-receive signals used by sensor 110, the controller 135 may output various parameters 125 that determine how the transmitter is to transmit the signals. The parameters may include power, pulse width, frequency, carrier wave information, modulation information, signal format, and/or other parameters.

When the wireless signals are RF signals, the transmitter 120 emits such RF signals via antenna 140. For example, the transmitter 120 may generate the RF signals in a predetermined pattern (e.g., with one or more predetermined phase shifts or delays) relative to one another that conform to the configuration of the antenna transmit and receive elements. (Of course, in an acoustic or ultrasonic embodiment, the transmitter may be replaced with one or more directional speakers or other type of transducer and the contactless sensor 110 may be considered to be a sonar sensor).

The transmitted signals (e.g. RF or other signals) may be specifically designed to optimize detection of reflected signals from the heart. In embodiments, the separation distance D may be taken into account. In one embodiment, the RF signals may lie within a predetermined wavelength range. For example, the RF signals may be in the millimeter wave (mmW) frequency range, microwave (µW) frequency range, or in other frequency (or wavelength) range. For illustrative purposes only, and with no intent to limit the scope of the embodiments described herein, the sensor 110 will be discussed as a radar sensor.

Irrespective of the type of signal or the wavelength of transmit-receive signals, the wireless signals may be sufficient to penetrate clothes of a patient (e.g. patient 112) and reach/penetrate the skin (so as to detect vibrational signals caused by the heart), thereby making use of the contactless sensor 110 suitable while the patient is wearing clothes.

System 110 further comprises a heart signal analyzer 160 which comprises a processor 162 and a memory 164 having instructions and/or data stored therein. As will be described in detail below, heart signal analyzer 160 implements one or more models for processing the reflected signals received from the detector. Heart signal analyzer 160 receives detected signals from receiver 130 and applies the models to the received signals.

In contrast to conventional SCG techniques, detection of heart operations via transmission and reception of wireless signals in system 110 alleviates the need of having to physically attach a device or apparatus to the chest or other body part of a patient during use or sensing mode.

System 110 has at least two modes: a use node and a training mode. Prior to operating system 110 in a use mode, the system 110 may be calibrated in a training mode. models are trained. In training mode, reference data may be generated by an accelerometer or other equipment attached to the chest, or stored information may be used as the reference data. Such reference data may be used to train models used by heart signal analyzer 160.

During a use or monitoring mode (e.g., when used in the field by a patient in a stand-alone setting or by a consumer, medical personnel, or other person in a real-world application), the system 100 may be used in a completely contactless manner (i.e., the accelerometer is not needed and heart monitoring may be performed solely based on reflections of the transmitted wireless signals detected from the heart).

In one embodiment, the wireless signals may be frequency modulated continuous wave (FMCW) RF signals directed toward and reflected from an area of the patient proximate the heart (e.g., the chest area of the patient). In one embodiment, contactless (radar) sensor 110 may transmit the FMCW signals by radiating continuous transmission power and changing its operating frequency during measurement. Generating SCG signals using FMCW signals may be beneficial in various applications. In other embodiments, RF signals other than FMCW signals may be used including CW signals.

In embodiments, antenna 140 may be provided as part of (e.g. integrated with) the contactless sensor 110. In embodiments, antenna 140 may be separate from transmit-receive system 115. Also, as noted above, antenna 140 may be provided having various configurations. In one embodiment, antenna 140 may be provided as a one-dimensional array of N directionally controlled antenna elements 141, where N≥2. In another embodiment, the antenna may be provided as a two-dimensional array of directionally controlled antenna elements. The antenna elements may be shared as transmit-receive pairs. In some implementations, e.g., one or more transmit elements may be shared, one or more receive elements may be shared, or one or more transmit elements and one or more receive elements may be shared.

Each array of transmit elements may, for example, be coupled to its own transmitter and controlled by control signals from the controller 135 or other appropriate controller (e.g. in the case where a plurality of transmitters and/or a plurality of receivers are used, each transmitter and/or may have an associated controlled. For illustrative purposes, only one transmitter 120, receiver 130 and controller 135 is shown in FIG. 1 with the understanding that additional transmitters, receivers, controllers may be included based upon a variety of factors including, but not limited to whether a one-dimensional or multi-dimensional configuration of antenna elements is used to implement the antenna. In one implementation, the transmit antenna elements in each array may receive respective phase-shift (φ) control information provided to phase-shifter 141 from the controller 120, to form a phased-array radar transmitter.

A detection section of the contactless sensor includes receiver 130 and heart signal analyzer 160. As described above, receiver 130 is coupled to the antenna 140. In embodiments, receiver 130, controller 135 and antenna 140 operate to implement beamforming techniques to detect and process wireless signals that reflect off the chest of the patient.

In embodiments, the number of receivers (or more generally detectors) in the sensor may correspond, for example, to the number of arrays in the antenna array 140. In embodiments, a single common detector coupled to all antenna elements may be used for this purpose. In one embodiment, the sensor may have a one-dimensional array of transmit antenna elements and an N-dimensional array of receive antenna elements, where N>1. In this case, the sensor may be said to have a one transmitter, N receiver (1T, NR) arrangement. In another embodiment, the sensor may have an N-dimensional array of transmit antenna elements and a one-dimensional array of receive antenna elements. In this case, the sensor may be said to have an N transmitter, one receiver (NT, 1R) arrangement. In any event, the number of transmit-receive pairs may be more than one. Operations of the detector(s), or receiver(s), will be explained based on the assumption that the transmitted and reflected signals are wireless signals in the millimeter wave range, but the reflected signals may be in another wavelength range in another embodiment.

As noted above, heart signal analyzer 160 implements one or more models for processing the reflected signals received from the detector. In one embodiment, the heart signal analyzer includes one or more deep-learning models that are configured in a training mode and then operated in a use or monitoring mode. The heart signal analyzer 160 applies the model(s) to detect cardiac micro-vibrations (or other indicia of cardiac activity) which may relate to certain health conditions. In this type of medical application, the reflected signals are translated (or transformed) into a seismocardiogram 170, that may be analyzed (e.g., labeled and/or subsequently processed) to determine the health conditions. However, this application is just one of many possible applications and is not intended to be and should not construed to be limiting of the scope of the concepts, systems, device and techniques and embodiments described herein. Example embodiments of the heart signal analyzer 160 and its methods of operation are described in greater detail below.

In operation, transmitter 120 transmits wireless signals toward a target area corresponding to the heart of a patient. The receiver 130 detects wireless reflections from the heart and, in one embodiment, provides such received signals to the heart signal analyzer 160 to extract phase information, which, for example, may be determined based on Equation (1):

$$q5(t) = 2\pi \frac{d(t)}{\lambda} \quad (1)$$

in which:
λ is the wavelength of the transmitted signal;
d is the distance between the contactless sensor 110 and the body of the patient;
t is time; and
d(t) is the distance as a function of time. In one embodiment, the distance d(t) may be the distance between the antenna to the sternum. In another embodiment, d(t) could be the distance between some other location on the chest and the antenna. As previously described relative to D, d(t) may be a function of time due to the movement (e.g., vibrations) of the sternum of the patient, but practically may also include other noise and interference which may be rejected by filtering.

In some embodiments, the wavelength A of the transmitted signal may be in the millimeter range, but other wavelengths may be used as previously discussed. The distance d may be a predetermined or known distance from the patient. For example, the patient may remain relatively static during detection and a predetermined distance away from the contactless sensor, e.g., within a quarter to a half a meter. While d(t) may change as a function of time as indicated above, generally except for movements of the chest (e.g., approximately 5 mm scale or less), the patient is expected to be still and thus in a fixed position. Thus, the predetermined or known distance from the patient may be understood to be a quasistatic distance (e.g., sitting on a chair, standing still) that is generally fixed distance except for the small movements of the chest as explained.

The distance d may be selected in accordance with a variety of factors, including, but not limited to, transmitter power, noise conditions, the type of signal being transmitted (e.g. RF, ultrasound, sonar).

Since cardiac activity (e.g., opening and closing of heart valves, etc.) may result in chest wall vibrations (e.g. small or micro-vibrations on the chest wall). Such chest wall vibrations may affect or serve as a basis for setting the distance d between the sensor and the body of the patient. These vibrations result in changes in the phase of signals reflected from the chest wall. Such signals are received by the receiver. Thus, the vibrations may be determinable from the phase information in the reflected signals, in the process of recording SCG signals.

In one embodiment, the reflected signals are intercepted via a two-dimensional array antenna having horizontal and vertical antenna element. Each of the antennas elements have an associated phase setting. Signals reflected from the patient are received via the antenna, coupled to the receiver and provided to a beamformer portion of the heart signal analyzer. Details of the beamformer are discussed in greater detail below. Briefly, however, the beamformer forms beams from the wireless signals reflected from the heart. When the transmitted radar signals are FMCW signals, reflections coming from different wavelength or frequency ranges may be sorted (or isolated) into different bins (or buckets), thus resulting in detections of chest wall vibrations which are more accurate than those detected using prior art techniques. Thus, use of FMCW radar signals may prove to be more suitable than other forms of signals for some applications.

Thus, the transmitter 120, receiver 130, antenna 140, and heart signal analyzer 160 together form a uniquely designed contactless sensor. In some applications, the sensor may be included in a smartphone, tablet, notebook computer, or other types of consumer electronics. One non-limiting example would be to provide the sensor 110 as a radar sensor and incorporate the radar sensor 110 into the low-cost, millimeter-wave radar-based system corresponding to the Motion Sense application of the Google Pixel 4 smartphone.

However, this is just one example. In other embodiments, it may be desirable to use a different radar-based sensor system.

The heart signal analyzer 160 includes one or more processors 162 and a memory 164. Only one processor is shown for illustrative purposes. The processor 162 executes instructions (e.g., software, firmware, etc.) stored in the memory 164 for performing the operations used to generate intermediate and final results output from the sensor. When executed by the processor 162, the instructions may implement various models and/or algorithms for generating a seismocardiogram 170 (which may or may not be labeled) or other output of the intended application. In some embodiments, the processor 162 and controller 135 may be the same processor, but they may operate independently or interdependently in other embodiments.

In operation, the heart signal analyzer 160 processes the wireless reflected signals to generate information (e.g., waveforms, etc.) containing embedded cardiac-related information across a predetermined spectrum. As will be discussed in greater detail below, the cardiac-related information includes, for example, indications of cardiovascular events that may be identified as a way of assessing the condition of the patient or other indicia of health status.

In one embodiment, the heart signal analyzer 160 may implement a hybrid processing architecture that logically combines one or more of extraction, filtering and other techniques with deep-learning models to robustly process SCG signals and generate seismocardiogram recordings from the detected reflections. In one embodiment, the hybrid processing architecture may perform a series of spatio-temporal filtering operations that capture the physics of RF propagation and incorporate constraints from heart physiology.

As indicated, one possible output of the heart signal analyzer 160 may be a seismocardiogram 170 or its underlying signals. In some embodiments, the seismocardiogram 170 may be automatically labeled with identified cardiac metrics, a function that may be performed by an automatic labeler of the system in a manner described below.

Figure 2:
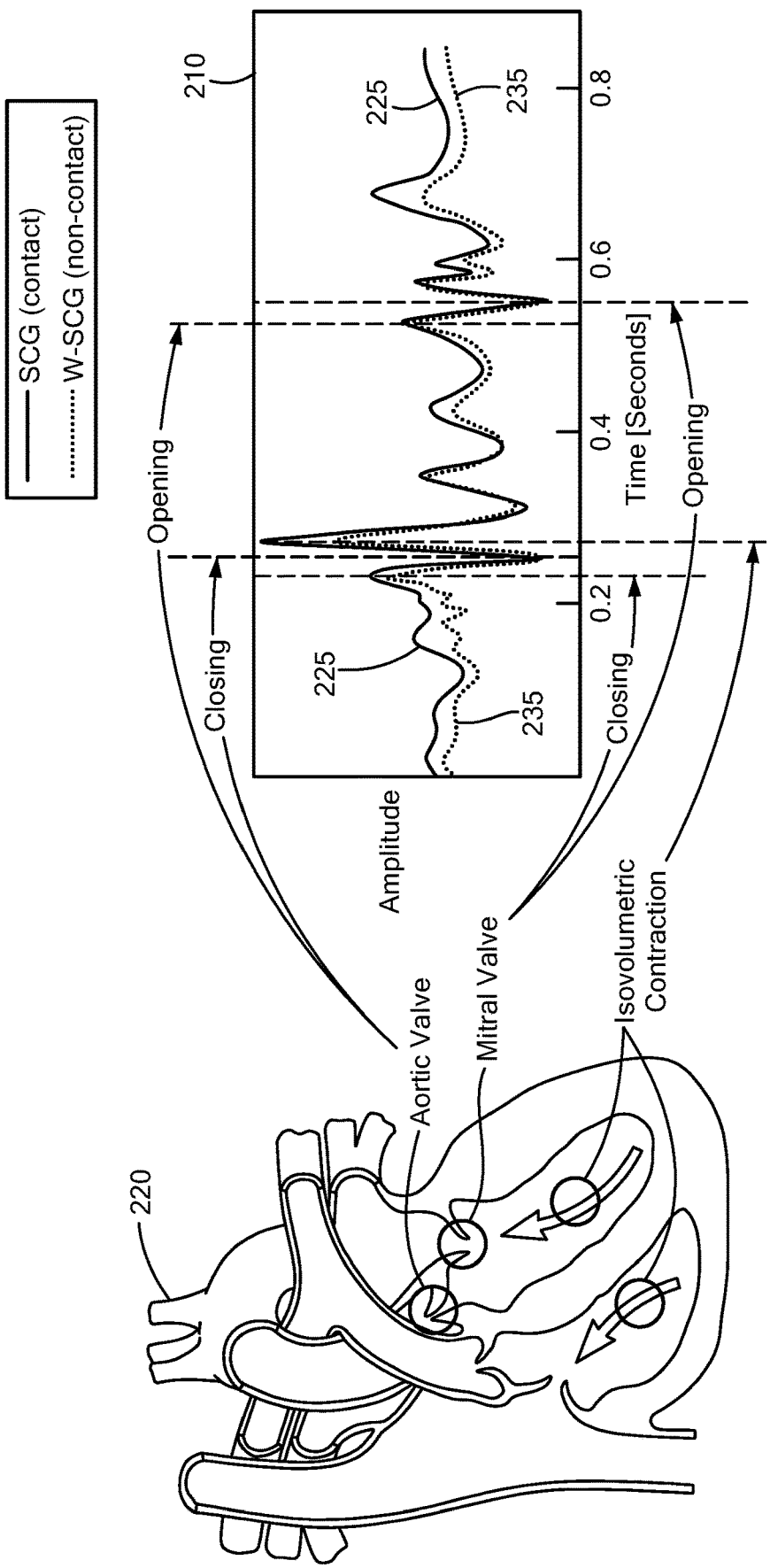
FIG. 2 is a plot of voltage vs time of a labeled seismocardiogram recording having portions labelled to identify to heart actions.

FIG. 2 shows an example seismocardiogram recording 210 that may be generated in accordance with a contactless sensor system which may be the same as or similar to the system described in conjunction with FIG. 1. In FIG. 2, a correspondence is drawn between the seismocardiogram recording 210 (or more simply seismocardiogram 210) and a heart 220 for improved understanding, and more particularly between the seismocardiogram and the aortic valve, mitral valve, and isovolumetric pathways over a heartbeat period.

Referring to FIG. 2, the seismocardiogram 210 includes two waveforms. The first waveform 225 (the solid curve) corresponds to a single heartbeat obtained with contact, i.e., from an accelerometer strapped to a person's body proximate an apex of the heart. This waveform is provided for reference purposes. The second waveform 235 (the dotted curve) corresponds to a single heartbeat obtained without contact (i.e. via a contactless sensor such as contactless sensor 110 described above in conjunction with FIG. 1) in a monitoring mode (after training). Thus, the second waveform is obtained in a contactless manner (e.g., without using an accelerometer or any other form of body contact) in a manner described herein. System 100 may also precisely time and label a predetermined number of micro-cardiac movements, information of which is embedded into the waveform 235.

The number of micro-cardiac movements may vary among embodiments, but in one embodiment up to the following five micro-cardiac movements may be precisely timed and automatically labeled by sensor 100: opening and closing of the aortic valve, opening and closing of the mitral valve, and isovolumetric contraction (of the ventricles). In FIG. 2, these movements (or events) are labeled and correspond to the dotted vertical lines and arrows showing correspondence with the heart.

Figure 3:
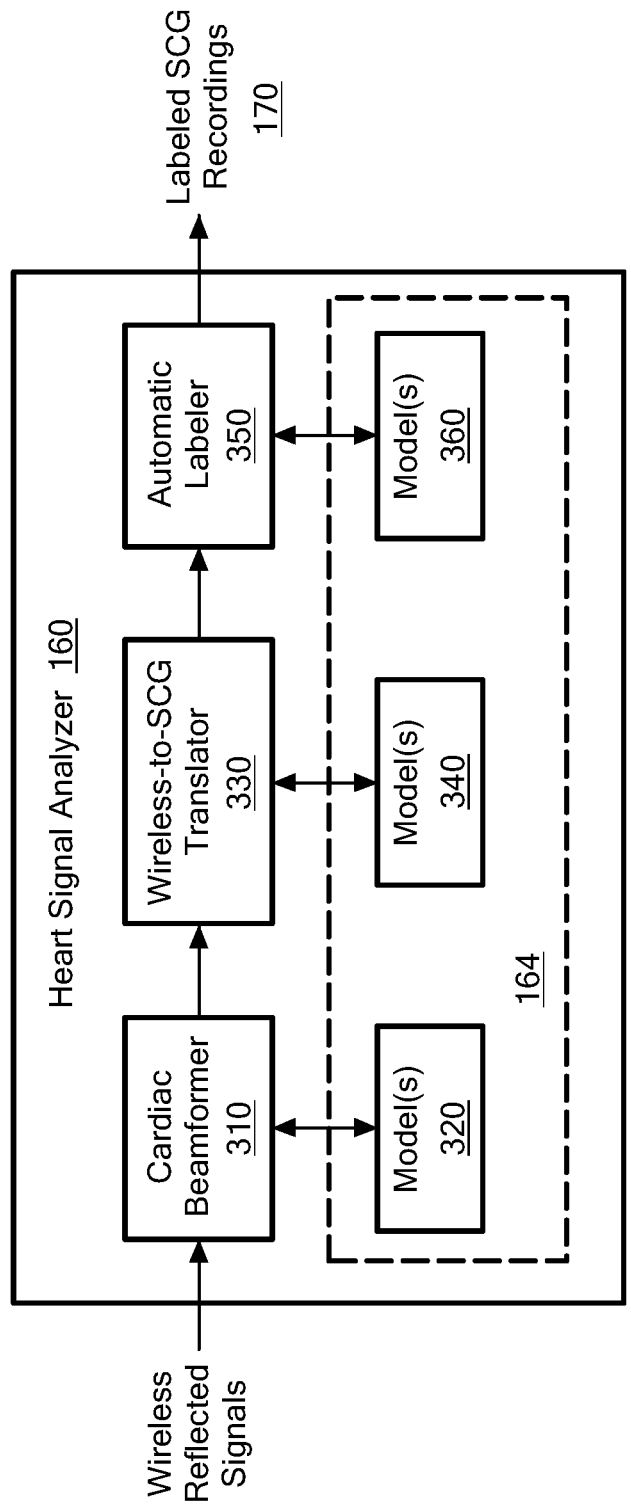
FIG. 3 is a block diagram of an illustrative embodiment of a heart signal analyzer.

FIG. 3 illustrates an example embodiment of the heart signal analyzer 160 which includes a cardiac beamformer 310, a wireless-to-seismocardiogram translator 330, and an automatic labeler 350. Although the cardiac beamformer is here shown as part of heart signal analyzer 160, in other embodiments, the beamformer may be at another location (e.g., in receiver 130). In some embodiments, the cardiac beamformer may be omitted. In these cases, the wireless signals (or reflection signals) may be input into the wireless-to-seismocardiogram translator of the heart signal analyzer 160. This may occur, for example, in a WiFi embodiment where, as the name indicates, the wireless signal includes WiFi signals The cardiac beamformer 310 focuses on reflections detected from one or more predetermined locations of the heart, e.g., from the apex of the heart. For example, the cardiac beamformer may process FMCW signals received via a two-dimensional (2D) array antenna in order to effectively perform beam steering, e.g., to detect reflected signals from the heart with improved (or maximum) signal-to-noise ratio (SNR). In one embodiment, the cardiac beamformer may be a four-dimensional (4D) beamformer, examples of which are described below. In other embodiments, the cardiac beamformer may be a beamformer different from a 4D beamformer.

In one embodiment, the cardiac beamformer may combine one or more three-dimensional (3D) filters with a time-domain convolutional neural network (CNN) to determine the (e.g., 3D) location of the heart, while estimating the heart rate. The cardiac beamformer 310 may also filter out noise and interference in space and time. These and other operations (including implementation of the model(s), extraction, filtering, and other operations) may be performed based on execution of the instructions stored in a memory 220 and executed by processor 162.

The wireless-to-seismocardiogram translator 330 may receive information output from the cardiac beamformer (e.g., 3D location of the heart, heart rate, and phase as well as other information). In embodiments where the cardiac beamformer is omitted, wireless reflected signals from the detector may be input (e.g., directly) into the wireless-to-seismocardiogram translator 330.

The wireless-to-seismocardiogram translator 330 may perform machine-learning technique(s) based on this information in order to generate seismocardiogram recordings. In one embodiment, during a training mode, the wireless-to-seismocardiogram translator may generate seismocardiogram recordings based on the detected reflections from the heart and reference information. The reference information may include, for example, seismocardiogram recordings obtained from an accelerometer attached to the patient. (In some embodiments, the term "reflection" and variations thereof may be considered synonymous with "reflected signal" and variations thereof). For example, the machine-learning model may be initially trained with one or more sample sets of data to form a transformation (or translation) function for the translator 330. The transformation (or translator) function may then be used as a basis for generating the seismocardiogram recordings. Based on the training data, the transformation function may converge towards (or "learn") a function that produces an accurate representation of the SCG signals of the patient.

More specifically, in one embodiment, the transformation function may be generated based on the fact the radar reflections (used in system 100) and accelerometer measurements (e.g., used to formulate baseline seismocardiogram recordings) capture chest vibrations that arise from the same underlying micro-cardiac events. Hence, during training, the translator 330 may use recordings from the accelerometer attached to the patient (e.g., apex of the heart) to develop, or "learn," the transformation function of a model based on detected radar reflections and the reference seismocardiogram recordings. In one embodiment, the reference information may be archived information previously stored for the patient or may be general baseline information unrelated to the particular patient being monitored.

Once the transformation function has been trained, the Wireless-to-seismocardiogram translator 330 may generate a seismocardiogram recordings for the patient in monitoring mode without using the accelerometer anymore. Instead, in one embodiment, the machine-learning model of translator 330 may use one or more learned translation filters to transform reflected signals from the patient to one or more seismocardiogram recordings. The model and its attendant transformation function may be generated in different ways in other embodiments.

In addition to these features, in one embodiment, the Wireless-to-seismocardiogram translator 330 may be implemented to isolate different sources of errors to develop a high accurate model. When implemented in this manner, the model may achieve a level of flexibility not possible with other arrangements, e.g., not possible by implementing an end-to-end model as a black box, which may be unsuitable for critical tasks such as cardiovascular monitoring. Additionally, in one embodiment the translator 330 may incorporate one or more spatio-temporal filters that correspond to domain knowledge relating to radar and signal processing. In such an example implementation, the training time and complexity of the deep-learning model architecture may be significantly reduced and its tuning parameters may be initialized with well-informed estimates, which, in turn, may allow it to converge at a faster rate and produce more accurate solutions during monitoring mode implemented after training. The Wireless-to-seismocardiogram translator may perform these and other operations (including implementation of the model(s)) based on instructions in stored in a memory 340 and executed by processor 162.

The Automatic Labeler 350 may automatically label the seismocardiogram recordings generated by the Wireless-to-seismocardiogram translator 330. In one embodiment, the automatic labeling may include extracting the timing of one or more fiducial points of interest, e.g., the timing of the following five fiducial points of interest may be extracted: (a) mitral valve closing, (b) isovolumetric contraction, (c) aortic valve opening, (d) aortic valve closing, and (e) mitral valve opening. A different number and/or type of fiducial point(s) may be extracted in another embodiment. To determine these points, the Automatic Labeler may modify and adapt a model to identify desired salient features in one or more images (e.g., seismocardiogram recordings), which features correspond to the fiducial points of interest.

In one implementation, the seismocardiograms may be one-dimensional (1D) seismocardiograms and the model may be a U-Net (e.g., Computer Vision) model. The seismocardiograms and models may be different in another embodiment. The Automatic Labeler 350 may perform these and other operations based on instructions in stored in a memory 360 and executed by processor 162. The memories 320, 340, and 360 may correspond to memory 164 (e.g., different regions in this memory) or may be memories that are separate from one another. The different features of the heart signal analyzer 160 will now be described in greater detail.

Cardiac Beamformer

The cardiac beamformer 310 takes a beam-steering approach to focus on detection of wireless signals reflected from the heart. This approach may be implemented, in part, using a model which is initially trained in training mode. Once trained, the cardiac beamformer is configured to operate in monitoring mode to generate a seismocardiogram (and/or other information) for the patient.

The cardiac beamformer 310 may initially determine the direction that has the strongest heart signal from the reflected signals. One approach in performing this operation is to generate an empirical basis which the Beamformer can use to determine exactly how and what the heart reflections look like. Over time, the reflections are likely to change depending on individual patient characteristics, patient position (e.g., how the patient is sitting), and heart rate. Moreover, the heartbeat signal itself may be masked by motion due to breathing and/or other forms of noise and spurious signals. The breathing motion and other forms of noise may present with a magnitude significantly larger than the micro-vibrations of cardiac movements. This may be compensated for, as described below.

To perform these and other operations, the cardiac beamformer may exploit the fact that the heartbeat signal is periodic and may then leverage this periodicity to identify the best direction of obtaining the corresponding periodic signal. In one embodiment, the cardiac beamformer may divide the operation of identifying the best beam with the heart rate into operations performed along two signal-processing chains.

FIG. 4 shows an embodiment of the cardiac beamformer 310 which includes the signal-processing chains. In this embodiment, the Cardiac Beamformer includes a heart rate extractor 410, a phase extractor 420, and a calculator 430. The heart rate extractor 410 corresponds to a first signal-processing chain and the phase extractor 420 corresponds to a second signal processing chain. The heart rate extractor 410 and the phase extractor 420 are shown to be implemented in parallel (e.g., simultaneously), but may be implemented sequentially in another embodiment. The calculator 430 is coupled to receive the outputs of the heart rate extractor and the phase extractor in order to generate the output of the cardiac beamformer.

The heart rate estimator 410 includes first logic 411 and second logic 412. The first logic 411 performs phase extraction operation and a filtering operation, e.g., corresponding to that of a differentiator filter. The second logic 412 implements template matching using deep-learning model. In one embodiment, the deep-learning model may be a one-dimensional convolutional neural network (CNN), but a different deep-learning model may be used in another embodiment. For convenience, the first logic 411 may be referred to as a phase extractor and filter, and the second logic 412 may be referred to as a template matcher.

Figure 5:
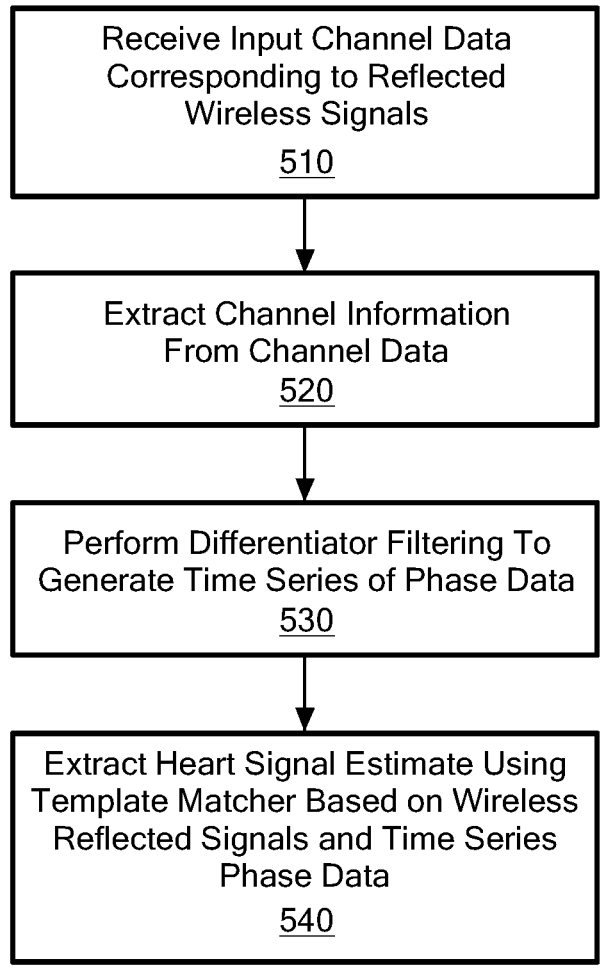
FIG. 5 is a flow diagram of an example method for performing heart signal estimation.

FIG. 5 illustrates an example method that may be implemented by the cardiac beamformer for generating its output. The operations of the method may correspond to functions performed by the heart rate estimator 410, phase extractor 420, and calculator 430, which will now be further explained. In accordance within one embodiment, the phase extractors described herein may be a one-dimensional (1D) phase extractor. In other embodiments, the phase extractors described herein may be multiple-dimensional (e.g., 2D or 3D) phase extractors.

Referring to FIGS. 4 and 5, at 510, the phase extractor and filter 411 receives input data corresponding to the wireless reflected signals output from the detector 150. The input data may include one or more time-domain signals (e.g., time-series data) including phase information, amplitude information, or phase and amplitude information received, for example, on a channel basis. These signals are detected from the output of antenna 140, which in this example embodiment includes a one-dimensional array of eight receive elements corresponding to a respective number of channels 1 to 8 (as labeled). A different number of antenna receive elements and channels may be used in another embodiment, with the understanding that the number of antenna receive elements and channels is two or more. The wireless reflected signals received on each of these channels may be expressed by Equation (2).

$$m_n = A_n \times e^{j\phi_n(t)} \quad (2)$$

where:
n is an index of a signal channel;
t is time;
A is an amplitude of a received reflected signal;
$A_n$ is an amplitude of a received reflected signal in the $n^{th}$ signal channel;
φ denotes a phase of a received reflected signal; and
$\phi_n(t)$ denotes the phase of a received reflected signal in the $n^{th}$ signal channel as a function of time.

At 520, once the input data is received, the phase extractor portion of logic 311 extracts the phase φn(t) from the channel data. This may be accomplished, for example, by extracting the phase φn(t) from the phase information or phase and amplitude information of the time-series data (e.g., time-domain signals) received from the channels.

At 530, a filtering function may be performed. For example, the filtering section of logic 411 may implement a differentiator filter that serves at least two purposes. First, the filter may suppress low-frequency respiration signals in the channel input data and boost the high-frequency heart rate. This filtering operation may be performed in simultaneously with the phase extraction and may accentuate feature points related to micro-cardiac movements. Second, the differentiator filter may transform the phased-based distance estimate to an acceleration by designing the filter to operate as a second derivative. Through these operations, the phase extractor and filter 411 outputs a filtered time series of phase data. In some applications, these filtering operations may allow the CNN-assisted Template Matcher 412 to more easily derive a histogram from the channel data and to obtain a representative heart rate, as described below.

At 540, the Template Matcher 412 extracts heart signal information (e.g., heart rate, heart period, etc.) from the wireless reflected signals based on the filtered time series of phase data output from the phase extractor and filter 411. In one embodiment, the Template Matcher may perform this operation by formulating an estimation problem as a 1D CNN matching problem. In performing template matching, the learned template T may be extracted that matches a repetitive sequence. The learned template may be a best or optimal template or a template that at least satisfies one or more predetermined error criteria. (The template may be considered a sliding convolutional window loaded with an initial waveform of interest. The initial waveform may then be convolved with the reflected waveform by sliding the window and then the waveform may be corrected. This process may be iteratively performed until there is convergence to a best estimate of the template.)

In one embodiment, the learned template T may correspond to a single heartbeat interval, and the repetitive sequence may be the filtered time series of phase data obtained from the wireless reflections by the phase extractor and filter 411. This may be achieved, for example, by reducing or minimizing the error e(i) between the template T and repeating segments of the input Data D based on Equation (3):

$$e(i) = |Di - T|^2 = |Di|^2 + |T|^2 - 2|Di*T| \quad (3)$$

where Di is the $i^{th}$ segment of the input time-series data which has the same size as T, and * denotes the cross-correlation operation. By reducing or minimizing the above error function, the template T may be recovered and thus the heartbeat template may be learned, as well as the heartbeat period. From this information, the heart rate for the patient may be determined.

In one embodiment, the above optimization problem may be solved using, for example, stochastic gradient descent (SGD) or another iterative method. To efficiently solve SGD using computing tools, the SGD may be formulated as a convolutional neural network (CNN) as previously mentioned. In one embodiment, according to Equation (3), the error function e(i) can be reduced or minimized by maximizing the convolution |Di*T|, while reducing or minimizing T. This may be solved by learning, for example, the optimal convolution filter T while training the neural network to reduce or minimize an appropriate loss function, e.g., by reducing or minimizing the error of Equation (3).

FIGS. 6A to 6E show examples of different signals that may be generated to perform CNN-assisted template matching during training mode. FIGS. 7A and 7B show an embodiment of a method that may be used to perform template matching, operations of which may correspond to those set forth in FIGS. 6A to 6E.

Figure 6A:
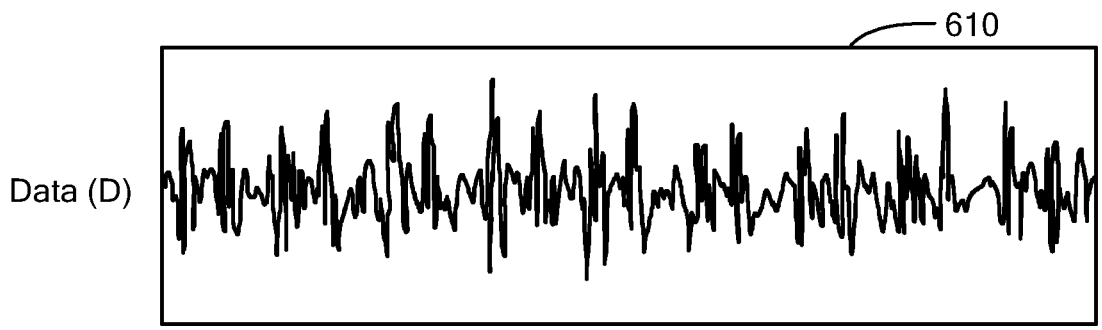
FIGS. 6A-6E are a series of plots of an example process for template matching.
Figure 7A:
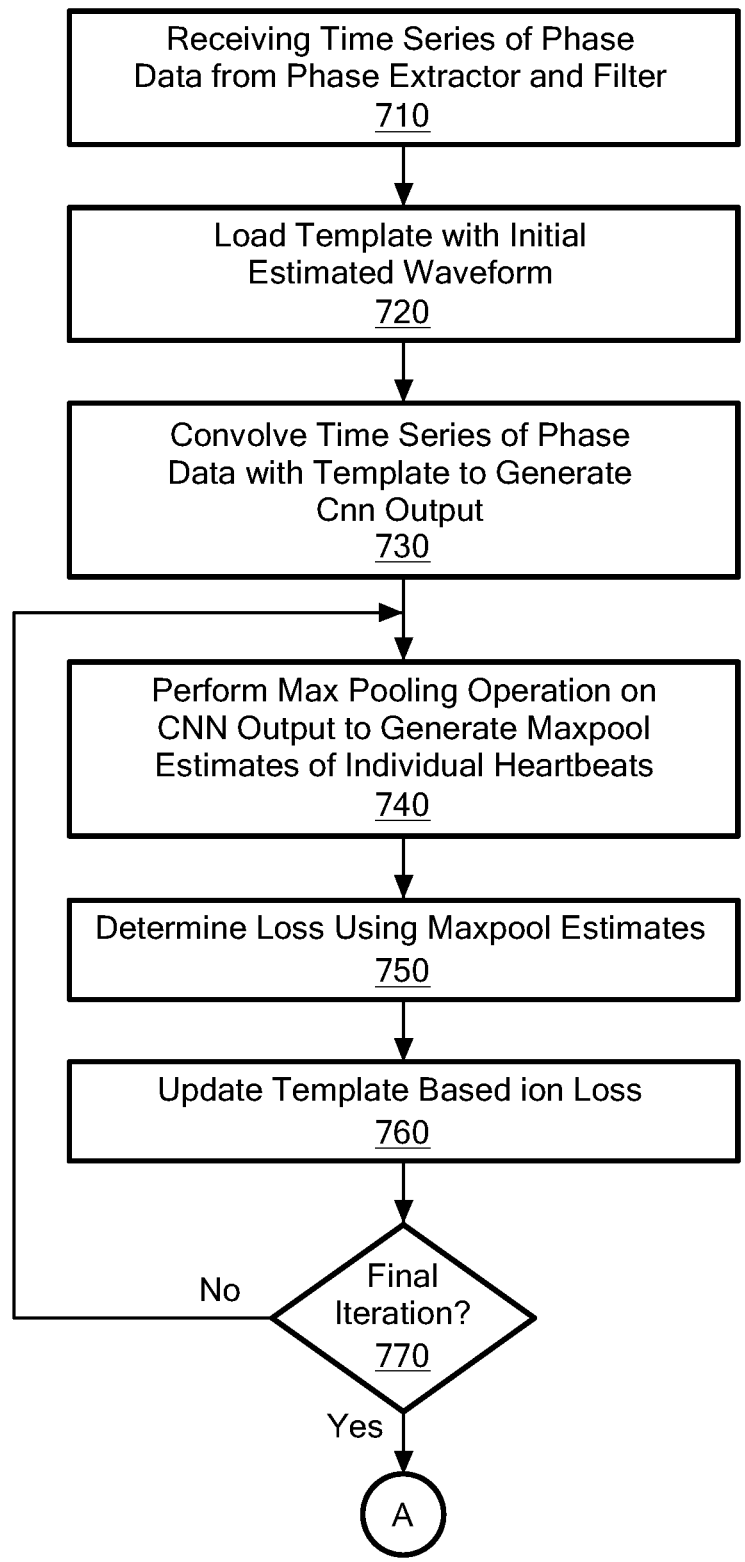
FIGS. 7A and 7B are a flow diagram of an example method of estimating a heart signal.
Figure 7B:
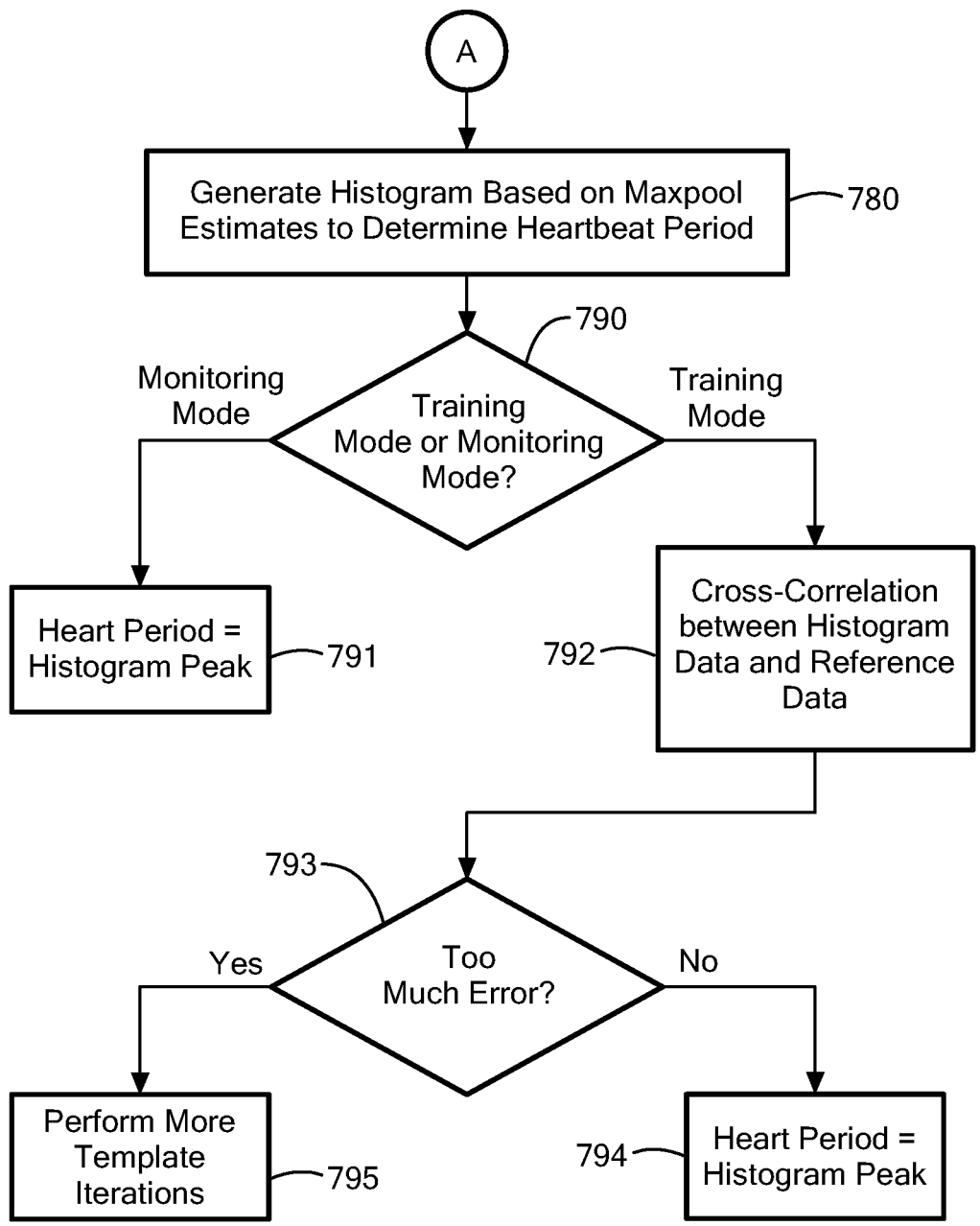

FIG. 6A shows an input waveform 610 of wireless reflected signals (e.g., time series of phase data) that may be received from the phase extractor and filter 411. (Operation 710).

Figure 6B:
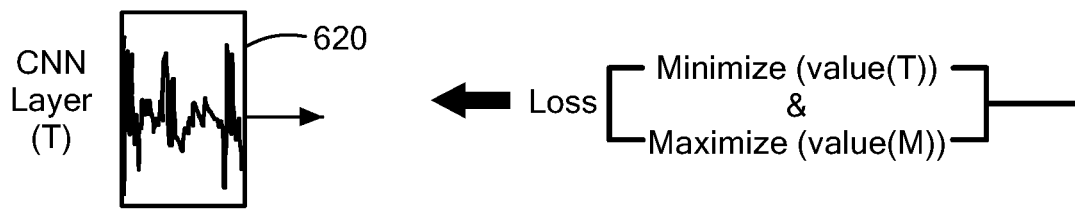

FIG. 6B shows a 1D CNN layer 620 that iteratively generates (or "learns") a sliding template T as its convolution filter, as mentioned above. On the first iteration, the template T is loaded with a waveform which, for example, may be an initial estimate of a single heartbeat interval that may be repeated throughout a sensing period. The initial estimate may be, for example, a predetermined estimate (e.g., generally resembling a human heartbeat interval) or may correspond to training data or even a previous record of the particular heartbeat interval of the patient that has been archived. In one embodiment, the template T may correspond to initial parameters which may be random values with a normal distribution. (Operation 720).

Figure 6C:
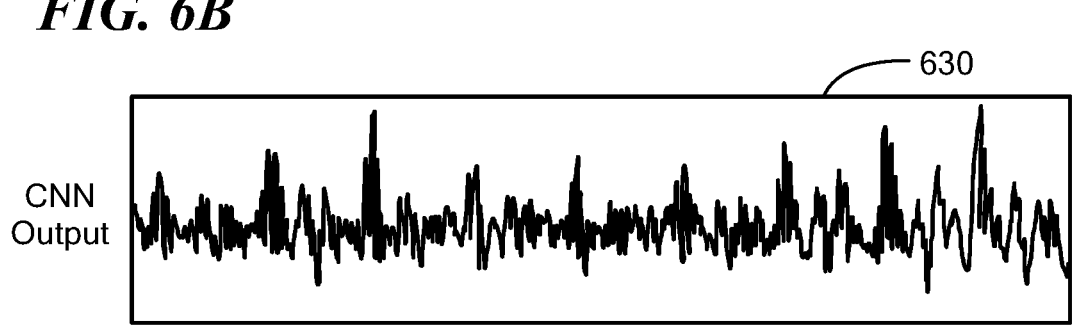

FIG. 6C shows the output 630 of the convolution of template T of the CNN layer 620 with the time series of phase data corresponding to input waveform 610 over a predetermined time period. (Operation 730). The predetermined time period may be the entire detection period of the input data waveform 610 or only a portion of that period. The portion of the detection period may be arbitrarily determined or, for example, may be predetermined relative to a starting time of the detection period.

Figure 6D:
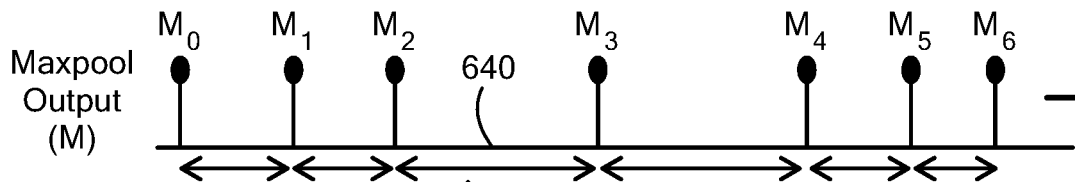

FIG. 6D shows that a Max pooling operation may be performed for the CNN layer output 630 that generates a Maxpool layer 640. (Operation 740). This Maxpool layer may be generated to better interpret the embedded information in the CNN layer output 630. For example, the Maxpool layer 640 may be used to find a maximum value within a window (|Di*T|) as in Equation 3 which will generate a loss term (1/M) as in Equation 4. In one embodiment, the Max pooling layer 640 may include the most activated presence of a feature (e.g., heartbeat) in the CNN output 630. In an alternative embodiment, another pooling method may be used, e.g., an average pooling method that summarize these average presence of a feature (e.g., heartbeat).

In the example of FIG. 6D, the Max pooling operation may result in a segmentation of the time-domain series of the CNN output 630 into individual heartbeats. This may produce peaks corresponding to the CNN output that represent Maxpool estimates (M0, M1, . . . , M6). The peaks may arise whenever the template T is aligned with a single heartbeat. Thus, the number of peaks may be indicative of the number of heartbeats in the duration corresponding to the input data waveform or a designated portion thereof. The number of peaks M in FIG. 6D is shown to be 6 (M1 to M6), but this is just an example and may be different in another embodiment.

Once the Maxpool layer 640 is generated, an indication of loss may be determined (Operation 750) and corresponding information may be fed back to the CNN layer 620 in order to update (or refine the waveform of) the template T (Operation 760). The loss may be determined, for example, by a loss function corresponding to Equation (4).

$$\text{Loss} = \wedge_2(T) + \lambda \frac{1}{M} \quad (4)$$

where $\wedge_2$ is L2-norm, M is L2-norm of the values of each Maxpool output element, and $\lambda$ is a tuning parameter. Mathematically, the first term corresponds to a regularization term for penalizing the loss function to prevent overfitting and it also represents the template size term (|T|) in Equation 3. The second term corresponds to the cross-correlation term (|Di*T|) in Equation 3 for maximizing the similarity between the template (T) and input data (D). When $\lambda$ is too small or too big, it will fail to find an optimal solution of Equation 3. The value was determined experimentally. Through these operations, the loss may be indicated by values minimize (value (T)) and maximize (value (M)), which values may be used as a basis for updating the CNN layer template T, as symbolically shown along feedback path 445.

This process is performed for a plurality of iterations. The number of iterations may be determined based on the loss (or error) falling below a predetermined level. As long as the loss (e.g., as per Equation (3)) is greater than the predetermined level, more iterations are performed to refine the template T. (Operation 770, No). Once the loss equals or falls below the predetermined level, that last iteration may be considered the final iteration. (Operation 770, Yes). The iterative process therefore continues until there is a convergence that generates a learned template T which is highly accurate. At this point, it may be said that template matcher 612 has achieved reducing or minimizing the template matching error (e.g., as per Equation (3)).

Figure 6E:
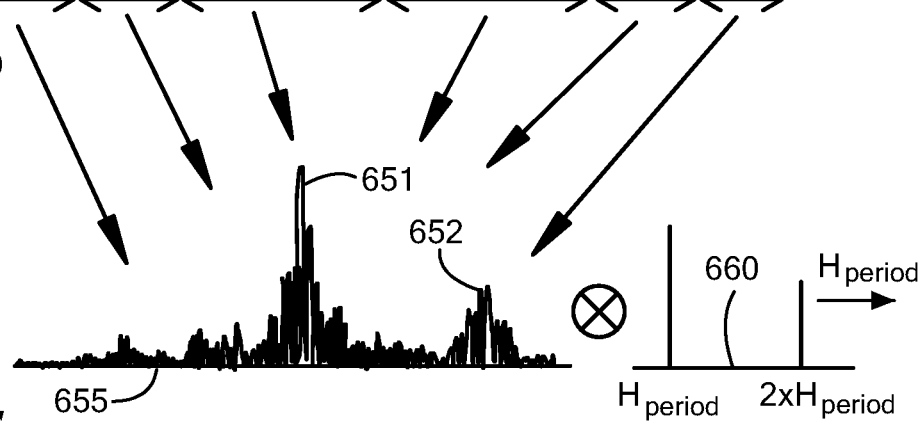

FIG. 6E shows a histogram 655 of the Maxpool differences generated by the final version of the Max pool layer of FIG. 6D. (Operation 780). The histogram corresponds to the estimated heartbeat period across all individually measured heartbeats and is generated based on the segments shown in the Maxpool output (corresponding to the arrows linking FIG. 6D to FIG. 6E). The number of signals in each segment may, along with the Maxpool peak (M) values, be used to generate the histogram data. The histogram data shows two peaks, namely a primary (or maximum) peak 651 and a secondary peak 652 of lower amplitude than the primary peak. The primary peak 651 may correspond to the fundamental harmonic of the heartbeat period and the secondary peak 652 may correspond to the second harmonic of the heartbeat period.

The operation performed next may be determined based on whether the mode of operation of the heart beat analyzer. (Operation 790). If the mode is monitoring mode (e.g., after the learned template T has been formed by divergence) which represents an actual in-the-field use, the primary peak 451 may be the output of the heart rate estimator 410 indicative of heart rate. (Operation 791). In one embodiment, the template matcher may not have a training mode with ground truth data. Instead, in one embodiment, the template matcher may try to find an optimal template (e.g., 620 in FIG. 6B) for each given input (e.g., 610 of FIG. 6A) by minimizing (or reducing) the loss value 645. The CNN layer may be initialized for every different input.

If the mode is training mode, a cross-correlation $\otimes$ operation may be performed between the histogram data 655 (including peaks 651 and 652) and reference data 660. (Operation 792). In one embodiment, the reference data may correspond to a predicted range of heartbeat rate and/or an actual heart rate measurement generated, for example, from an accelerometer being worn by the patient. In one embodiment, the cross-correlation operation may be performed between the histogram data 655 and a harmonic impulse function 660 based on the peaks. Next, a check may be performed to determine whether there is too much error (Operation 793). If the cross-correlation indicates that there is too great a disparity between the histogram data 655 and the reference data 660, the heart rate indicated by the peak 651 of the histogram data may be considered to correspond to a non-final heart rate estimate. In this case, control may return to perform further iterations to continue template learning until the cross-correlation between the histogram data (Operation 795) and reference data falls with a predetermined acceptable error range, thereby producing a final heart rate estimate corresponding to the histogram peak (Operation 794). In one embodiment, there may be no training mode in this stage. Rather, it may just sweep the cross-correlation operation within every possible heartbeat period range and then select the heartbeat period that has the highest correlation value. The heart rate may be determined based on an inverse of the heartbeat period, e.g., e.g., heart rate=1/Hperiod.

Through these operations, information indicative of the heart period (Hperiod) of the patient may be determined, along with a value corresponding to 2× (Hperiod). This heart rate information may then be output to Extractor 430.

Additionally, it is noted that the heartbeat period may be extracted by taking the difference between any two neighboring Maxpool outputs ($M_n$–$M_{n-1}$). This operation may be performed, for example, using a machine-learning model. In one embodiment, this model may not need to be separately pre-trained because the training process of the model logic may be used to extract the heart rate estimate. A different method may be used to extract heart rate in other embodiments. However, these different methods may not prove to be as accurate as the template-matching embodiment for at least some applications.

For example, in one embodiment a Fast Fourier Transform (FFT) may be used to extract the heart rate and identify the peak frequency. However, this approach may not produce as accurate an estimate because the heartbeat of a person tends to change from interval-to-interval, making it more challenging to robustly obtain a sharp peak at the heartbeat frequency. In contrast, the template-matching approach described in accordance with one or more embodiments may be performed based on a local maximum of the CNN output 430 in FIG. 4C. Therefore, the template-matching embodiment may not require a response to be perfectly periodic in order to achieve an accurate result.

In addition, the histogram-based method for extracting heartbeats, as described above, may be highly robust to noise or random sources of error, since these would not contribute to or distort the dominant period/frequency.

In some embodiments, a template-matching method different from the CNN-based approach described above may be used. However, for many applications the CNN-based approach may be more desirable for at least three reasons. First, the CNN-based approach may be easily implemented using highly optimized machine-learning frameworks (e.g., Tensorflow, PyTorch, etc.). Second, the CNN-based approach is performed in linear time. Third, the CNN-based approach may achieve high robustness and accuracy with minimal parameterization, e.g., in one embodiment the only hyper-parameters to be set are the learning rate, $\lambda$, and a layer size of Maxpool and CNN. The main constraint to be accounted for was to ensure that the Maxpool and CNN layers are larger than one heartbeat interval, which can be addressed by choosing a sufficiently large number.

Returning to FIG. 4, the phase extractor 420 projects the channel signals into a predetermined number of possible directions. In one embodiment, this may be accomplished by combining beamforming techniques with a Fast Fourier Transform (FFT) via four-dimensional projections, to identify spectral features coming from one or more different regions from the surrounding environment. In one embodiment, the spectral features may correspond to one or more points in a three-dimensional (3D) space. The logic of the phase extractor 420 then uses the estimated heart rate (determined by the heart rate estimator 410) to identify a correct (e.g., a 3D) spatial beam.

Once this spatial beam is identified, the phase extractor 420 extracts the phase $\phi$ of this beam. These operations may be performed in a predetermined manner, e.g., sequentially. In one embodiment, the phase extractor employs an algorithm that exploits the periodicity of the heart rate estimate output from the heart rate estimator 410, in order to determine an optimal steering direction for the radar antenna 140. FIG. 4 shows one possible logic operation flow that may be used to identify the optimal projection. The operations in this logical flow may correspond to the method embodiment of FIG. 8

Figures 8, 10:
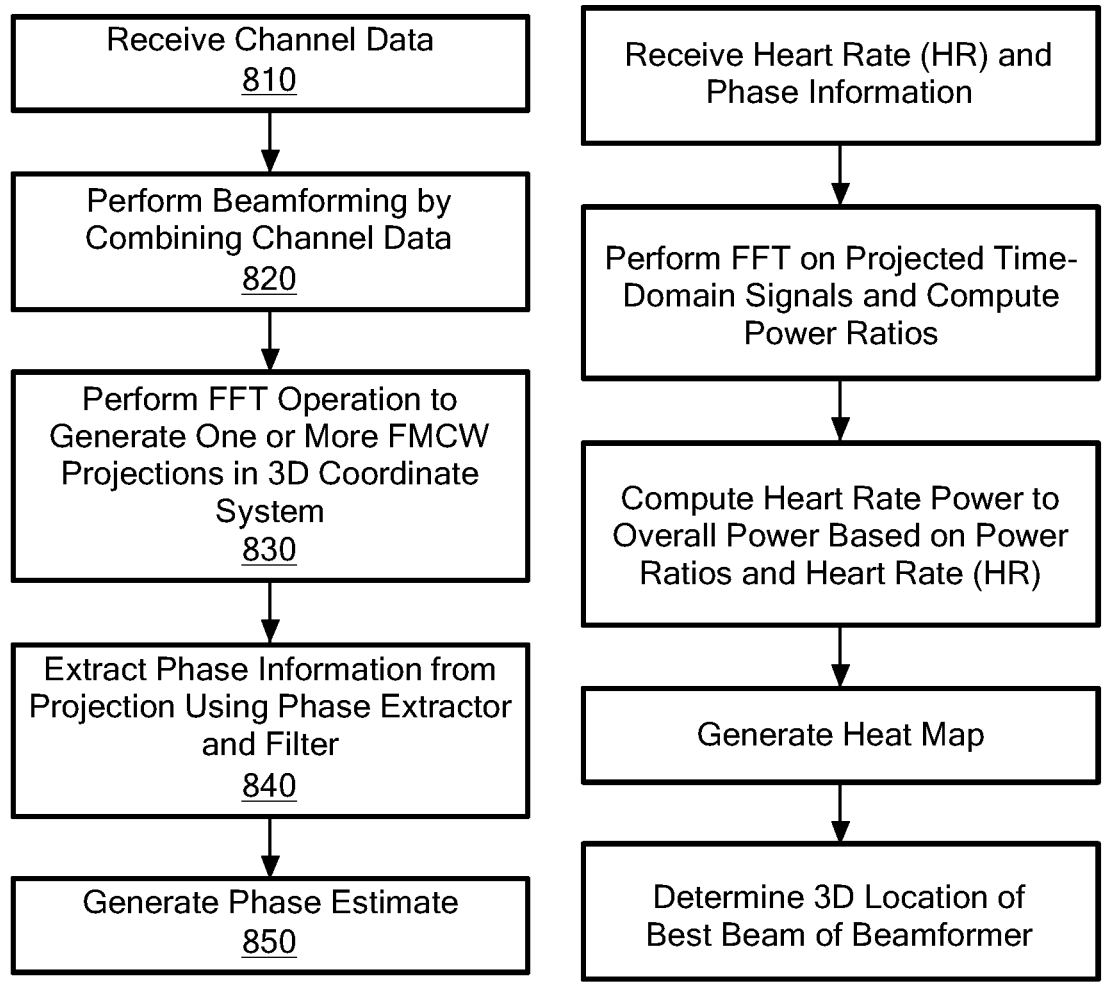
FIG. 8 is a flow diagram of example method of generating a phase estimate.
FIG. 10 is a flow diagram of a method for determining beam location.

Referring to FIGS. 4 and 8, the phase extractor 420 may include first logic 421 and second logic 422. The first logic 421 may perform beamforming and FFT operations, and the second logic 422 may perform phase extraction and filtering operations. As previously indicated, the input into the beamforming and FFT logic 421 corresponds to the wireless reflected channel data output from the antenna receive elements vis-à-vis the detector 150. (Operation 810). The signals $m_n$ received on each of these channels may be expressed by Equation (5).

$$m_n = A_n \times e^{j\phi_n(t)} \quad (5)$$

where $A_n$ denotes the amplitude and $\phi_n(t)$ denotes the phase of nth channel signal. As indicated in FIG. 4, these signals serve as inputs into the phase extraction and differentiator filter 411 and the beamforming and FFT logic 421.

In one embodiment, the beamforming logic 421 may apply the following beamforming method to steer the direction of the beam BF(x,y). First, the signals received on all channels (e.g., in this case 8) are combined based on Equation (6). (Operation 820).

$$BF(x, y) = \sum_{n=1}^{8} \exp\left(\frac{-j2\pi}{\lambda}[x_{d,n} \cdot x + y_{d,n} \cdot y]\right) \times m_n \quad (6)$$

In Equation (6), $\lambda$ is the wavelength of the transmitted RF signal, xd,n and yd,n are the coordinates of the $n^{th}$ antenna array in a multi-antenna array embodiment, x and y are projected coordinates, and $m_n$ is received signal from the $n^{th}$ antenna array.

After applying this beamforming operation, the FFT logic 421 may perform an FFT operation to generate one or more FMCW projections. (Operation 830). This operation may be performed to isolate reflections coming from different distances into different frequency ranges (or buckets), for example, as described herein. As a result of these operations, logic 421 obtains one or more projections into one or more different regions of a surrounding environment, which may or may not be a 3D coordinate system 328, e.g., x, y, and intermediate frequency areas. The projections are time-domain signals. It is possible to verify the quality of each projected time-domain signals by plotting them on a complex plane.

FIGS. 9A and 9B show examples of two potential outcomes of the projections with different projection qualities. FIG. 9A shows messy circles 910 around an origin point without a hole at the center. This indicates a destructive interference pattern, e.g., the projection did not constructively combine the channels. FIG. 9B shows a thick concentric circle 920 generated by a constructive interference pattern of individual projections, This demonstrates that the overall projection is close to ideal, e.g., as per Equation (5). The first projection with messy circles of FIG. 9A may be rejected. The projection with the thick concentric circle of FIG. 9B includes embedded phase information that may be extracted by logic 422.

After a protection of a type corresponding to FIG. 9B is formed, the signals from thus projection are input into logic 422, which operates as a phase extractor and filter. (Operation 840). The phase extraction and filtering operations generate a phase estimate $\phi$ which corresponds to the output of logic 422. (Operation 850).

The phase extraction operation of logic 422 may involve generating a time-domain series of data using a processor similar to that of differentiator filter 411, e.g., phase extraction may be performed for FMCW as explained herein. The phase angle in the interval $[-\pi, \pi]$ may be computed for each element of complex inputs. Whenever the jump between consecutive angles is greater than or equal to pi radians, the angles may be shifted by adding multiples of $\pm 2\pi$ until the jump is less than $\pi$. In one embodiment, the differentiator filter may be a kind of high-pass filter designed such that the output of the filter is approximately directly proportional to the rate of change (the time derivative) of the input. So, the filter may have high gain in the high frequency band.

In one embodiment, the differentiator filter of logic 422 may be trained, for example, with the RF-to-seismocardiogram translator in a manner discussed below. In one embodiment, the differentiator filter may be initialized with an initial set of differentiator filter coefficients and may be trained to maintain symmetry.

The calculator 430 generates information indicative of a three-dimensional location of the antenna beam corresponding to wireless reflected signals that are most likely to give the most accurate seismocardiogram when converted by the RF-to-seismocardiogram translator. Operations of the calculation correspond to those in the method embodiment of FIG. 10.

Referring to FIGS. 4 and 10, the calculator 430 receives information indicative of the patient heart rate (HR) and the phase information $\phi$ respectively output from the heart rate estimator 410 and the phase estimator 420. (Operation 1010).

The calculator then calculates a predetermined power ratio based on the heart rate and phase information. The predetermined power ratio may be, for example, the highest cardiac power ratio and may be determined as follows. First, the calculator 330 takes the FFT of the projected time-domain signals corresponding to the phase information and computes the power ratio of the heartbeat power to the overall power across coordinates and buckets. (Operation 1020). For example, each time-domain signal (at the output of the phase extractor 420) is parameterized by 3 coordinates. Thus, by taking the FFT of each of these signals, their time-domain spectral properties may be obtained.

Second, knowing the heart rate estimate from the output of the CNN-based template matcher 412 of the heart rate estimator 410, the ratio of the heartbeat power to the overall power across coordinates and buckets may be computed. (Operation 1030). This results in the generation of a 4D heatmap 431, where the four dimensions are x, y, frequency buckets, and power ratio. (Operation 1040).

Third, based on the 4D heat map 431, a location (e.g., an optimal 3D location) may be identified as the one having the highest power ratio, e.g., where the periodicity of the heartbeat is most pronounced. (Operation 1050). A plurality of heat maps may therefore be generated over the duration of the input waveform 610.

FIGS. 9C and 9D show example plots that may demonstrate values of a heat map projection 331. FIG. 9C is a plot showing the time-domain phase extracted from a first location in the projection 431, and FIG. 9D is a plot showing the time-domain phase extracted from a second location in the projection 331. The phase in the FIG. 9C plot is from a random coordinate in the projection (without loss of generality, the origin) and barely shows any periodicity. However, the phase in the FIG. 9D plot corresponding to a location of a peak of the projection clearly shows periodic signals. This demonstrates the ability of one or more embodiments of the Cardiac Beamformer 210 to focus on and accentuate reflections from the heart of a patient and thus may serve as a basis for identifying a beam location that is appropriate for use in generating the information to be input into the RF-to-seismocardiogram translator.

In some embodiments, additional processing may be performed to suppress outliers and extraneous movement reflected in the signals. For example, after beamforming, corrupted data may be filtered out. The corrupted data may result from various environmental factors (e.g., excessive movement of the patient, another object coming in the way between radar-based sensor and the patient, etc.). These environmental factors may cause sudden peaks to occur or may otherwise distort the received signal. In one embodiment, these specious peaks and distortions may be removed.

To identify and eliminate the corrupted data, the calculator 430 may include logic that performs, for example, a statistical analysis called Tukey's fence. In implementing this analysis, the logic identifies thresholds for rejecting outliers based on quartiles of the time series. To implement this method, the logic divides the obtained time-series projections into two-second windows, calculates the power distribution across all unit windows, and then extracts the first quartile (Q1) and third quartile (Q3). Based on these values, the logic may define a threshold Pth based on Equation (7). Then, if the power of any unit exceeds this threshold, it is discarded.

$$P_{th}=Q_3+1.5\times(Q_3-Q_1) \tag{7}$$

Wireless-to-Seismocardiogram Translator

The Wireless-to-seismocardiogram translator 330 generates seismocardiogram recordings (or signals) based on the wireless reflected signals received from the beam identified by the Beamformer 310 or, for example, from the detector in an embodiment where the Cardiac Beamformer is omitted. The seismocardiogram recordings may be generated by learning a transformation filter (or translation function) that translates the wireless reflected signals to seismocardiograms, from which meaningful clinical parameters may be subsequently determined and labeled. For example, when the wireless signals are millimeter waves (mmW), translator 330 may translate mmW reflections to seismocardiogram waveforms for output to the Automatic Labeler 350.

In one embodiment, the length of one frame may be fixed but the number of channels may be different across layers of the filter. To translate mmW reflections to seismocardiogram recordings, a deep-learning model may be used to implement the filter. For example, the deep-learning model may be a convolution neural network, with every convolution layer functioning as an FIR filter. The coefficients of every CNN layer may then be updated based on a calculated L2-Norm between a ground truth (serving as a reference) and the translated results.

In one embodiment, some examples of the Wireless-to-seismocardiogram translator is an RF-to-seismocardiogram translator and a WiFi-to-seismocardiogram translator. For convenience purposes, the Wireless-to-seismocardiogram translator will be described in example embodiments below as an RF-to-seismocardiogram translator with the understanding that WiFi- or other types of Wireless-to-seismocardiogram translator may be implemented in other embodiments.

The RF-to-seismocardiogram translator 330 may learn the coefficients of the filter from mmW and SCG data pairs. Because an FIR filter and 1-dimensional convolutional neural network (1D-CNN) have the same mathematical representation, multiple 1D-CNN layers may be considered as multiple FIR filters used to implement the translation performed by the translator 330. As a result, fine-grained cardiovascular movements may be represented by the combination of various frequency components from mmW signals.

Figure 11:
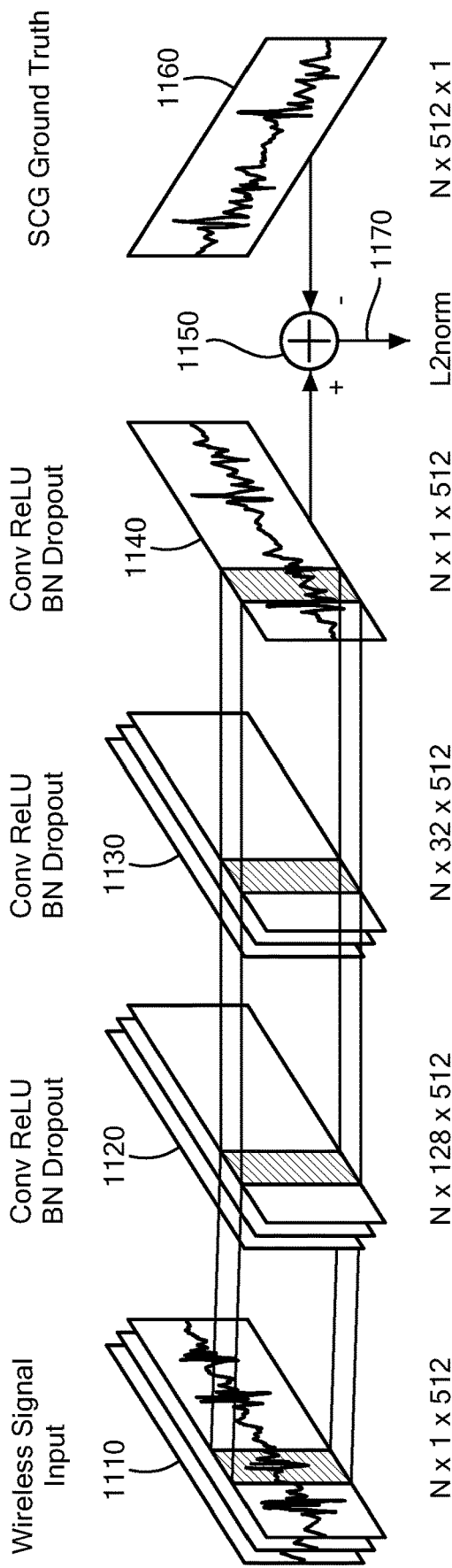
FIG. 11 is a block diagram illustrating a technique for performing wireless signal input-to-seismocardiogram translation.

FIG. 11 shows an embodiment of a translation filter including multiple layers that may implemented by the RF-to-seismocardiogram translator 330. The translation filter includes a first layer 1110 that corresponds to an input into the translation filter. This input corresponds to reflected millimeter-wave time-series detected from a beam direction indicated by the Cardiac Beamformer. In this example, the input is organized into N batch samples, 512 sample points, and 1 channel, e.g., N×1×512.

At subsequent layers 1120 to 1140, the filter logic groups each of a plurality of CNN layers (Cony) with a rectified linear unit (ReLU) function, batch normalization (BN), and one or more dropout layers (Dropout). The ReLU functions allow the nodes of the model used to implement the filter to learn more complex features in the data by adding nonlinearity. Batch normalization and dropout layers help the networks generalize to diverse input patterns and prevent overfitting. In one embodiment, every CNN layer may have the same length but different channels.

At layer 1150, the coefficients of CNN layers are updated to produce an L2-norm 1150 between the output of the stage (e.g., the output from layer 1140) and an actual SCG measurement 1160 (e.g., a ground truth obtained, for example, from an on-body accelerometer). The actual SCG measurement is used in training mode to train the coefficients of the translation filter. However, once the translation filter coefficients have been trained, the actual SCG measurement and accelerometer that produced this measurement are not used, making the systems and methods described herein contactless during monitoring mode. The seismocardiogram waveform output 1170 (corresponding to L2-norm) from the RF-to-seismocardiogram translator may be reconstructed from millimeter-wave reflections.

Figure 12A:
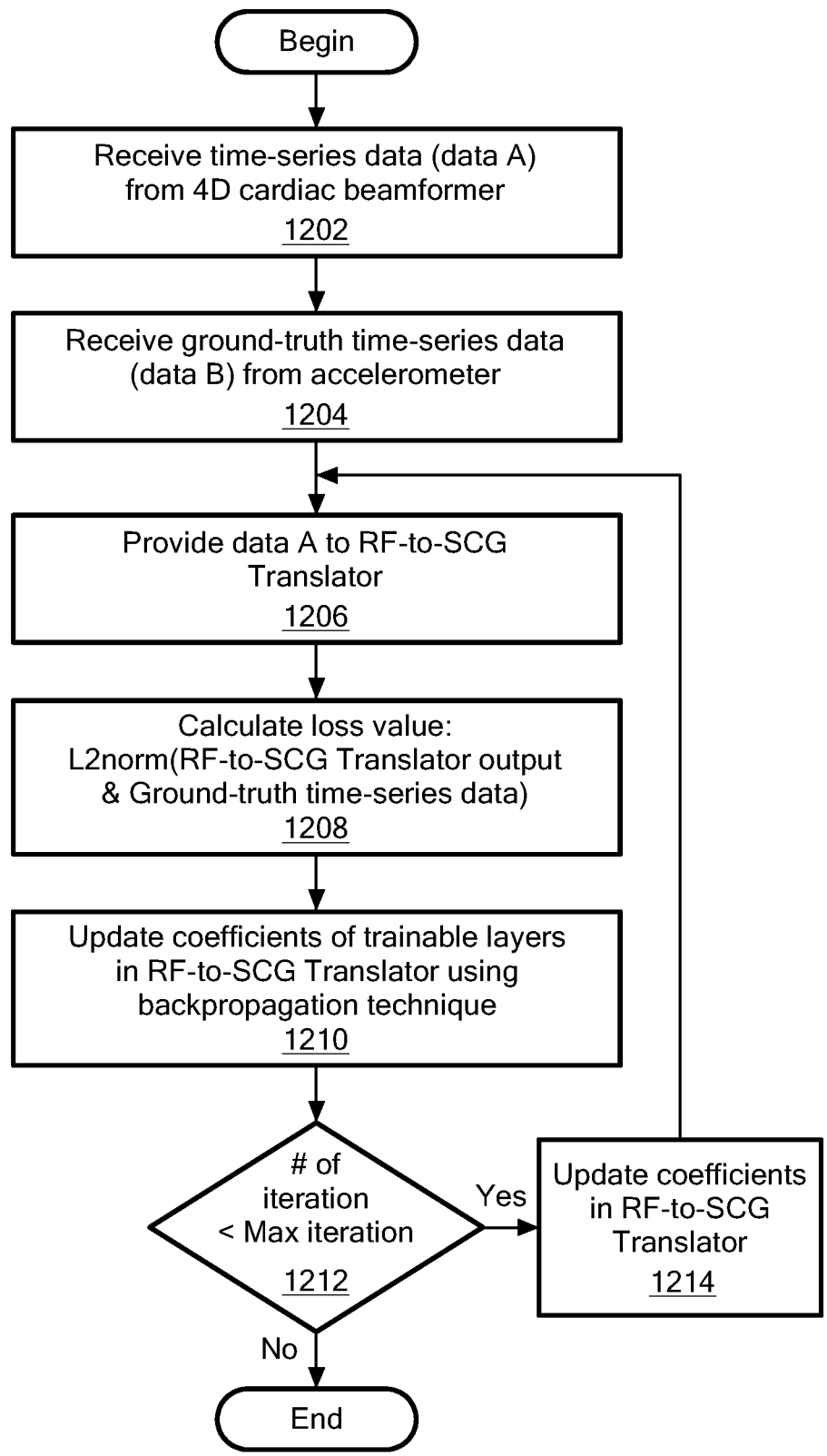
FIG. 12A is a flow diagram of example processing which may be performed by an RF-to-seismocardiogram translator to translate a wireless data signal to a seismocardiogram.

FIG. 12A illustrates a method embodiment including operations performed by the RF-to-SG translator (or translation filter) of FIG. 11. The method may be implemented, first, in training mode first and, then, in a use or monitoring mode. One purpose of the method in training mode is to develop a machine learning model that translates incoming data into an accurate or optimal seismocardiogram recording. Thus, the training mode operation may be considered to implement a training phase of the method, where the machine-learning layers of the model are trained.

Figures 12B, 12C:
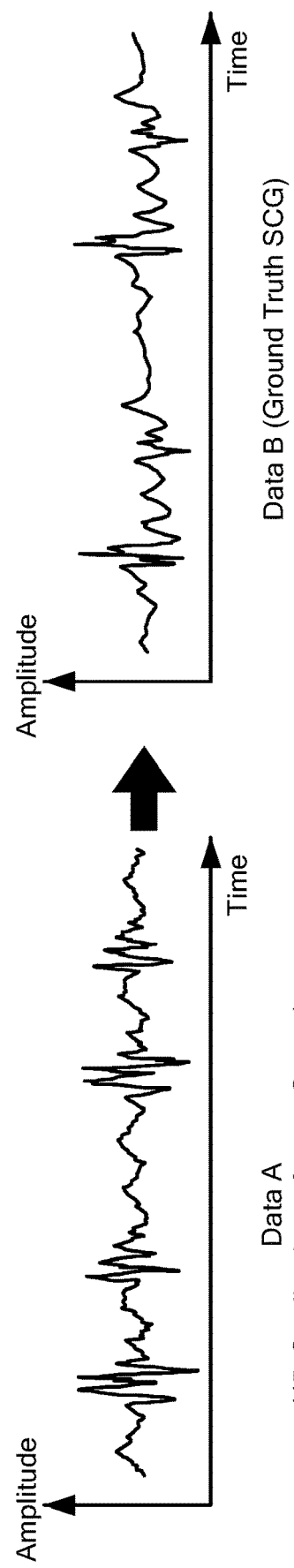
FIG. 12B is a plot of voltage amplitude vs. time for data at an output of a 4D cardiac beamformer (Data A).
FIG. 12C is a plot of voltage amplitude vs. time for ground-truth time-series data received from a sensor.

Referring to FIG. 12A, the method includes, as 1202, receiving time-series data corresponding to the output of the Cardiac Beamformer. The time-series data may be represented, for example, by the waveform for Data A in FIG. 12B, and may include noise and other spurious components that may cause the waveform to include error that inaccurately portrays certain aspects of an accurate seismocardiogram recording.

At 1204, ground-truth time-series data is received from a sensor, which, for example, may be an accelerometer. This data may correspond to the waveform for Data B in FIG. 12C and may be used as comparative reference data. For example, Data B may be considered to be an accurate seismocardiogram recording.

At 1206, Data A is input into the transformation model of the RF-to-seismocardiogram translator. The model may be initially based on predetermined values (e.g., coefficients and/or other parameters), which are to be subsequently adjusted in an iterative manner to generate a transformation function output that causes Data A to correspond more closely to Data B.

At 1208, a loss value is calculated based on Data A and Data B. The loss value may be indicated by the value L2norm and, for example, may indicate the differences between Data A and Data B, e.g., may correspond to error data indicative of the difference between the time-series data output from the Cardiac Beamformer and the ground-truth time series data. The loss may be calculated, for example, based on a mean squared error technique, an example of which is given by Equation (8).

At 1210, the coefficients and/or other values of equations (e.g., transformation function) in one or more trainable layers of the model may be updated based on the error data generated in operation 1208, e.g., based on L2norm. Updating the one or more trainable layers may be performed, for example, using a backpropagation technique. In other embodiments, other techniques may be used to update the coefficients of the trainable layer(s). In one embodiment, the foregoing operations may be considered to correspond to a first iteration of the method.

At 1212, a determination is made as to whether additional iterations should be performed. For example, this may involve determining whether the number of iterations is less than a predetermined (e.g., maximum) number of iterations. In another embodiment, this may involve determining whether the error data (e.g., L2norm) is less than a predetermined level. The determination of operation 1212 may be based on another measure in another embodiment.

At 1214, if the number of iterations performed is less than the predetermined number of iterations (Y, in FIG. 12A), then the method performs another iteration which involves updating coefficients in the RF-to-seismocardiogram translator. This may correspond to operation 1210 in which case no additional action may be taken, or may involve updating transformation coefficients of the model based on the updated coefficients or other values of the trainable layers. Once operation 1214 is performed, the method returns to operation 1206, where Data A is re-input into the model along a feedback path. Operations 1206 to 1212 are repeated, this time based on the updated coefficients.

If the answer to the inquiry in operation 1212 is no (e.g., if the number of iterations performed equals or exceeds the predetermined number of iterations), then the RF-to-seismocardiogram translator model may be considered to have been trained for use in monitoring mode.

Figure 12D:
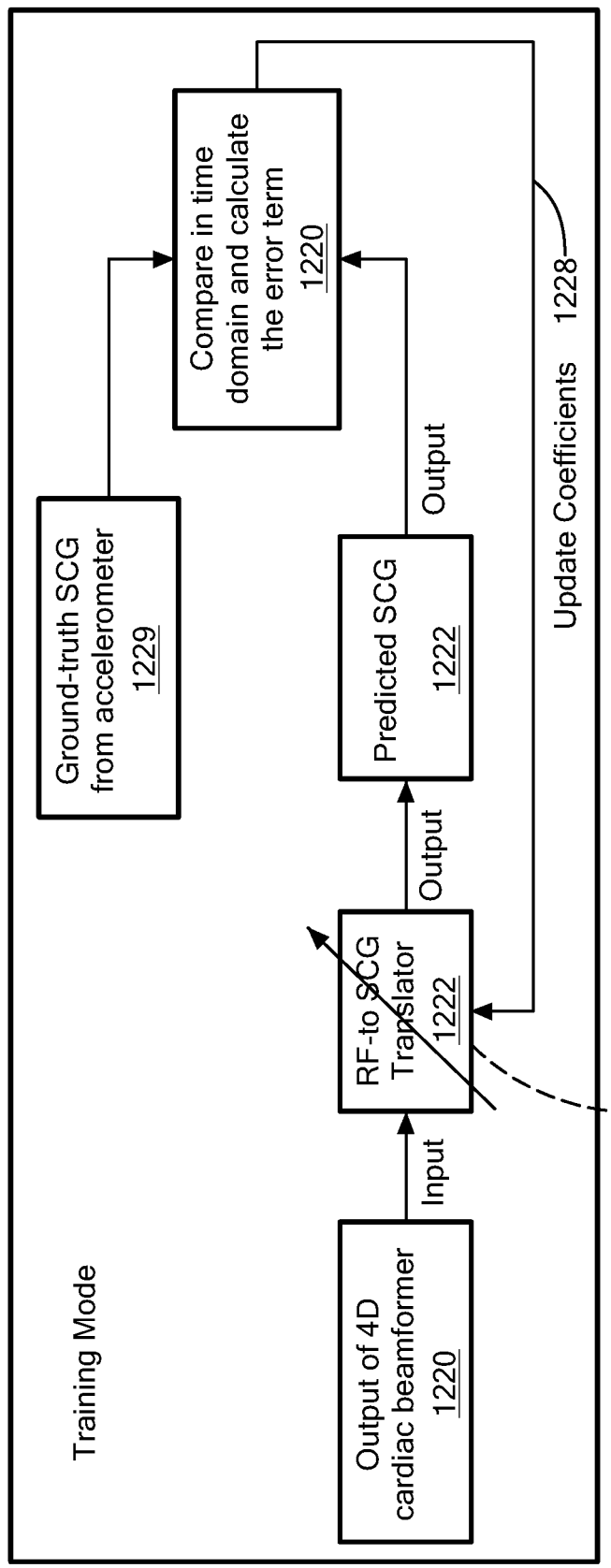
FIG. 12D is a block diagram of an embodiment of a wireless signal input-to-seismocardiogram translator in training mode.

FIG. 12D illustrates an embodiment of a method which may be used to complete the loss (L2norm) or error data of operation 1208. This method includes, at 1220, transferring the output of the cardiac beamformer as an input into the RF-to-seismocardiogram translator. At 1222, as initially configured, the RF-to-seismocardiogram translator generates an output based on the input as previously described. At 1224, the output of the translator corresponds to a predicted seismocardiogram. At 1226, the predicted seismocardiogram generated by the model is compared to the reference seismocardiogram output from the accelerometer, e.g., ground-truth seismocardiogram 1229. This comparison may be performed, for example, in the time domain and results in generating an error term that may be indicative of how far off the predicted seismocardiogram is from the actual seismocardiogram. If more iterations are to be performed (e.g., based on the determination discussed in FIG. 12A), second or subsequent numbers of iterations are performed along feedback path 1228. After the final iteration, the model coefficients (e.g., of the translator function) are frozen, or set. At this point, the RF-to-seismocardiogram translator may be considered ready for monitoring mode.

Figure 12E:
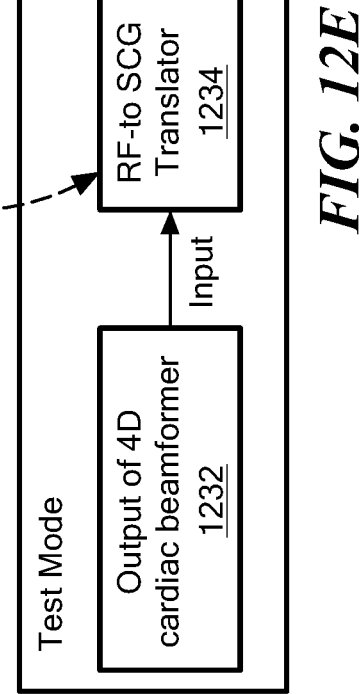
FIG. 12E is a block diagram of an embodiment of a wireless signal input-to-seismocardiogram translator in test mode.

FIG. 12E illustrates a method embodiment including operations performed by the RF-to-seismocardiogram translator in monitoring mode, e.g., in testing mode when actually used to generate a seismocardiogram for a patient. Because the translator has already been trained, the output of the translator may be considered to generate an accurate (or even optimal) seismocardiogram which outperforms other proposed methods and systems.

Referring to FIG. 12E the method includes, at 1232, sending the output of the cardiac beamformer to the RF-to- $$\text{Loss} = \Sigma[\text{Translator}(\text{data}A(t)) - \text{data}B(t)]^2 \qquad (8)$$

seismocardiogram translator. At 1234, the translator generates a predicted seismocardiogram based on the coefficients set during the training mode. The predicted seismocardiogram is generated without using the accelerometer, making the system operating in the monitoring mode completely contactless. As 1236, the predicted seismocardiogram is processed in accordance with the embodiments described herein, e.g., which may involve other operations or input into the Automatic Labeler.

Automatic Labeler

The Automatic Labeler 350 detects and labels features in the seismocardiogram waveforms output from the RF-to-seismocardiogram translator. These features occur at certain timings in the seismocardiogram waveforms and correspond to one or more predetermined micro-cardiac events. As indicated, in monitoring mode the labeling function is performed in a contactless manner, and may achieve high accuracy using one or more deep-learning models.

Figure 13A:
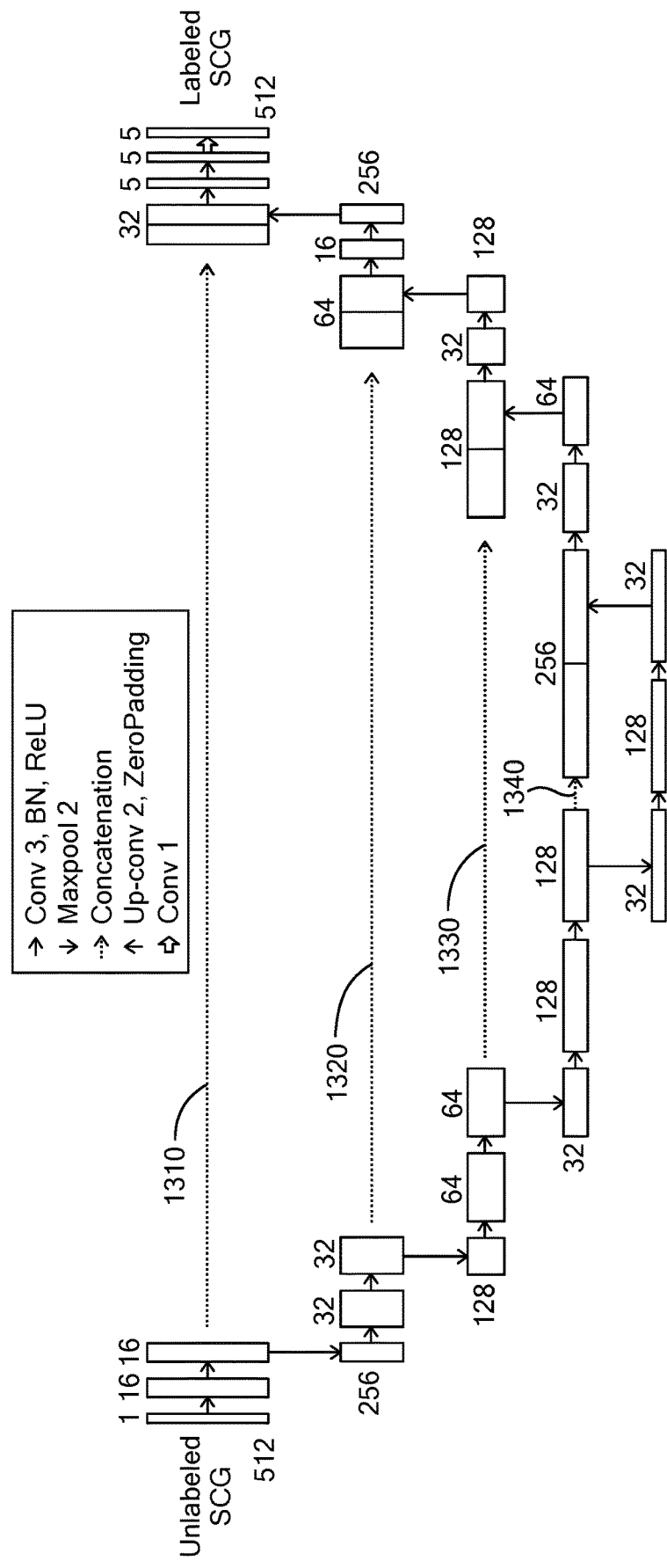
FIG. 13A is a diagram of a Unet deep-learning model.

FIG. 13A shows an embodiment of a Unet deep-learning model which may be used to implement the Automatic Labeler 350. In this case, the Unet model is be adapted to operate with 1D SCG signals, but may operate with 2D or other types of radar and SCG signals in another embodiment. The modified Unet model may implement a convolutional neural network (CNN), parameters of which may be modified for seismocardiogram labeling. The input into the model is an unlabeled seismocardiogram output from the RF-to-seismocardiogram translator 330 and the output of the Automatic Labeler model may be a labeled seismocardiogram.

Referring to FIG. 13A, the Unet CNN model may be logically represented as including a plurality of boxes on four levels. Each of the boxes may correspond to a multi-channel feature map. The height of each box may indicate the number of sample points, and the width of each box may indicate the number of channels for each layer. The arrows may denote different operations performed by the Automatic Labeler. The number of channels is denoted above each box, with white boxes representing copied feature maps.

In this embodiment, the output has multiple channels which represent probabilities of a predetermined number of fiducial points at each sample point. In one embodiment, the output may have five channels representing probabilities of five fiducial points: aortic valve opening (AO), aortic valve closing (AC), mitral valve opening (MO), mitral valve closing (MC), and isovolumetric contraction (IM). If the probability has higher than a certain predetermined threshold value, the Automatic Labeler indicates that the point is determined to be the corresponding micro-cardiac event.

More specifically, in FIG. 13A, the left layers of the network are encoders and the right layers are decoders. By forward feeding features of each layer directly into subsequent ones, the network is able to annotate fiducial points on the input data. (For training, each fiducial point of every SCG data may be manually labeled).

The logical relationship between the components in FIG. 13A is indicated by the directional arrows indicated in the legend. On the left side, the first 4 levels 1310 to 1340 includes two CNNs with Batch-Norm and ReLU functions. These blocks are connected sequentially with MaxPooling layers which extract the maximum value. The maximum value is fed to the input of lower level block, which contains two CNNs with batch normalization and ReLU function. The output from the previous layer through the deconvolution and zero padding layers are concatenated with the output from the layer from the same level on the left side and is fed to the input of the block that includes CNNs each with the Batch-Norm and the ReLU. The output from the previous layer through the deconvolution and zero padding layers is sequentially fed to the input of another 4 floors containing two CNNs each with Batch-Norm and ReLU. The output from the previous layer is fed to the input of another CNN with the size of the kind of fiducial points. The output of the automatic labeling stage includes the probabilities of the fiducial points for each of the samples. Using this probability, RF-SCG can automatically label the seismocardiogram waveforms.

Figure 13B:
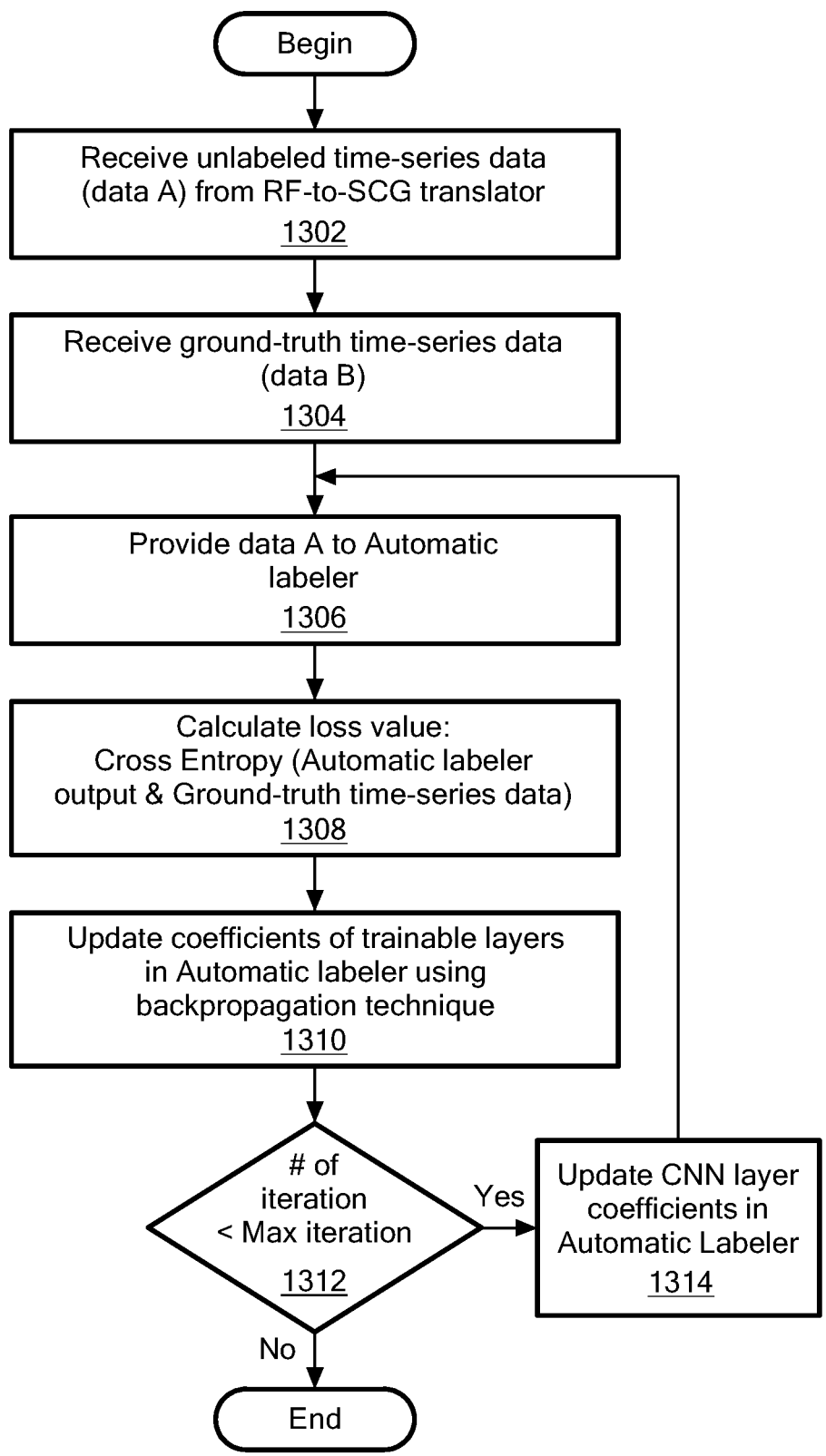
FIG. 13B is a flow diagram of operations included in a method for automatically labelling a seismocardiogram.

FIG. 13B illustrates an embodiment of an automatic labeling method that may be implemented by FIG. 13A of the Automatic Labeler. The Automatic Labeler may operate, first, in training mode and then in monitoring (or labeling) mode.

Referring to FIG. 13B, the method includes, at 1302, receiving unlabeled time-series data from the RF-to-seismocardiogram translator. At 1304, ground-truth time-series data is received, for example, as reference data. At 1306, input unlabeled time-series data received in operation 1302 into model of the Automatic Labeler. The model includes a preliminary set of coefficients and/or other values used for labeling the seismocardiogram output from the translator.

At 1308, a loss value is calculated based on a comparison of the output of the model and the ground-truth time-series data. In one embodiment, the loss value may be calculated based on a cross entropy technique. The loss value may calculated using a different technique in another embodiment.

At 1310, the coefficients and/or other values of trainable layers of the Automatic Labeler are updated based on the loss Value. In one embodiment, this updating operation may be performed, for example, based on a backpropagation technique. The updating operation may be performed using a different technique in another embodiment.

At 1312, a determination is made as to whether additional iterations of the method should be performed, in order to further train the model. In one embodiment, the iteration number of the method is compared with a predetermined number, for example, indicative of a maximum number of iterations to be used for training. In another embodiment, a determination may be made as to whether the calculated loss is less than a predetermined loss.

If additional iterations are to be performed (Yes, in 1312), then, at 1314, one or more coefficients of the CNN layer of the Automatic Labeler are updated. One or more additional iterations are then repeated based on a feedback path that leads to a repeat of operations 1306 to 1312. If additional iterations are not to be performed (No, in 1312), then, the model of the Automatic Labeler is considered to be trained and ready for operation in the monitoring mode.

Figure 13C:
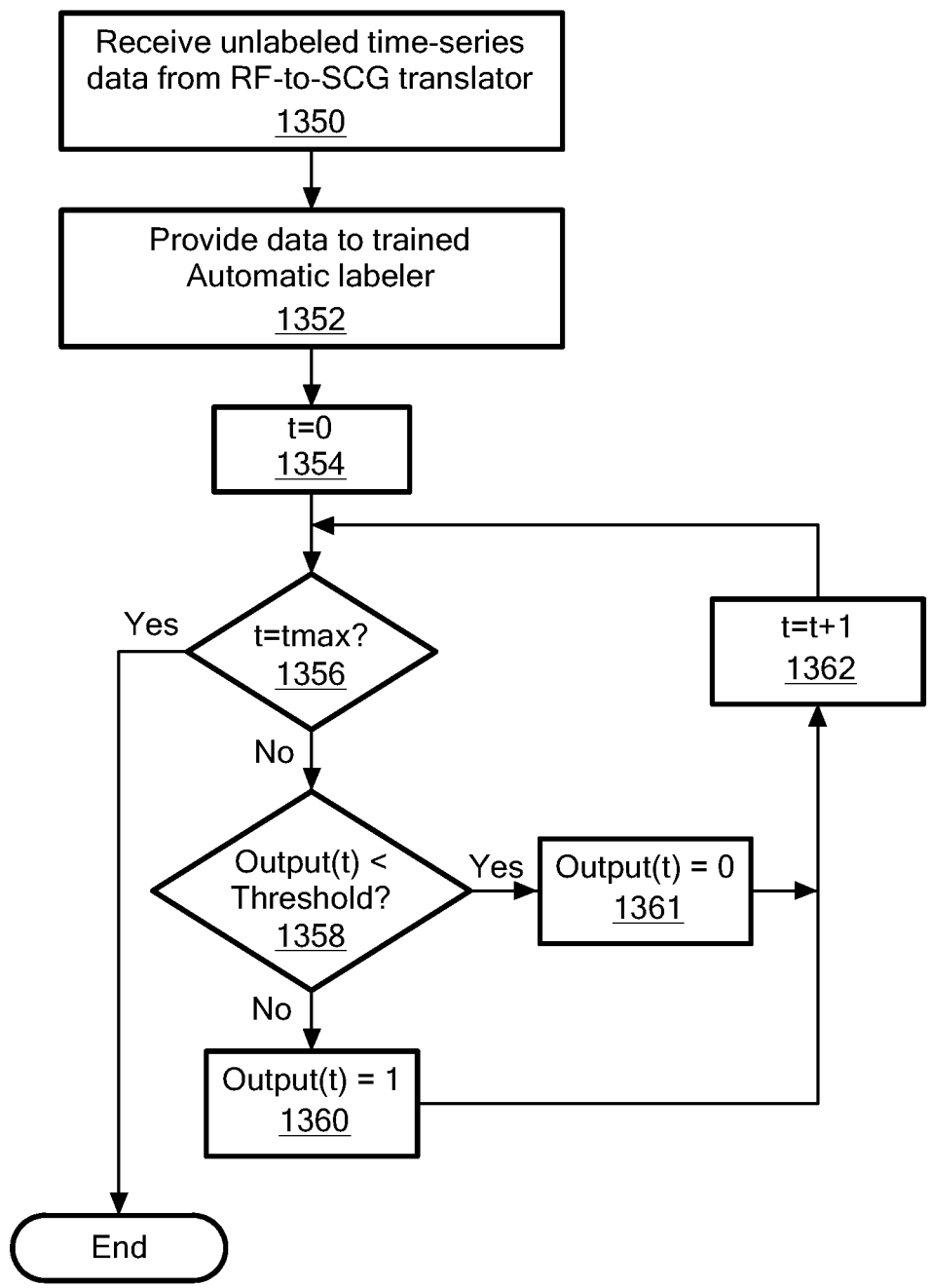
FIG. 13C is a flow diagram of operations included in a method for automatically labelling a seismocardiogram.

FIG. 13C illustrates an embodiment of a method for performing labeling by the Automatic Labeler operating in monitoring mode, e.g., after the model of the Automatic Labeler has been trained. The method includes, at 1350, receiving unlabeled time-series data output from the RF-to-seismocardiogram translator and corresponding to a patient under observation. At 1352, the unlabeled data is input into the trained Automatic Labeler. At 1354, an initial counter value is set to an initial value, e.g., t=0.

At 1356, an iterative set of operations may be entered in order to identify and label states of interest. These operations may include checking to determine if the counter value exceeds a predetermined value, e.g., tmax. If yes, automatic labeling stops based on the assumption that all of the relevant values of interest have already been labeled. If no, the process of identifying points of interest begins based on the trained CNN layer model, e.g., example, as in FIG. 13A.

In one embodiment, each iteration of the method may be dedicated to determining whether a respective one or more states of interest exist in the model output. For example, a first iteration may involve determining whether a first state of interest (e.g., one of the aforementioned fiducial points) exist in the output. If there are second and subsequent iterations, determinations are made as to whether other state(s) of interest exist in the model output. These iterations may be accomplished as follows.

At 1358, the trained model analyzes the unlabeled time-series data output from the RF-to-seismocardiogram translator to identify whether one or more states of interest exist, which, for example, may be indicative of medical or health conditions. The identification may be performed, for example, based examining the time positions, amplitudes, and/or patterns of the data points in the time-series that the model has been trained to identify certain ones of the states. Once identified, the model may automatically label (or otherwise indicate) that the seismocardiogram includes these states. Information indicative of respective ones of the states may then be output from corresponding ones of a plurality of channels. Examples will be discussed below.

In one embodiment, identification of the states may correspond to comparing the output of the Automatic Labeler model to reference data, e.g., one or more thresholds or reference data. For example, the model may access a ground-truth series of one or more data points indicative of a corresponding state. The model output may be compared to the ground truth in order to determine whether respective ones of the states exist. In some cases, this may be done on a channel-by-channel basis, with the ground-truth of each channel representing a corresponding cardiac event timing.

In an optional operation, one or more threshold values may be used to eliminate noisy peaks in the model output that could impair proper labeling. In some cases, noise may manifest as lower-level or other forms of spurious data points. Valid data points may exceed the magnitudes of the lower-level points and therefore may be distinguished on this basis. In one embodiment, the lower-level noise points may be identified by applying a noise threshold. The noisy data points may then be eliminated. The data points that remain may be analyzed to determine whether the points correspond to the ground truths of one or more states, for example, based on use of other thresholds, amplitude, time position and/or patterns of those points.

Figure 13D:
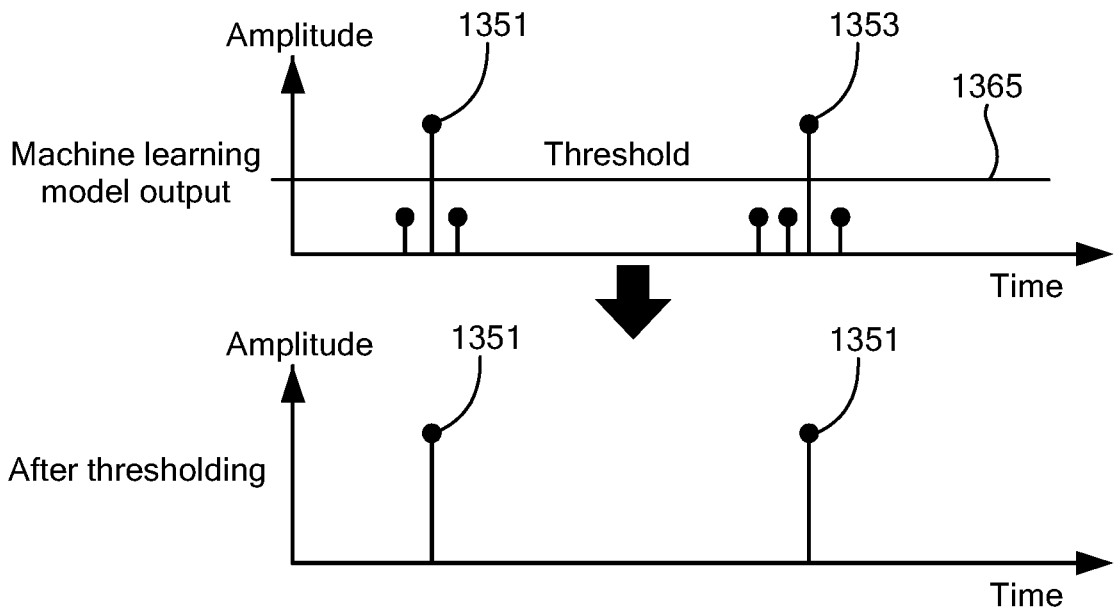
FIGS. 13D-13J are a series of plots which illustrate operations included in a method of performing automatic labeling of one or more fiducial points in a seismocardiogram.

FIG. 13D shows an example of noise elimination in the output of the Automatic Labeler model. In this case, the model output corresponds to a series of data points in the time domain, as shown in the top graph. In this case, two data points 1351 and 1353 are valid data points and the remaining points correspond to noise. The noise may be identified by applying a predetermined threshold level 1365 to the model output data points. The bottom graph shows the valid data points that remain after the noise has been removed. The remaining valid data points may be interpreted by the model as corresponding to one or more of the fiducial points of interest.

Thus, returning to FIG. 13C, when data points exist that exceed a noise threshold during a first iteration for a first corresponding state, then a determination may be made that valid data points exist to be compared to the ground truth for a first state. Put differently, in operation 1358, one or more valid data points are determined to exist that may be indicative of an event timing when those one or more points exceed a noise threshold.

When the threshold is exceeded, then, at 1360, for that iteration and its corresponding state, an output value is changed to a value of 1 and information is output on a corresponding channel that indicates (and thus labels) whether the valid data points match a corresponding ground truth. The counter value t is then incremented at 1362 and control passes back to operation 1356. If t<tmax, then additional iterations are performed to determine whether additional states exist to be labeled.

If, in operation 1358, all of the data points are below the noise threshold, then the output value is set to 0 for that state at 1361. The counter value t is then incremented at additional iterations for additional states are performed, if warranted.

At 1356, when t=tmax, all of the iterations may be considered to have been performed for labeling purposes. At this point, the method may end.

Figure 13E:
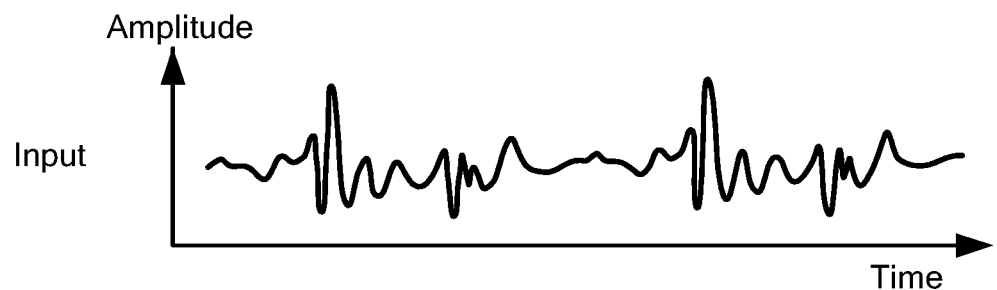
Figure 13F:
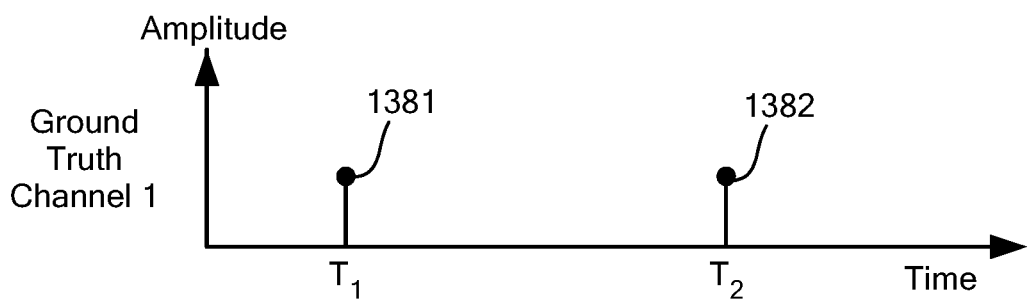

FIGS. 13E to 13J shows examples of ground truths that may be used for corresponding ones of five states of interest, which may correspond to the fiducial points allocated to multiple channels of interest. FIG. 13E shows an example of an input seismocardiogram waveform. FIG. 13F shows a ground truth which may be used by the Automatic Labeler model for comparison to a (noise filtered or unfiltered) time-series of data points of the seismocardiogram waveform for a first fiducial point. In this ground truth, two data points 1381 and 1382 are shown that correspond to first and second time points T1 and T2, respectively. Thus, in this case, if the seismocardiogram waveform has data points at T1 and T2 (and optionally those points exceed one or more thresholds, e.g., a noise threshold and/or a signal threshold), the model may determine the patient being monitored has the corresponding fiducial point (or state) and may automatically label the seismocardiogram as having such.

Figure 13G:
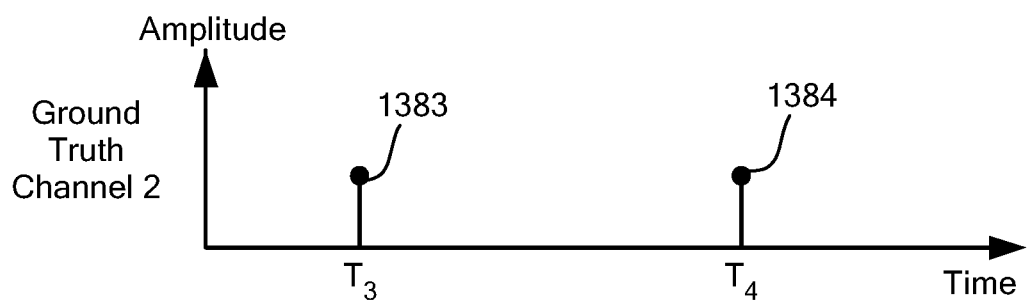

FIG. 13G shows a ground truth which may be used by the Automatic Labeler model for comparison to a (noise filtered or unfiltered) time-series of data points of the seismocardiogram waveform for a second fiducial point. In this ground truth, two data points 1383 and 1384 are shown that correspond to third and fourth time points T3 and T4, respectively. Thus, in this case, if the seismocardiogram waveform has data points at T3 and T4 (and optionally those points exceed one or more thresholds, e.g., a noise threshold and/or a signal threshold), then the model may determine that the patient being monitored has the corresponding fiducial point (or state) and may automatically label the seismocardiogram as having such.

Figure 13H:
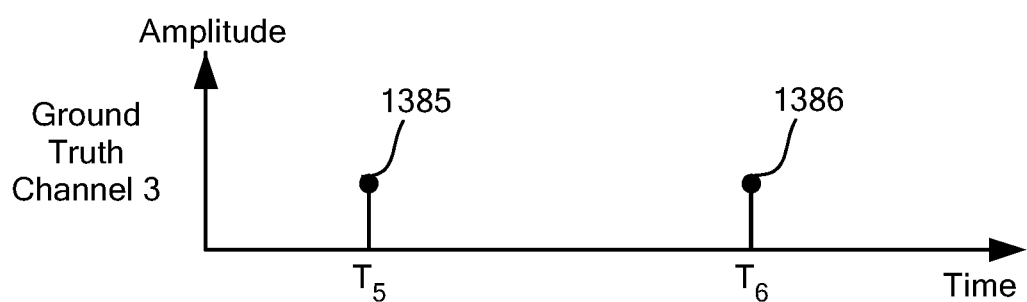

FIG. 13H shows a ground truth which may be used by the Automatic Labeler model for comparison to a (noise filtered or unfiltered) time-series of data points of the seismocardiogram waveform for a third fiducial point. In this ground truth, two data points 1385 and 1386 are shown that correspond to fifth and sixth time points T5 and T6, respectively. Thus, in this case, if the seismocardiogram waveform has data points at T5 and T6 (and optionally those points exceed one or more thresholds, e.g., a noise threshold and/or a signal threshold), then the model may determine that the patient being monitored has the corresponding fiducial point (or state) and may automatically label the seismocardiogram as having such.

Figure 13I:
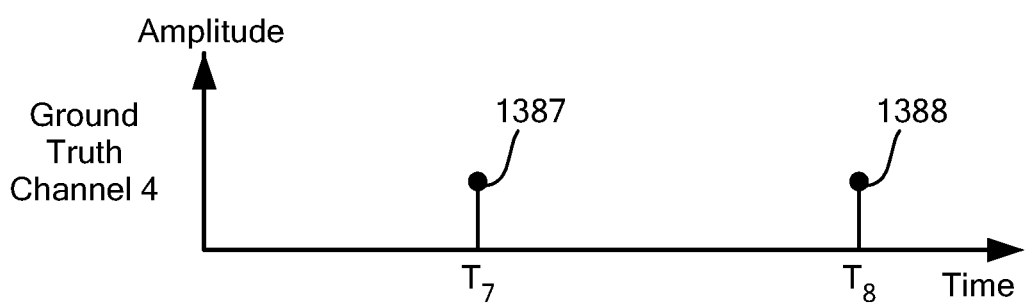

FIG. 13I shows a ground truth which may be used by the Automatic Labeler model for comparison to a (noise filtered or unfiltered) time-series of data points of the seismocardiogram waveform for a fourth fiducial point. In this ground truth, two data points 1387 and 1388 are shown that correspond to seventh and eighth time points T7 and T8, respectively. Thus, in this case, if the seismocardiogram waveform has data points at T7 and T8 (and optionally those points exceed one or more thresholds, e.g., a noise threshold and/or a signal threshold), then the model may determine that the patient being monitored has the corresponding fiducial point (or state) and may automatically label the seismocardiogram as having such.

Figure 13J:
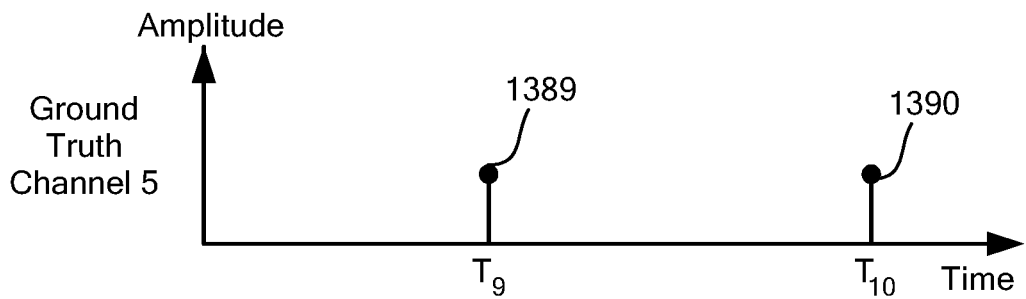

FIG. 13J shows a ground truth which may be used by the Automatic Labeler model for comparison to a (noise filtered or unfiltered) time-series of data points of the seismocardiogram waveform for a fifth fiducial point. In this ground truth, two data points 1389 and 1390 are shown that correspond to ninth and tenth time points T9 and T10, respectively. Thus, in this case, if the seismocardiogram waveform has data points at T9 and T10 (and optionally those points exceed one or more thresholds, e.g., a noise threshold and/or a signal threshold), then the model may determine that the patient being monitored has the corresponding fiducial point (or state) and may automatically label the seismocardiogram as having such.

Through this method, an automatically labeled seismocardiogram and/or corresponding fiducial information may be output through corresponding channels. In this example, the labeled output represent probabilities of up to five fiducial points in existence.

FIGS. 14A to 14F show example waveforms (or signals) indicating how the system 100 may generate seismocardiogram recordings from wireless reflected signals. In these figures, time-series outputs are plotted at different stages of the overall system architecture for a sample experimental trial.

FIG. 14A shows an example of a phase waveform before the differentiator filter of the heart rate estimator 410 is applied. The phase waveform looks irrelevant to seismocardiogram recordings and corresponds to the patient location. In other words, the waveform of FIG. 14A corresponds to the output of the FMCW processing. The plot contains different sources of noise and interference, especially from breathing. For example, the baseline fluctuation (trend) is due to the breathing signal.

FIG. 14B shows an example of the phase waveform after the differentiator filter is applied to the waveform of FIG. 14A, e.g., the case where the breathing signal has been removed. This plot shows finer variations, but remains noisy.

FIG. 14C shows an example of a waveform obtained at the output of the Cardiac Beamformer 310. This plot waveform is much cleaner and has sharper peaks and troughs with better signal-to-noise ratio (SNR). This waveform (or signal) is input into the RF-to-sei seismocardiogram translator 330 for waveform conversion.

FIGS. 14D and 14E show examples of waveforms output at an intermediate stage and the final stage of the translator 330, respectively. As shown in FIG. 14D, the intermediate stage may be difficult to interpret as in most neural networks, but it is interesting to see that it identifies some of the sharp peaks. Thus, in one embodiment after the differentiator filter and the beamforming stage, the trend of the resulting waveform starts showing some micro-cardiac events.

The FIG. 14E plot may be generated by combining the waveforms from all of the channels and is very similar to the ground-truth seismocardiogram recording shown in FIG. 14F, demonstrating the ability to successfully translate the reflected wireless signals (e.g., mmW reflections) into seismocardiogram recordings. Moreover, the FIG. 14E plot shows that system 100 is able to correctly label the fiducial points corresponding to the five micro-cardiac events of interest, as shown by respective ones of the dotted vertical lines. The five fiducial points may be extracted through the operations performed by the Automatic Labeler 350.

Example Implementation

Figure 15:
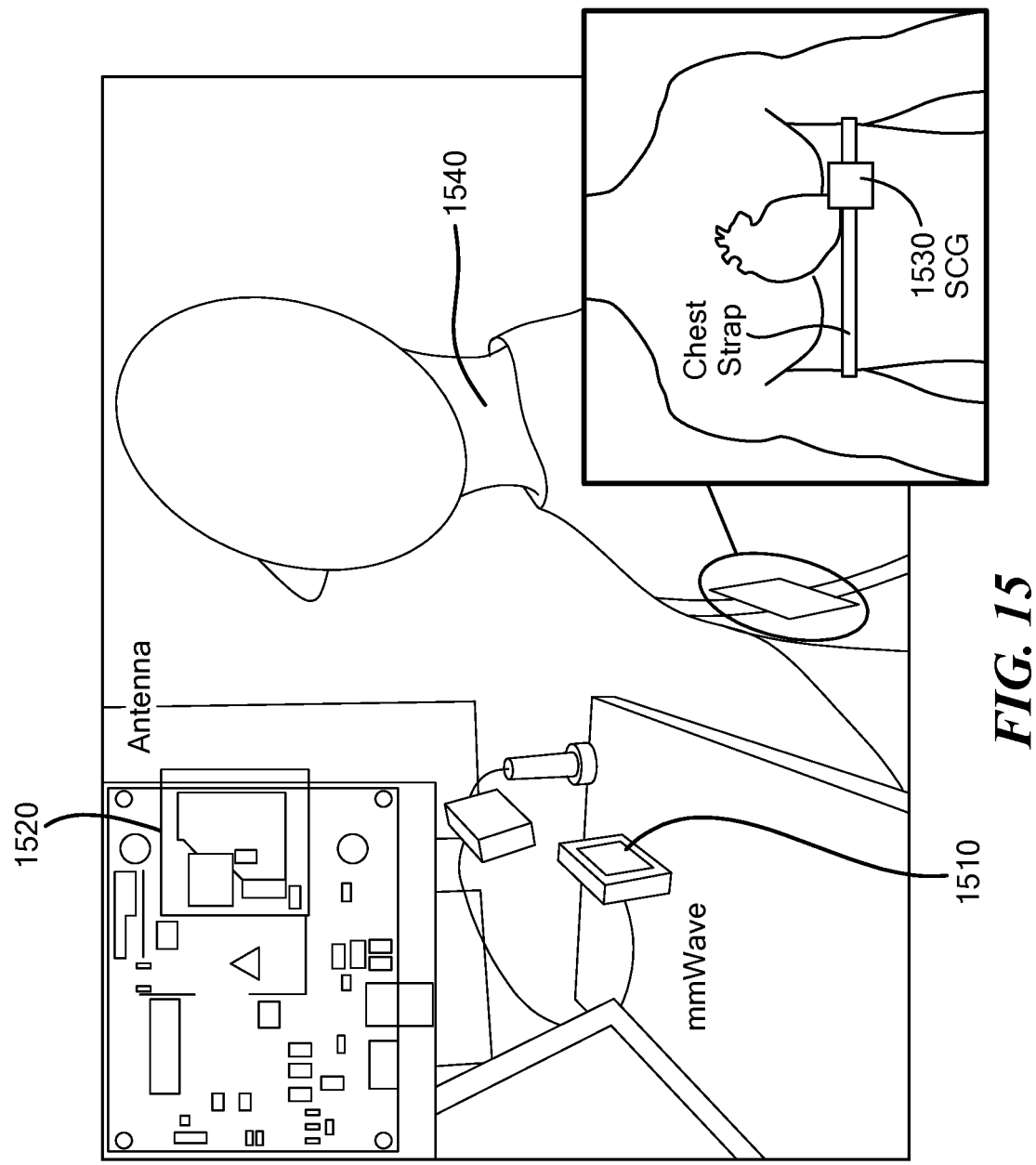
FIG. 15 is a diagram of an example setup for implementing the contactless sensor of FIG. 1.

FIG. 15 shows an example where system 100 combines a mmW sensor 1510 with a real-time data-capture adapter for radar sensing. In this example, the mmW sensor 1510 is an IWR1443BOOST board operating at 77 GHz. Another operational frequency may be used in another embodiment. The radar front-end transmits an FMCW signal (with 4 GHz of bandwidth) and includes two-dimensional linear array antenna 1520. Antenna 1520 included a horizontal component (with 3-dB beamwidth of ±28°) and vertical/elevation component (with 3 dB-beamwidth of ±14°).

The board incorporated a monolithic implementation of a 3Tx, 4Rx system. In order to maintain high temporal resolution for seismocardiogram recordings, 2Tx and 4Rx was used in this example. The board used switched transmissions which enabled isolating of the received signals. The acquired data was sent to a host PC with the help of a capturing software, mmW Studios. For training, a sensor 1530 for capturing seismocardiogram reference data was strapped to the chest of the test subject 1540. During operation, the subject was sitting about 30 cm away from mmW board antennas.

In this example implementation, the models, algorithms, and other instructions (e.g., stored in memory 164 of FIG. 1) were implemented in MAT-LAB R2019b and Python 3.7. These tools included or were augmented with instructions for performing FMCW pre-processing and filtering. With these, mmW Studio was used to configure parameters of IWR1443BOOST. To enable flexibility in signal processing and acquisition, a packet sniffing program was used to capture packets received over Ethernet from the mmW board in real-time. The extracted phase signals were pre-processed in MATLAB using a bandpass FIR filter (0.2-50 Hz) to mitigate the impact of breathing and high frequency noise.

The CNN Template Matcher 412 was implemented with the following hyper-parameters, used for training the CNN: size=600, stride=1, zero-padding=300, and Maxpooling layer size=800, stride=100. In addition, an SGD (Stochastic Gradient Descent) optimizer was used with a learning rate=1e−3. The processing time of the module was 0.4 sec for 3 minutes data set on a machine with an i7-9700 (3.60 GHz) processor, 16 GB RAM, RTX 2080.

For the Cardiac Beamformer, beamforming was performed in post-processing after extracting the individual channels from the radar. The Cardiac Beamformer identified the optimal projection vector. Specifically, in the beamforming function, the power ratio was extracted from a 40×40 grid representing the (x, y) 2D space, and four range buckets (i.e., FMCW frequency buckets) centered around a region of 30 cm from the sensor. The spectral density of the heart reflection is estimated in the frequency domain with a resolution of 5 beats/min.

For the RF-to-seismocardiogram translator, three data augmentation methods were used (namely, overlapping, stretching and noising) from few-shot learning machine-learning models. First, a sliding window function was used to divide the input measurements into frames. The window consisted of 512 samples and was shifted by 32 samples to extract overlapping frames. Second, each frame was stretched or squeezed to represent a large number of heart rates (50-140 bpm, at 10 bpm intervals) using cubic spline data interpolation. Third, each frame was replicated 10 times, each with different power of random noise. This allowed more than 1,000 times the original dataset to be generated and also provided additional resilience to overfitting. To maintain the width of each layer, an Adam optimizer was used and the following CNN parameters were set: size=[101, 101, 101], stride=[50, 50, 50], batch size=64, learning rate=1e−5, stride=1, dropout rate=0.2.

For the Automatic Labeler, a Unet architecture was used to automatically label a plurality of seismocardiogram fiducial points. The size of the layers were modified along with the cropping and concatenation functions. If an output value had a score larger than the reference of 0.5, it was marked as a valid fiducial point. The Adam optimizer was used and set using the following parameters: learning rate=1e−5, beta1=0.9, beta2=0.999.

The Ground Truth (e.g., 1160 in FIG. 11) used in training mode was generated based on data from an on-body accelerometer (KXR94-2283) connected to a customized processing module (ADS1299EEGFE). The sampling rate was set to 500 samples per second. To synchronize the ADS1299 with the mmW sensor, the DRDY pin of the ADS1299 was used as a ticker to clock the SYNC_IN pin of the mmW sensor. The seismocardiogram recording device was only used for training the network. In a real-world use case, the user does not need to wear the device in accordance with one or more embodiments.

A pool of 21 participants (5 females) between the ages of 21 and 35 were used during testing. None of the participants had reported known pre-existing cardiovascular conditions. Participants wore normal daily attire such as T-shirts, blouses and button downs with different fabric materials. Moreover, the testing was performed in an open office environment of an office building with standard furniture and in the presence of with other wireless technologies (WiFi, LTE, Bluetooth, etc.) that might be found during everyday living conditions. Throughout testing, other people were walking around in the environment.

During the data collection process, subjects were asked to sit in a chair within 25-50 cm from the sensor. The mmW sensors were placed in front of the subjects and aimed at the sternum. The ground truth was collected by attaching an accelerometer to the chest of each of the subjects, slightly to the left of their sternums. The attachment was done using adhesive tape or an elastic string wrapped around the chest area.

A total of 169 experimental trials were performed, each lasting for around 3 minutes. During these experiments, subjects were asked to breath normally, but remain quasi-static otherwise (e.g., avoid moving their arms and legs). Subjects could sit relatively comfortably and blink or swallow regularly. About 40,000 heartbeats were collected in total. Subject heart rates varied from 55-110 bpm, and each heartbeat was manually labeled to time each of the 5 fiducial points of interest. The heartbeat labels were inspected multiple times by different individuals to ensure abidance to standard labeling protocols.

Performance Results

Reconstructing the seismocardiogram Waveform. The ability to reconstruct seismocardiogram waveforms from radar reflections may be based on the ability to translate the reflections into recordings that, for example, are typically obtained from on-body accelerometers and/or ones used previously in medical studies.

Performance may also be determined based on how well the RF-to-seismocardiogram translator generalizes for unseen subjects. To do so, the dataset was divided into a training set and testing set. For each subject (e.g., subject 1), the model was trained on twenty other subjects (e.g., subjects 2-21) and evaluated on the untrained subject. This 21-fold cross-validation ensures that the training and testing are mutually exclusive, and that the model is evaluated on subjects it has not been trained on. For each subject, the system remotely captured the seismocardiogram recording and automatically extracted the five fiducial points of interest.

To quantify the similarity between continuous waveform output from the RF-to-seismocardiogram translator and the ground truth, the Pearson Correlation Coefficient was computed. This coefficient represents how closely two variables move together. The RF-to-seismocardiogram translator was also compared to a baseline implementation that performs standard beamforming and bandpass filtering, similar to work on contactless cardiac sensing. For each subject, we divided the time series into 1 second intervals and computed the correlation coefficient for each of these intervals.

Figure 16:
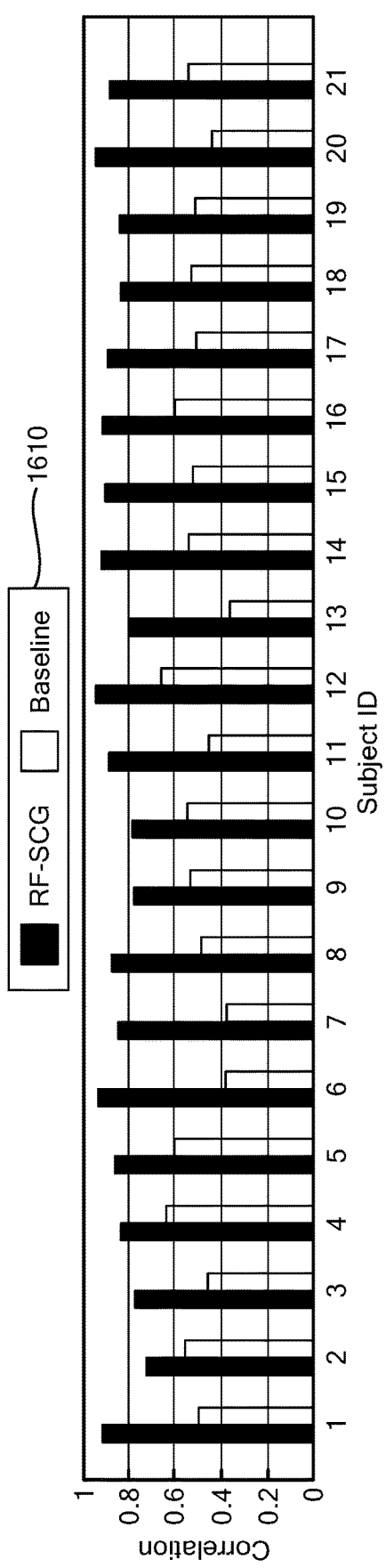
FIG. 16 is a bar graph of RF-SCG and baseline correlation for subjects which illustrates example of performance results achieved by one or more embodiments described herein.

FIG. 16 shows median values of correlation coefficients across the 21 subjects for both RF-to-seismocardiogram translator output and the baseline. The data points are differentiated by the bar shading indicated in the legend 1610. As shown in FIG. 16, the RF-to-seismocardiogram translator correlation coefficient is consistently higher than that of the baseline across all subjects. Moreover, the highest correlation of the baseline method is 0.66. In contrast, the correlation coefficient for the RF-to-seismocardiogram translator of the example embodiment is more than 0.72 correlation coefficient in every case.

Additionally, for 7 out of 21 subjects, RF-to-seismocardiogram translator achieved a very high positive correlation (>0.9), which is substantially greater than other proposed methods that focus on recovering portions of a PCG waveform (specifically, those corresponding to two of the micro-cardiac events) and demonstrate correlations of only 0.80-0.82, at best. This shows that the RF-to-seismocardiogram translator significantly outperforms other methods, and that the Beamformer and RF-to-seismocardiogram translator enable it to learn representative transformations between the reflected signals and on-body accelerations. These results further demonstrate that the translator is capable of reconstructing the entire seismocardiogram waveform.

Timing Micro-Cardiac Events. The ability to precisely time micro-cardiac events from extracted SCG signals and how accuracy varies across subjects are additional ways of assessing performance. Using the same protocol described above, the measurement dataset was divided into training and testing sets. This time, instead of using the continuous time-domain waveform obtained at the output of the RF-to-seismocardiogram translator, performance of the entire processing pipeline of the system may be assessed including the Automatic Labeler. For each detected fiducial point, the error was computed as a time difference between the RF-SCG-estimated timing and the ground truth timing, and was then normalized by the heartbeat period, as per Equation (9):

$$\text{Error} = 100 \times \frac{RF - SCG \text{ Estimated Time} - \text{Ground Truth Time}}{\text{Heartbeat Period}} \quad (9)$$

Figure 17A:
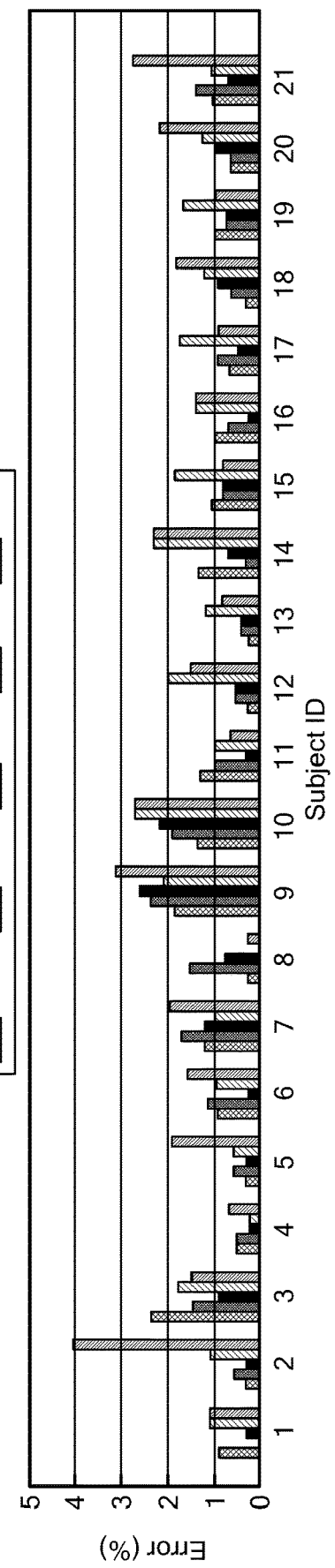
FIG. 17A is a bar graph of system fiducial point error across subjects.

FIG. 17A shows the error of the system 100 across all 21 subjects. Each cluster represents a single subject and the corresponding median accuracy of the five fiducial points, as indicated by the legend 1710. The accuracy of the system 100 may be compared to the accuracy of a cardiac ultrasound device, that is typically used for timing micro-cardiac events. The best-case accuracy may be limited by the quantization error of the device, which results from a sampling period (around 20 ms) and is computed in a similar manner as per the above equation and may correspond to a value of 2.6% on the y-axis in FIG. 17A.

Regarding FIG. 17A, overall, the system 100 is shown that it can maintain low error (e.g., below 2.5%) across almost all subjects and all fiducial points. Also, system 100 matches or exceeds the performance of the best-case accuracy for the cardiac ultrasound (dashed yellow line) for all fiducial points in seven out of the ten subjects.

Figure 17B:
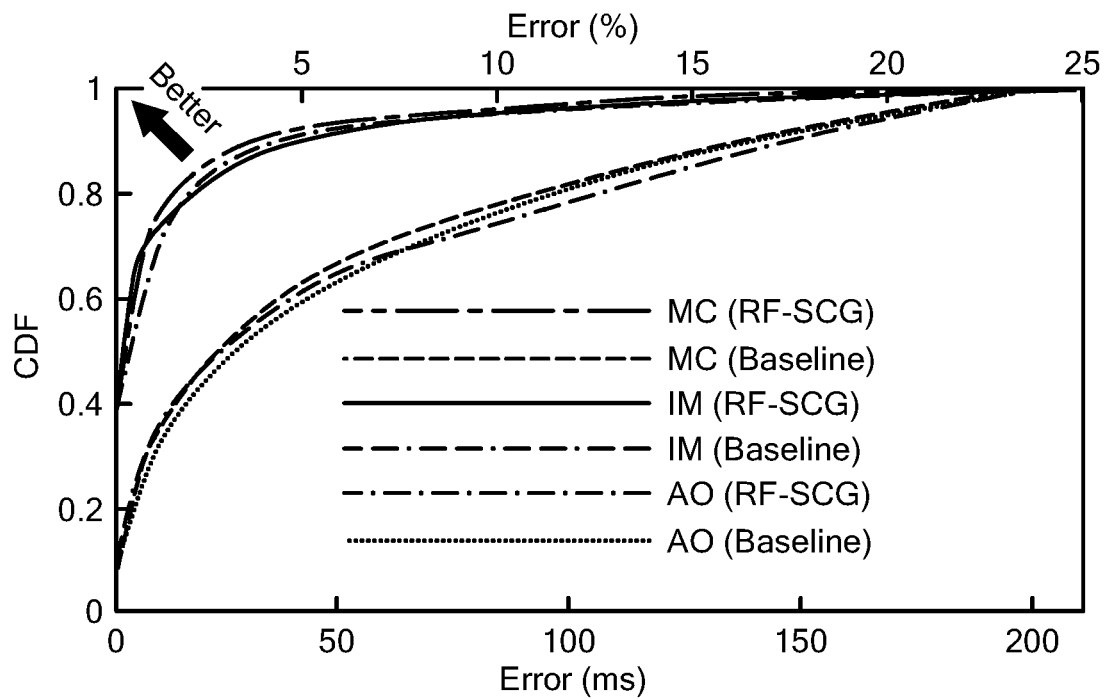
FIG. 17B is a plot of CDF vs. fiducial point error (milliseconds) which illustrates example of performance results achieved by one or more embodiments described herein.
Figure 17C:
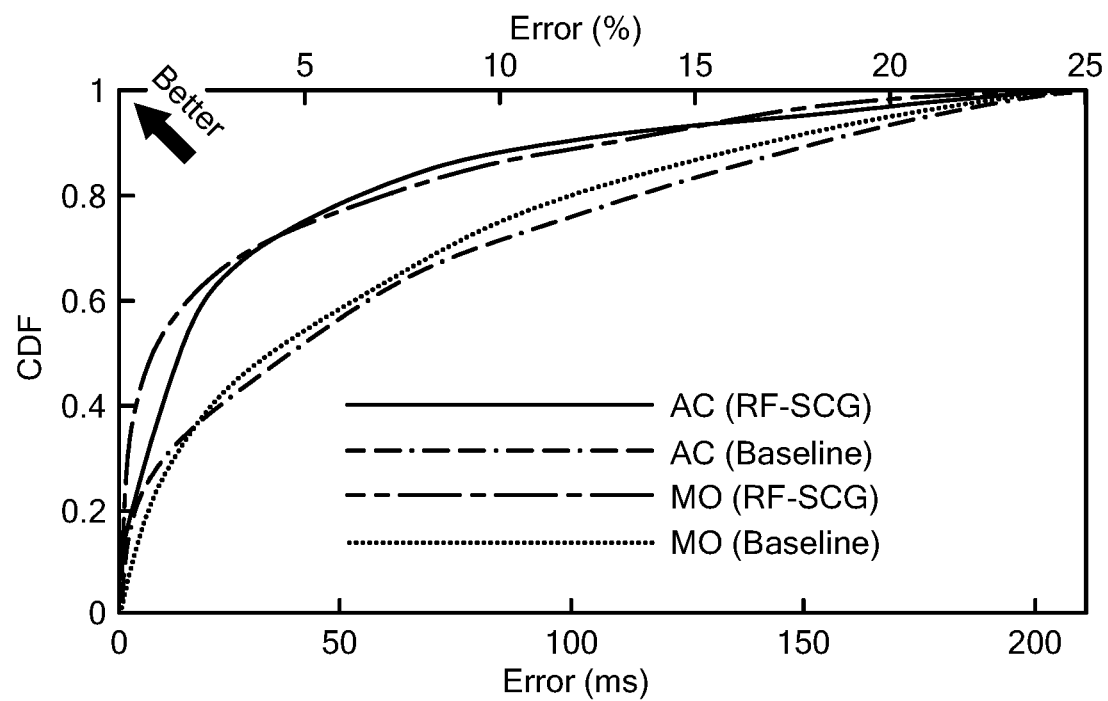
FIG. 17C is a plot of CDF vs. fiducial point error (milliseconds) which illustrates example of performance results achieved by one or more embodiments described herein.

Moreover, if only the systolic micro-cardiac movements (MC, IM, and AO), the accuracy of system 100 matches or exceeds other proposed methods for all subjects. An example is shown in FIG. 17B, which shows a CDF of accuracies for systolic movements or micro-cardiac events. In FIG. 17B, the solid curves correspond to the performance of system 100 and the dotted curves correspond to the performance of a baseline system. The higher accuracy for systolic micro-cardiac events over the diastolic movements (AC, MO), as shown in FIG. 17C, is expected since the systolic movements are stronger (e.g., correspond to heart contraction, while the diastolic fiducial points correspond to relaxation which is a weaker movement). This is the same reason why the stronger (lub) sound of the heartbeat comes from the systolic movements and why their corresponding peaks are larger.

In some scenarios, the median accuracy of system 100 may exceed that best-case accuracy other proposed systems. This is because, in some embodiments, the sampling rate of system 100 may be much higher than that of standard cardiac ultrasound devices. Additionally, the MO of the second subject has the highest error (around 4%). The corresponding error accounts for only two sampling periods in cardiac ultrasound.

The benefits of RF-SCG's timing accuracy against a simpler baseline that learns an "average" human heartbeat template may be quantified as follows. Other proposed methods (baseline) can only extract at most two fiducial points. In accordance with one or more embodiments, the system 100 may implement a "stretched template" method which operates as follows. After segmenting the recorded signals into individual heartbeats (as per the Cardiac Beamformer), we stretch each individual heartbeat cycle may be stretched to fit in one second.

Then, the fiducial points of each subject may be estimated using the remaining averaged SCG signals of the subject. Even though this baseline is already given the advantage of the segmentation algorithm as previously discussed, it allows the value of the remaining stages to be investigated in recovering meaningful variations across heartbeats.

FIGS. 17B and 17C may be described in greater detail as follows. These figures plot a CDF of the error for system 100 and the baseline for each of the five fiducial points. Each of the CDFs in this figure corresponds to the combined error across all subjects. The plot shows both the absolute error (bottom x-axis) and relative error (top x-axis).

As shown, the system 100 outperforms the baseline across all fiducial points. The median improvement varies from around 3 times for MO up to 12 times for AO. This demonstrates that the example implementation of system 100 significantly outperforms the baseline (e.g., regular stretched template) method and that system 100 has sufficient accuracy to capture variability across individuals. In addition, median errors in timing the fiducial points (reported as absolute error/percentage per Equation (7) are: 2 ms/0.26% (MC), 4 ms/0.52% (IM), 4 ms/0.52% (AO), 12 ms/1.55% (AC), 10 ms/1.29% (MO). These errors are 3 to 12 times less than the variability of individual heartbeats even for healthy individuals.

Also, similar to earlier results, system 100 may have higher accuracy in timing systolic (MC, IM, AO) than diastolic (AC, MO) fiducial points, as shown by a comparison of FIGS. 10B and 10C. As indicated, this is due to the stronger SNR of systolic vibration (stronger sound of the heartbeat) than diastolic one.

Decomposing RF-SCG's Gains. The accuracy gains arising from subcomponents of the example implementation of system 100 may be quantified as follows. For example, the accuracy of partial implementations of system 100 may be compared with the overall system as follows: (1) partial implementation using conventional beamforming (Conventional BF) to extract coordinates at the highest power, combined with a differentiator filter of system 100, (2) partial implementation using conventional beamforming combined with the RF-to-seismocardiogram translator of system 100, and (3) the full architecture of system 100 with its Cardiac Beamformer and RF-to-seismocardiogram translator. The Automatic Labeler may be applied to all three cases.

Figure 18:
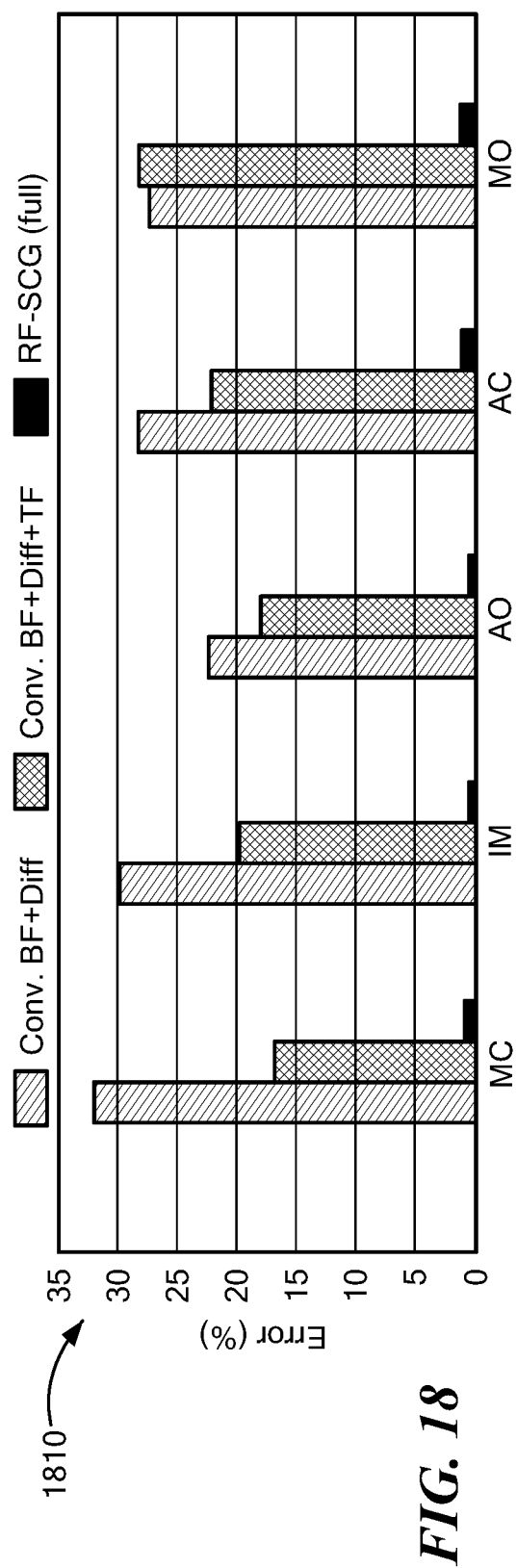
FIG. 18 is a bar graph of fiducial point error which illustrates example performance results achieved by one or more embodiments described herein.

FIG. 18 plots an example of the accuracy for each of the above partial implementations. For simplicity, FIG. 18 only plots the results for a single subject. The legend 1810 differentiates the data for each of these cases. Similar to evaluation previously explained, the models were trained on all other subjects (e.g., aside from the one used in evaluation).

As shown in FIG. 18, both partial implementations achieve significantly higher errors than the full implementation of system 100. For example, the absence of the Cardiac Beamformer increases the error of the sensor to 15%-27% across all fiducial points. The absence of the RF-to-seismocardiogram translator further increases its error up to 32%. This demonstrates how improved performance may be obtained by a combination of the subcomponents in system 100 in some embodiments.

Precision & Recall of Automatic Labeling. Some of the previous evaluations have focused on measuring the correlation of waveforms and temporal errors between fiducial points labeled by an example implementation of system 100 and the ground-truth time of corresponding cardiac movements. An additional evaluation may be performed to gain more insight into the ability of system 100 to detect these fiducial points. In performing this evaluation, the same dataset was used (e.g., testing and training was mutually exclusive on all subjects) and a precision metric was computed based on Equation (10) and a recall metric was computed based on Equation (11).

$$\text{Precision} = \frac{\text{\# Correct Detections}}{\text{\# of Reported Detections}} \quad (10)$$

$$\text{Recall} = \frac{\text{\# Correct Detections}}{\text{\# of Ground Truth Instances}} \quad (11)$$

In this case, a detection may be considered to be correct if the error between the detected time by system 100 and the ground-truth time according to the ground truth (from accelerometer) is within a sampling error of a cardiac ultrasound. Intuitively, the precision metric scores how well the detected points match the manually labeled points, while the recall metric scores the ability of the system to detect all the manually labeled points in the SCG.

Figure 19:
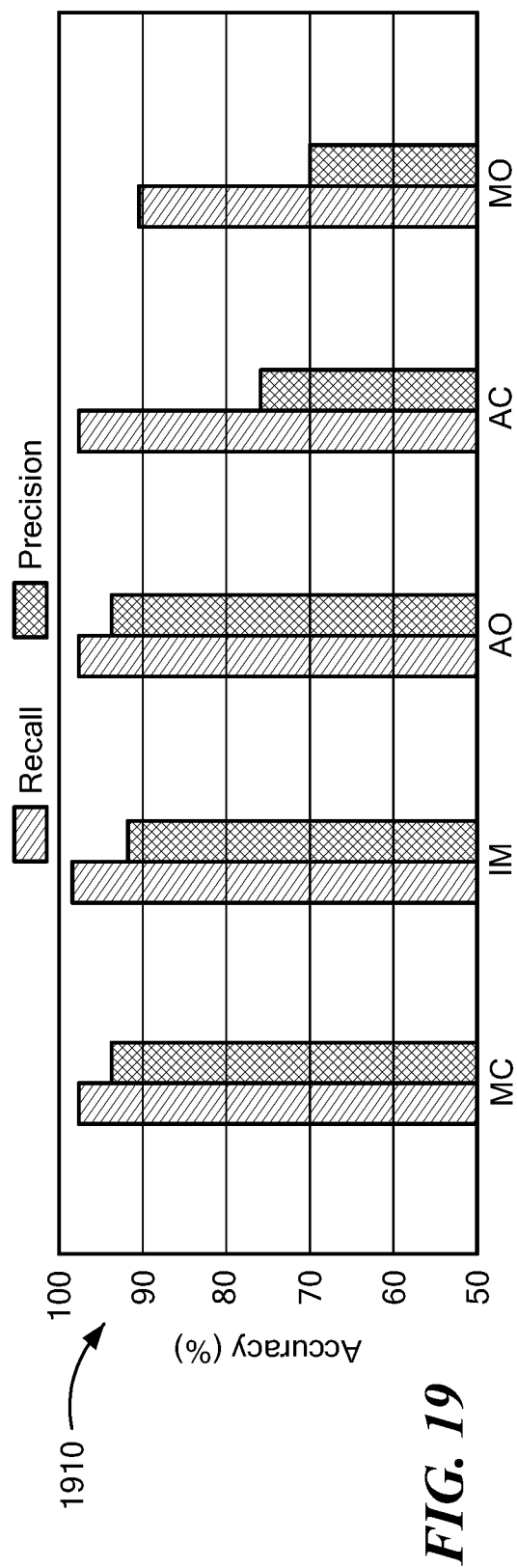
FIG. 19 is a bar graph of fiducial point error which illustrates example performance results achieved by one or more embodiments described herein.

FIG. 19 shows the precision and recall metrics for each of the fiducial points across all the subjects, and the legend 1910 shows which data points correspond to the recall and precision metrics. (Recall that these metrics differ from the accuracy metric discussed earlier).

As shown in FIG. 19, the precision of the example implementation of system 100 is around or above 90% across all the fiducial points. However, only three of the fiducial points have recall scores higher than 90%. For diastolic fiducial points, the recall is lower than precision by 20.2% but the detected point are highly likely to be correct. In some embodiments, it is possible to make the Automatic Labeler more aggressive by adjusting the loss function of the training regime and threshold of score value to favor recall.

Since the system 100 can sense fiducial points within a heartbeat, in some embodiments it may not be necessary to extract all fiducial points from each the heartbeats because the heartbeats repeat over time. This is why precision may be considered to be a better metric to evaluate the performance of the labeling function in some applications. In that sense, the Automatic Labeler of system 100 shows very good accuracy. Nonetheless, in some applications, it may be desirable to adjust the training parameters differently, for example, depending on the cardiovascular condition of interest.

Modality Performance and Environmental Considerations. An additional evaluation that may be performed focuses on various sources of error for both the example implementation of system 100 and other proposed methods for obtaining seismocardiogram recordings (e.g., ones using a chest-attached accelerometer). As previously discussed, some embodiments of system 100 may implement outlier rejection. Accordingly, at least most of the corrupted regions may be eliminated in these scenarios. In this evaluation, the outlier rejection function of system 100 (labeled RF-SCG) was turned off in order to demonstrate the impact of such problems on the recordings.

Figure 20A:
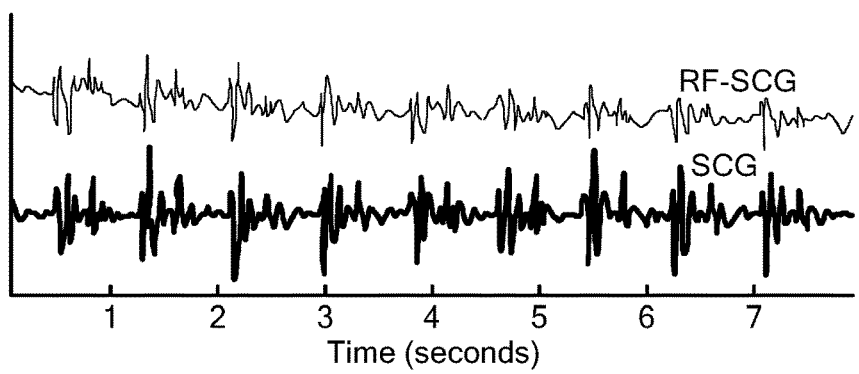
FIGS. 20A to 20D area series of plots of amplitude vs. time for seismocardiogram waveforms which illustrates performance results achieved by one or more embodiments herein.

FIGS. 20A to 20D shows examples of output signals for both modalities when there are different environmental problems. FIG. 20A shows the most common case. Here, the subject remains quasi-static and there is no interference from surrounding objects.

Figure 20B:
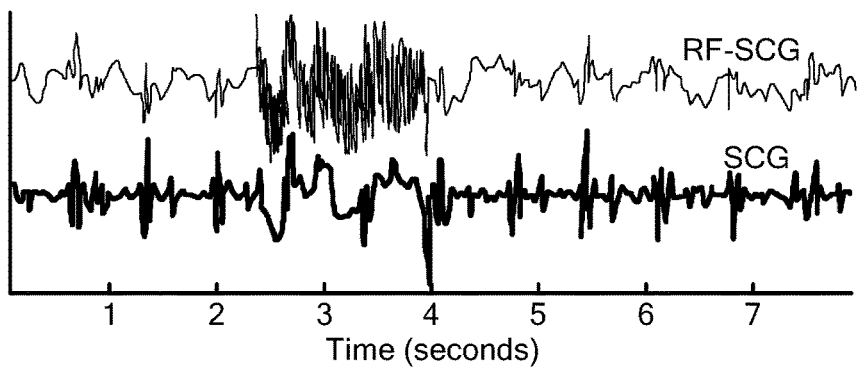

FIG. 20B shows the case when the subject rotates his or her body during the experiment. During the movement, both modalities (RF-SCG and SCG) experience a corrupted region, and then go back to the common case of FIG. 20A when the subject becomes quasi-static again.

Figure 20C:
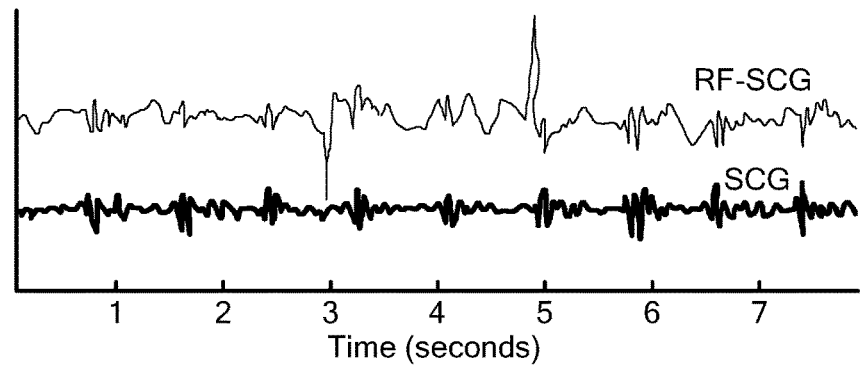

FIG. 20C shows the signals obtained when there is interference from a nearby object. Here, as the subject was sitting, the hand of another user swung between the subject and the mmW sensor to create interference. Even though the signal of the RF-SCG was partially distorted, it still exhibited some fiducial points during the period. On the other hand, the on-body accelerometer (SCG) was not affected at all by this kind of interference.

Figure 20D:
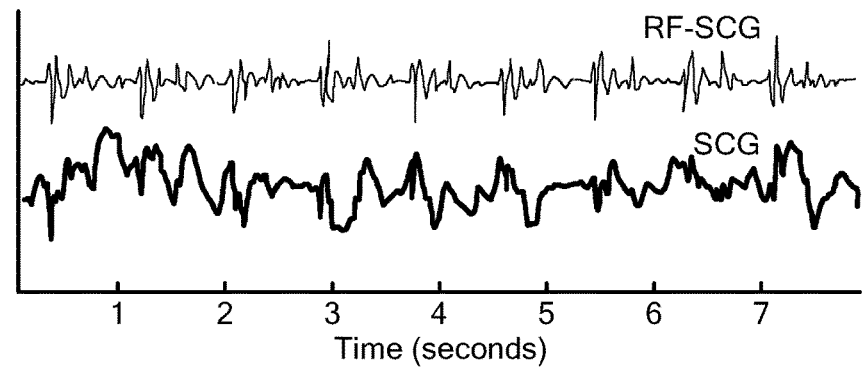

FIG. 20D shows the case when there is an attachment problem in conventional SCG modality. Since this modality requires the accelerometer to be firmly affixed to the chest of a subject (to maintain high SNR), it suffers when the attachment becomes loose. In contrast, the RF-seismocardiogram waveform shows very clean signals because it is based on contactless sensing.

In accordance with one or more of the aforementioned embodiments, a system and method are provided which generate seismocardiogram recordings with greater accuracy than other methods, and which then automatically label a plurality of cardiac-related events that are embedded in the seismocardiogram recordings. All of these performance enhancements are achieve by using a completely contactless sensor in monitoring mode, i.e., one that requires no accelerometers or other equipment that contacts the body of a patient to be monitored. the contactless sensor may be a radar sensor (based on wireless RF signals) or a sonar sensor (based on acoustic or ultrasonic signals).

One particularly beneficial aspect is the ability of various ones of the system and method embodiments to automatically detect and label a plurality of micro-cardiac events within one heartbeat, a result not possible with other systems and methods which have been proposed.

In addition, the improved accuracy of the seismocardiogram recordings and the automatic labeling of micro-cardio events may improve health monitoring in both clinical and non-clinical settings. Also, the contactless nature of the system and method allow for their integration into a variety of electronic and consumer products, including but not limited to smartphones, tablets, and notebook or desk-top computers. The embodiments are also ideal for patients with sensitive skin (e.g., burn patients), which the use of sensors that contact the body is not possible or highly undesirable.

In addition, various embodiments of the system and method may generate accurate seismocardiogram recordings and labeled events, even when patients change posture or location during the monitoring period. Other proposed approaches are unable to achieve accuracy under these conditions. Also, various embodiments of the system and method may employ techniques that allow for accurate seismocardiogram recordings to be generated and labeled in the presence of environmental noise and motion from others in the monitoring area. These noise sources prevent other methods from recording micro-vibrations with corresponding fine-grained cardiovascular events.

In addition to the aforementioned benefits, the contactless nature of the system and method embodiments may use by members of high-risk populations (e.g., elderly, neonates, or patients with arrhythmia) ideal, especially when used at home, work, or other types of everyday environments. Existing methods are performed in diagnostic or medical settings because of the equipment (including accelerometers, ECG leads, and other types of on-body sensors) used.

The methods, processes, and/or operations described herein may be performed by code or instructions to be executed by a computer, processor, controller, or other signal processing device. The computer, processor, controller, or other signal processing device may be those described herein or one in addition to the elements described herein. Because the algorithms that form the basis of the methods (or operations of the computer, processor, controller, or other signal processing device) are described in detail, the code or instructions to implement the operations of the method embodiments may transform the computer, processor, controller, or other signal processing device into a special-purpose processor for performing the methods described herein.

The controllers, processors logic, filters, extractors, models, algorithms, beamformers, translators, template matchers, detectors, calculators, labelers, analyzers, and other signal-generating and signal-processing features described herein may be implemented in non-transitory logic which, for example, may include hardware, software, or both. When implemented at least partially in hardware, the controllers, processors logic, filters, extractors, models, algorithms, beamformers, translators, template matchers, detectors, calculators, labelers, analyzers, and other signal-generating and signal-processing features may be, for example, any one of a variety of integrated circuits including but not limited to an application-specific integrated circuit, a field-programmable gate array, a combination of logic gates, a system-on-chip, a microprocessor, or another type of processing or control circuit.

When implemented in at least partially in software, the controllers, processors logic, filters, extractors, models, algorithms, beamformers, translators, template matchers, detectors, calculators, labelers, analyzers, and other signal-generating and signal-processing features may include, for example, a memory or other storage device for storing code or instructions to be executed, for example, by a computer, processor, microprocessor, controller, or other signal processing device. The computer, processor, microprocessor, controller, or other signal processing device may be those described herein or one in addition to the elements described herein. Because the algorithms that form the basis of the methods (or operations of the computer, processor, microprocessor, controller, or other signal processing device) are described in detail, the code or instructions for implementing the operations of the method embodiments may transform the computer, processor, controller, or other signal processing device into a special-purpose processor for performing the methods described herein.

Also, another embodiment may include a computer-readable medium, e.g., a non-transitory computer-readable medium, for storing the code or instructions described above. The computer-readable medium may be a volatile or non-volatile memory or other storage device, which may be removably or fixedly coupled to the computer, processor, controller, or other signal processing device which is to execute the code or instructions for performing the method embodiments or operations of the apparatus embodiments described herein.

Any reference in this specification to an "embodiment" means that a particular feature, structure, or characteristic described in connection with the embodiment is included in at least one embodiment of the concepts, systems, device and techniques described herein. The appearances of such phrases in various places in the specification are not necessarily all referring to the same embodiment. Further, when a particular feature, structure, or characteristic is described in connection with any embodiment, it is submitted that it is within the purview of one skilled in the art to effect such feature, structure, or characteristic in connection with other ones of the embodiments. The features of any one embodiment may be combined with features of one or more other embodiments described herein to form additional embodiments.

Furthermore, for ease of understanding, certain functional blocks may have been delineated as separate blocks; however, these separately delineated blocks should not necessarily be construed as being in the order in which they are discussed or otherwise presented herein. For example, some blocks may be able to be performed in an alternative ordering, simultaneously, etc.

Although the concepts, systems, devices and techniques have been described herein with reference to a number of illustrative embodiments, it should be understood that numerous other modifications and embodiments can be devised by those skilled in the art that will fall within the spirit and scope of the principles of the concepts, systems, devices and techniques described herein. For example, variations and modifications are possible in the component parts and/or arrangements of the subject combination arrangement within the scope of the foregoing disclosure, the drawings and the appended claims without departing from the spirit of the concepts, systems, devices and techniques sought to be protected herein. In addition to variations and modifications in the component parts and/or arrangements, alternative uses are also be apparent to those skilled in the art.

We claim:

1. A system comprising:
   a wireless transmit and receive circuit comprising transmit antenna elements configured to transmit wireless signals and receive antenna elements configured to receive wireless reflections of the transmitted wireless signals; and
   a cardiac beamformer comprising:
      a heart signal extractor configured to receive channel signals from the receive antenna elements and in response extract a heart signal using a convolutional neural network (CNN);
      a phase extractor configured to receive the channel signals and in response generate projection signals by isolating groups of the channel signals into different buckets; and
      an extractor configured to identify a spatial beam for analyzing wireless reflections based on the extracted heart signal and the generated projection signals.

2. The system of claim 1, further comprising a wireless-to-seismocardiogram translator configured to implement a machine-learning model to translate information extracted from the spatial beam to a seismocardiogram.

3. The system of claim 1, further comprising an automatic labeler configured to label features of a seismocardiogram.

4. The system of claim 3, wherein the features comprise at least two features within a heart beat in the seismocardiogram.

5. The system of claim 1, wherein the wireless transmit and receive circuit is configured to transmit and receive frequency modulated continuous wave (FMCW) signals.

6. The system of claim 1, wherein:
   the wireless transmit and receive circuit comprises a one-dimensional (1D) array of antenna elements, and
   the wireless transmit and receive circuit is configured to transmit and receive frequency modulated continuous wave (FMCW) signals.

7. The system of claim 1, wherein:
   the wireless transmit and receive circuit comprises a two-dimensional (2D) array of antenna elements, and
   the wireless transmit and receive circuit is configured to transmit and receive frequency modulated continuous wave (FMCW) signals.

8. The system of claim 1, wherein:
   the heart signal extractor is configured to receive phase data from at least two transmit-receive antenna element pairs, and
   the CNN is configured to extract the heart signal based on at least the phase data.

9. The system of claim 1, wherein:
   the heart signal extractor is configured to receive a filtered time series of phase data from at least two transmit-receive antenna element pairs, and
   the CNN is configured to extract the heart signal based on at least the filtered time series of phase data.

10. The system of claim 1, wherein the wireless transmit and receive circuit is configured to operate in the radio frequency (RF) range.

11. The system of claim 1, wherein the wireless transmit and receive circuit is configured to operate in the millimeter wave (MMW) frequency range.

12. The system of claim 1, wherein the wireless transmit and receive circuit is configured to operate in the acoustic frequency range.

13. The system of claim 1, wherein the wireless transmit and receive circuit is configured to operate in the ultrasonic frequency range.

14. A system, comprising:
- a receiver configured to receive wireless signals derived from a heart; and
- at least one processor configured to:
    - translate the wireless signals to a seismocardiogram based on coefficients determined using a first machine learning model; and
    - detect and label at least two features in at least one heart beat in the seismocardiogram using a second, different, machine learning model.

15. The system of claim 14, wherein the receiver is configured to receive the wireless signals from a beamformer.

16. The system of claim 14, wherein at least one of the first machine learning model or the second machine learning model comprises a CNN-based model.

17. The system of claim 14, wherein the at least two features comprises five features, the five features corresponding to an aortic valve opening (AO), aortic valve closing (AC), mitral valve opening (MO), mitral valve closing (MC), and isovolumetric contracting (IM).

18. The system of claim 14, wherein the receiver is configured to receive radio frequency signals.

19. The system of claim 14, wherein the receiver is configured to receive acoustic signals.

20. The system of claim 14, wherein the receiver is configured to receive ultrasonic frequency signals.

* * * * *